US012728139B2

(12) United States Patent
Buceta Fernandez et al.

(10) Patent No.: US 12,728,139 B2
(45) Date of Patent: Sep. 8, 2026

(54) METHODS OF PREPARING PURIFIED ATOMIC QUANTUM CLUSTERS

(71) Applicant: NANOGAP SUB-NM-POWDER, S.A., Ames-A Coruna (ES)

(72) Inventors: David Buceta Fernandez, Ames-A Coruna (ES); Fernando Dominguez Puente, Ames-A Coruna (ES); Manuel Arturo Lopez Quintela, Ames-A Coruna (ES)

(73) Assignee: NANOGAP SUB-NM-POWDER, S.A., Ames-A Coruna (ES)

( * ) Notice: Subject to any disclaimer, the term of this patent is extended or adjusted under 35 U.S.C. 154(b) by 895 days.

(21) Appl. No.: 17/057,677

(22) PCT Filed: Jun. 11, 2019

(86) PCT No.: PCT/ES2019/070403

§ 371 (c)(1),
(2) Date: Nov. 22, 2020

(87) PCT Pub. No.: WO2019/238995

PCT Pub. Date: Dec. 19, 2019

(65) Prior Publication Data

US 2021/0197256 A1 Jul. 1, 2021

(30) Foreign Application Priority Data

Jun. 12, 2018 (EP) .................................... 18177210

(51) Int. Cl.
*A61K 33/24* (2019.01)
*A61K 31/7068* (2006.01)
(Continued)

(52) U.S. Cl.
CPC .......... *A61K 33/24* (2013.01); *A61K 31/7068* (2013.01); *A61K 33/38* (2013.01);
(Continued)

(58) Field of Classification Search
None
See application file for complete search history.

(56) References Cited

U.S. PATENT DOCUMENTS

2009/0035852 A1* 2/2009 Lopez Quintela ..... A61K 33/34 420/466
2014/0106465 A1* 4/2014 Lopez Quintela .......................... G01N 33/5432 436/172

(Continued)

FOREIGN PATENT DOCUMENTS

CN 101248003 A 8/2008
CN 104588645 A 5/2015

(Continued)

OTHER PUBLICATIONS

Hartmann, M. et al., "Theoretical exploration of femtosecond multi-state nuclear dynamics of small clusters", J. of Chemical Physics, vol. 108, No. 8. pp. 3096-3113, Feb. 22, 1998.*

(Continued)

*Primary Examiner* — George Wyszomierski
(74) *Attorney, Agent, or Firm* — HULTQUIST, PLLC; Steven J. Hultquist

(57) ABSTRACT

There is provided an invention relating to methods of purifying atomic quantum clusters, in particular those consisting of 3 or fewer zero-valent metal atoms. The invention also relates to compositions and uses of such compositions, for the treatment of cell proliferative disorders.

7 Claims, 21 Drawing Sheets

(51) Int. Cl.

| | |
|---|---|
| ***A61K 33/38*** | (2006.01) |
| ***A61K 45/06*** | (2006.01) |
| ***A61P 35/04*** | (2006.01) |
| ***B22F 1/05*** | (2022.01) |
| ***B22F 1/052*** | (2022.01) |
| ***B22F 1/054*** | (2022.01) |
| *B82Y 5/00* | (2011.01) |
| *B82Y 30/00* | (2011.01) |
| *B82Y 40/00* | (2011.01) |

(52) U.S. Cl.

CPC .............. *A61K 45/06* (2013.01); *A61P 35/04* (2018.01); *B22F 1/052* (2022.01); *B22F 1/054* (2022.01); *B82Y 5/00* (2013.01); *B82Y 30/00* (2013.01); *B82Y 40/00* (2013.01)

(56) References Cited

U.S. PATENT DOCUMENTS

| | | | | |
|---|---|---|---|---|
| 2014/0203213 | A1* | 7/2014 | Thalappil .............. | B82Y 20/00 252/301.36 |
| 2015/0037585 | A1 | 2/2015 | Compel et al. | |

FOREIGN PATENT DOCUMENTS

| | | | |
|---|---|---|---|
| CN | 106862584 | A | 6/2017 |
| EP | 1914196 | A1 | 4/2008 |
| EP | 2457572 | A1 | 5/2012 |
| JP | 20148499 | A | 1/2014 |
| JP | 201823945 | A | 2/2018 |
| WO | 2012059572 | A1 | 5/2012 |

OTHER PUBLICATIONS

Georgsen, M.B., "An in vitro study of a colloid silver health product and atomic quantum clusters of silver and gold", master thesis, Faculty of Pharmaceutical Sciences, Copenhagen University, Jun. 2007.*

Boo, D.W. et al., "Femtosecond Dynamics of Linear Ag3", Journal of Physical Chemistry A, vol. 101, pp. 6688-6696, Sep. 4, 1997.*

Attia, Y., et al., "Structure-Directing and High-Efficiency Photocatalytic Hydrogen Production by Ag Clusters", Journal of the American Chemical Society, 2014, pp. 1182-1185, vol. 136, Publisher: ACS Publications.

Banerjee, A., et al., "The DNA intercalators ethidium bromide and propidium iodide also bind the core histones", FEBS Open Bio, 2014, pp. 251-259, No. 4, Publisher: Elsevier.

Barone, V., et al., "Quantum Calculation of Molecular Energies and Energy Gradients in Solution by a Conductor Solvent Model", J. Phys. Chem. A, 1998, pp. 1995-2001, vol. 102, Publisher: American Chemical Society.

Bates, W.M., et al., "Multicolor Super-resolution Imaging with Photo-switchable Fluorescent Probes", Science, 2007, pp. 1749-1753, vol. 317, Publisher: National Institute of Health.

Bjergbaek, L., Editor, "DNA Repair Protocols", Methods in Molecular Biology 920, 2012, Third Edition, Publisher: Humana Press.

Boettiger, A., et al., "Super-resolution imaging reveals distinct chromatin folding for different epigenetic states", Nature, 2016, pp. 418-422, vol. 529, Publisher: HHS Public Access.

Borrajo, E., et al., "Docetaxel-loaded polyglutamic acid-PEG nanocapsules for the treatment of metastatic cancer", Journal of Controlled Release, 2016, pp. 263-271, vol. 238, Publisher: Elsevier.

Buceta, D., et al., "Ag2 and Ag3 Clusters: Synthesis, Characterization, and Interaction with DNA", Angew. Chem, 2015, pp. 7722-7726, vol. 127, Publisher: Wiley Online Library.

Cheung-Ong, K., et al., "DNA-Damaging Agents in Cancer Chemotherapy: Serendipity and Chemical Biology", Chemistry & Biology, 2013, pp. 648-659, vol. 20, Publisher: Cell Press; Elsevier Ltd.

Collins, A., "The Comet Assay for DNA Damage and Repair", Molecular Biotechnology, 2004, pp. 249-261, vol. 26.

Comenge, J., et al., "Detoxifying Antitumoral Drugs via Nanoconjugation: The Case of Gold Nanoparticles and Cisplatin", PLoS One, 2012, p. e47562, vol. 7, No. 10, Publisher: Open Access.

Corma, A., et al., "Exceptional oxidation activity with size-controlled supported gold clusters of low atomicity", Nature Chemistry, 2013, pp. 1-7, vol. DOI: 10.1038/NCHEM. 1721, Publisher: McMillan Publishers Limited.

Cui, Z.Y., et al., "Mouse Orthotopic Lung Cancer Model Induced by PC14PI6", Cancer Res Treat, 2006, pp. 234-239, vol. 38, No. 4.

Davey, G., et al., "Nucleosome acidic patch-targeting binuclear ruthenium compounds induce aberrant chromatin condensation", Nature Communications, 2017, pp. 1-13, DOI: 10.1038/s41467-017-01680-4, vol. 8, No. 1575, Publisher: www.nature.com/naturecommunications.

Galluzzi, L., et al., "Molecular mechanisms of cisplatin resistance", Oncogene, 2012, pp. 1869-1883, vol. 31, Publisher: Macmillan Publishers Limited.

Galluzi, L., et al., "Systems biology of cisplatin resistance: past, present and future", Cell Death and Disease, 2014, pp. 1-18, e1257, vol. 5, doi:10.1038/cddis.2013.428, Publisher: Macmillan Publishers Limited.

Gonzalez, V., et al., "Is Cisplatin-Induced Cell Death Always Produced by Apoptosis", Molecular Pharmacology, 2001, pp. 657-663, vol. 59, No. 4, Publisher: The American Society for Pharmacology and Experimental Therapeutics.

Gonzalez, B.S., et al., "Single step electrochemical synthesis of hydrophilic/hydrophobic Ag5 and Ag6 blue luminescent clusters", Nanoscale, 2012, pp. 7632-7635, vol. 4, Publisher: The Royal Society of Chemistry.

Gross, D., "Nuclease Hypersensitive Sites in Chromatin", Ann. Rev. Biochem., 1988, pp. 159-197, vol. 57.

Groth, A., et al., "Chromatin Challenges during DNA Replication and Repair", Cell, 2007, pp. 721-733, vol. 128, Publisher: Elsevier, Inc.

Gupta, P., et al., "Nucleosome Assembly Depends on the Torsion in the DNA Molecule: A Magnetic Tweezers Study", Biophysical Journal, 2009, pp. 3150-3157, vol. 97, Publisher: The Biophysical Society.

Gurova, K., "New hopes from old drugs: revisiting DNA-binding small molecules as anticancer agents", Future Oncol., 2009, pp. 1685-1704, vol. 5, No. 10, Publisher: Future Science Group (FSG).

Hall, M.D., et al., "The Role of Cellular Accumulation in Determining Sensitivity to Platinum-Based Chemotherapy", The Annual Review of Pharmacology and Toxicology, 2008, pp. 495-535, vol. 48.

Huseyinova, S., et al., "Synthesis of Highly Stable Surfactant-free Cu Clusters in Water", The Journal of Physical Chemistry, 2016, DOI: 10.1021/acs.jpcc.5b12227, Publisher: ACS Publications.

Kelland, L., "The resurgence of platinum-based cancer chemotherapy", Nature Reviews Cancer, 2007, pp. 573-584, vol. 7, Publisher: Nature Publishing Group.

Kornberg, R., et al., "Twenty-Five Year of the Nucleosome, Fundamental Particle of the Eukaryote Chromosome", Cell, 1999, pp. 285-294, vol. 98, Publisher: Cell Press.

Lakadamyali, M., et al., "Advanced microscopy methods for visualizing chromatin structure", FEBS Letters, 2015, pp. 3023-3030, vol. 589, Publisher: Elsevier.

Lee, H.M., et all., "Geometrical and Electronic Structures of Gold, Silver, and Gold—Silver Binary Clusters: Origins of Ductility of Gold and Gold-Silver Alloy Formation", J. Phys. Chem., 2003, pp. 9994-10005, vol. 107.

Lin, C-A, J., et al., "Synthesis, Characterization, and Bioconjugation of Fluorescent Gold Nanoclusters toward Biological Labeling Applications", ACS Nano, 2009, pp. 395-401, vol. 3, No. 2, Publisher: American Chemical Society.

Lu, Y., et al., "Application of Mass Spectrometry in the Synthesis and Characterization of Metal Nanoclusters", Analytical Chemistry, 2015, pp. 1-9, DOI: 10.1021/acs.analchem.5b00848, Publisher: ACS Publications.

Lucchini, R., et al., "Nucleosome positioning at the replication fork", The EMBO Journal, 2001, pp. 7294-7302, vol. 20, No. 24, Publisher: European Molecular Biology Organization.

(56) References Cited

OTHER PUBLICATIONS

Meyer-Almes, F.J., et al., "Mechanism of Intercalation into the DNA Double Helix by Ethidium", Biochemistry, 1993, pp. 4246-4253, vol. 32, Publisher: American Chemical Society.
Muslimovic, A., et al., "An optimized method for measurement of gamma-H2AX in blood mononuclear and cultured cells", Nature Protocols, 2008, pp. 1187-1193, vol. 3, No. 7, Publisher: Nature Publishing Group.
Neissa, J., et al., "Interaction of silver atomic quantum clusters with living organisms: bactericidal effect of Ag3 clusters mediated by disruption of topoisomerase-DNA complexes", Chemical Science, 2015, pp. 6717-6724, vol. 6, No. 12, Publisher: Royal Society of Chemistry.
Palermo, G., et al., "Fighting Cancer with Transition Metal Complexes: From Naked DNA to Protein and Chromatin Targeting Strategies", ChemMedChem, 2016, pp. 1199-1210, vol. 11, Publisher: Wiley Online Library.
Pang, B., et al., "Drug-induced histone eviction from open chromatin contributes to the chemotherapeutic effects of doxorubicin", "Nature Communications", 2013, DOI: 10.1038/ncomms2921, Publisher: Macmillan Publishers Limited.
Philip, R., et al., "Evolution of Nonlinear Optical Properties: From Gold Atomic Clusters to Plasmonic Nanocrystals", Nano Letters, 2012, pp. 4661-4667, vol. 12, Publisher: ACS Publications.
Pommier, Y., et al., "DNA Topoisomerases and Their Poisoning by Anticancer and Antibacterial Drugs", Chemistry & Biology, 2010, pp. 421-433, DOI 10.1016/j.chembiol.2010.04.012, vol. 17, Publisher: Elsevier.
Ramachandran, S., et al., "Transcriptional Regulators Compete with Nucleosomes Post-replication", Cell, 2016, pp. 1-13, vol. 165, Publisher: Elsevier.
Rao, S., et al., "Chromatin Remodeling, Measured by a Novel Real-Time Polymerase Chain Reaction Assay, Across the Proximal Promotor Region of the IL-2 Gene", The Journal of Immunology, 2001, pp. 4494-4503, vol. 167, doi: 10.4049/jimmunol. 167.8.4494, Publisher: The American Association of Immunologists.
Rhind, N., et al., "DNA Replication Timing", Cold Spring Harb. Perspect. Biol., 2013, pp. 1-26, a010132, vol. 5, Publisher: Cold Spring Harbor Library Press.
Ricci, M.A., et al., "Chromatin Fibers Are Formed by Heterogenous Groups of Nucleosomes In Vivo", Cell, 2015, pp. 1145-1158, vol. 160, Publisher: Elsevier.
Rust, , M., et al., "Sub-diffraction-limit imaging by stochastic optical reconstruction microscopy (STORM)", Nature Methods, 2006, pp. 793-795, vol. 3, No. 10, Publisher: Nature Publishing Group.
Schaaf, T.G., et al., "Giant Gold-Glutathione Cluster Compounds: Intense Optical Activity in Metal-Based Transitions", J. Phys. Chem. B, 2000, pp. 2630-2641, vol. 104, Publisher: American Chemical Society.
Skene, P., et al., "The nucleosomal barrier to promoter excape by RNA polymerase II is overcome by the chromatin remodeler Chd1", eLIFE, 2014, e02042, vol. 3, DOI: 10.7554/eLife.02042.
Walter, M., et al., "A unified view of ligand-protected gold clusters as superatom complexes", PNAS, Jul. 8, 2008, pp. 9157-9162, vol. 105, No. 27.
Yang, F., et al., "Doxorubicin Enhances Nucleosome Turnover around Promoters", Current Biology, 2013, pp. 782-787, vol. 23, Publisher: Elsevier.
Yang, F., et al., "Doxorubicin, DNA torsion, and chromatin dynamics", Biochimica et Biophysica Acta, 2014, pp. 84-89, vol. 1845, Publisher: Elsevier.
Zessin, P. J.M., et al., "Super-resolution fluorescence imaging of chromosomal DNA", Journal of Structural Biology, 2012, pp. 344-348, vol. 177, Publisher: Elsevier.
Attia, Y., et al., Supporting Information, including Materials and Methods, References, Figures S1-S20, and Tables S1-S4, pp. S1-S30, https://pubs.acs.org/doi/epdf/10.1021/ja410451m, Journal of the American Chemical Society, 2014, in support of Attia, Y., et al., "Structure-Directing and High-Efficiency Photocatalytic Hydrogen Production by Ag Clusters", Journal of the American Chemical Society, 2014, pp. 1182-1185, vol. 136, Publisher: ACS Publications.
Porto, V., et al., "Silver Atomic Quantum Clusters of Three Atoms for Cancer Therapy: Targeting Chromatin Compaction to Increase the Therapeutic Index of Chemotherapy", Advanced Materials, 2018, 30, 1801317, DOI: 10.1002/adma.201801317, Wiley-VCH Verlag Gmbh & Co. KGaA.
Porto, V., et al., Supporting Information, including Materials and Methods, Supporting Figures S1-S16, and References, pp. 1-28, Wiley Online Library, 2018, in support of Porto, V., et al., "Silver Atomic Quantum Clusters of Three Atoms for Cancer Therapy: Targeting Chromatin Compaction to Increase the Therapeutic Index of Chemotherapy", Advanced Materials, 2018, 30, 1801317, DOI: 10.1002/adma.201801317, Wiley-VCH Verlag GmbH & Co. KGaA.

* cited by examiner

METHODS OF PREPARING PURIFIED ATOMIC QUANTUM CLUSTERS

CROSS-REFERENCE TO RELATED APPLICATIONS

This application is a U.S. national phase under the provisions of 35 U.S.C. § 371 of International Patent Application No. PCT/ES19/70403 filed Jun. 11, 2019, which in turn claims priority under the provisions of 35 U.S.C. § 119 of European Patent Application No. 18177210.4 filed Jun. 12, 2018. The disclosures of such international patent application and European priority patent application are hereby incorporated herein by reference in their respective entireties, for all purposes.

FIELD OF THE INVENTION

The invention relates to methods of purifying atomic quantum clusters, purified compositions and uses of said compositions.

BACKGROUND OF THE INVENTION

The emergence of new methods for the synthesis and isolation of metal atomic quantum clusters (AQCs) has become promising for a wide range of biological, catalytic, electronic and optical applications. Additional advantages of these nanostructures can be found in their small size and relatively low toxicity, which makes them very attractive in different fields, such as biological labels and bioimaging.

Until very recently, the chemical synthesis of small naked metal clusters (i.e., AQCs that have a low number of atoms and are smaller than ~1 nm) without using strong binding ligands was considered to be practically impossible because these very small species were assumed to be highly reactive. However, those clusters have been shown to have an unexpectedly high stability owing to strong quantum confinement, which induces a HOMO-LUMO gap at the Fermi level. This gap increases as the cluster size decreases and, at the same time, the reactivity decreases, making clusters with only 2 atoms almost unreactive. The emergence of such a gap gives rise to markedly different geometric/electronic structures from bulk (or nano-) materials, which in turn provides clusters with new properties, including luminescence, catalysis, and others. Moreover, for small clusters (number of atoms less than about 15-20), large band gaps impart high resistance to oxidation. Therefore, the natural state of small clusters is uncharged.

EP1914196 describes processes of obtaining a family of zero-valent metal clusters, denominated AQCs. It was found that AQCs stop behaving in a "metallic" way and their behaviour becomes molecular in nature. Thus, new properties appear in these clusters that are not observed in nanoparticles, microparticles or bulk metal materials. This application describes a kinetic controlled method for producing stable AQCs in a range of sizes, e.g. from 2 to 27 atoms.

WO2012/059572 and EP2457572 describe a combination of at least one AQC and at least one antineoplastic drug for the prevention and/or treatment of a cell proliferative disorder. The application describes AQCs consisting of between 2 and 25 zero-valent transition metal atoms having a cytotoxic and anti-proliferative effect on cancer cell lines and therefore may be used in combination with antineoplastic agents to treat cell proliferative disorders.

Buceta et al., *Angew. Chemie Int. Ed.* 2015, 54: 7612 reported that silver clusters of three atoms (Ag3-AQCs) interact with double stranded DNA through intercalation. This intercalation is strictly dependent upon the number of atoms in the cluster and independent of the type of base pairs (AT of GC) of the double helix. However, the samples tested in Buceta et al. 2015 were not purified to ensure that only AQCs of less than 3 atoms were present. Larger silver clusters display huge catalytic activities for thiol oxidation resulting in cell demise. Therefore, it is desirable to obtain pure and highly concentrated AQCs with three atoms, without surfactants or other strong binding ligands that could mask their biological activity, which is a substantial challenge.

It is an object of the invention to provide purified compositions and methods of preparing purified compositions of AQCs.

SUMMARY OF THE INVENTION

In a first aspect, the invention provides a process of purifying atomic quantum clusters (AQCs) consisting of 3 or fewer zero-valent transition metal atoms comprising:

(i) applying a solution comprising a mixture of AQCs to a separation medium, wherein said separation medium either binds AQCs consisting of more than 3 zero-valent transition metal atoms, or binds AQCs consisting of 3 or fewer zero-valent transition metal atoms; and (ii) isolating AQCs consisting of 3 or fewer zero-valent transition metal atoms.

In another aspect, the invention provides a composition purified by the process described herein, which is substantially free of AQCs consisting of more than 3 zero-valent transition metal atoms.

In another aspect, the invention provides a composition comprising atomic quantum clusters (AQCs) consisting of 3 or fewer zero-valent transition metal atoms, which is substantially free of AQCs consisting of more than 3 zero-valent transition metal atoms.

In another aspect, the invention provides the composition described herein, in combination with an anti-proliferative agent for use in the treatment of a cell proliferative disorder.

In another aspect, the invention provides the composition described herein, optionally in combination with an anti-proliferative agent, for use in the prevention of lymph node metastasis of cancer.

In another aspect, the invention provides the composition described herein, in combination with an anti-proliferative agent, for use in the treatment of lymph node metastasis of cancer.

In another aspect, the invention provides the composition described herein, in combination with radiation therapy for use in the treatment of a cell proliferative disorder.

These and other aspects are described in more detail in the following description.

Figure 20:
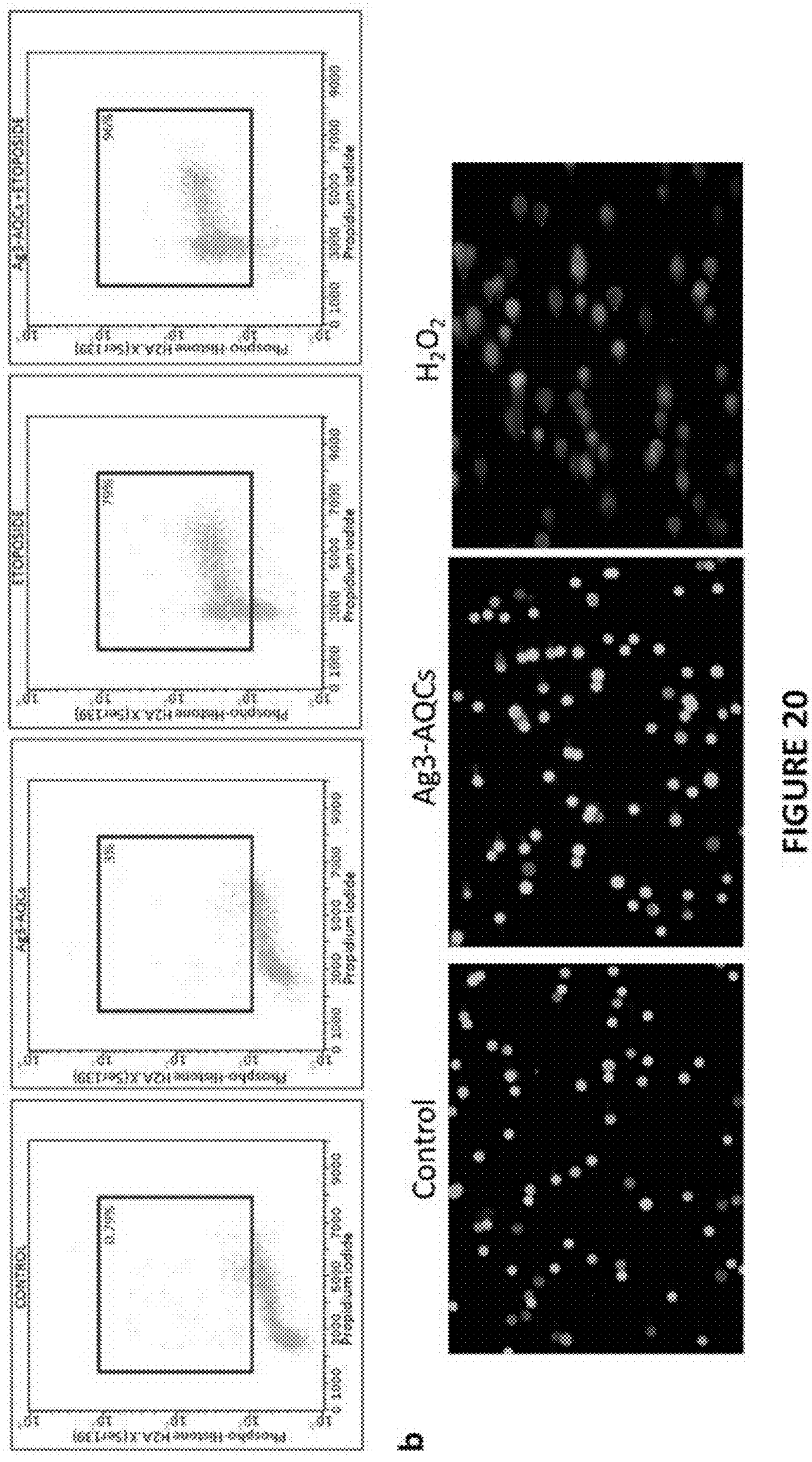

FIG. 20: Ag3-AQCs induce no DNA damage in A549 cells. (a) Flow cytometry measurement of gamma-H2AX phosphorylation after treatment with etoposide (12.5 μM) for 1 hour, Ag3-AQCs (83 ng/mL) for 30 minutes, or Ag3-AQCs (83 ng/mL) for 30 minutes followed by etoposide (12.5 μM) for 1 hour. Inset, positive cells, data represent mean±SD of 3 independent experiments, 3 replicas per experiment. (b) Comet assay of A549 cells after 1 hour of treatment with Ag3-AQCs (83 ng/mL) also show absence of DNA damage. $H_2O_2$ was included as a positive control.

Figure 21:
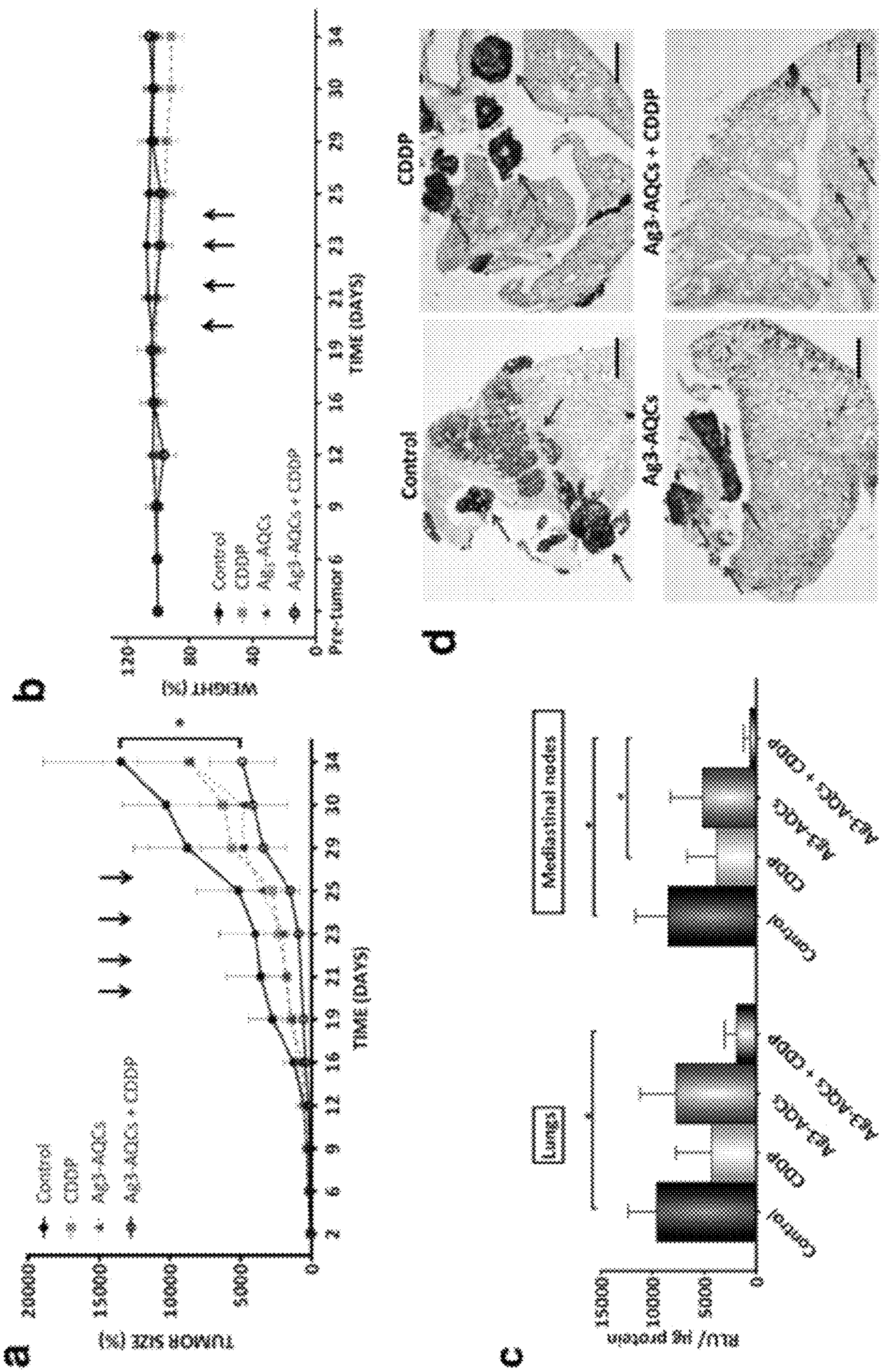

FIG. 21: Co-administration of Ag3-AQCs potentiates CDDP-mediated reduction of tumour growth and mediastinal lymph node invasion in mice with orthotopic lung cancer. (a) Tumour growth measured in vivo by luminescence (IVIS® Spectrum). Black arrows represent treatment administration times. (b) Mouse body weight over the entire experiment. (c) Quantification of tumour burden measured ex vivo in lung and mediastinal lymph nodes. (d) Immunohistochemical staining of mouse lungs using anti-CK7 antibody. Bar=300 μm.

Figure 22:
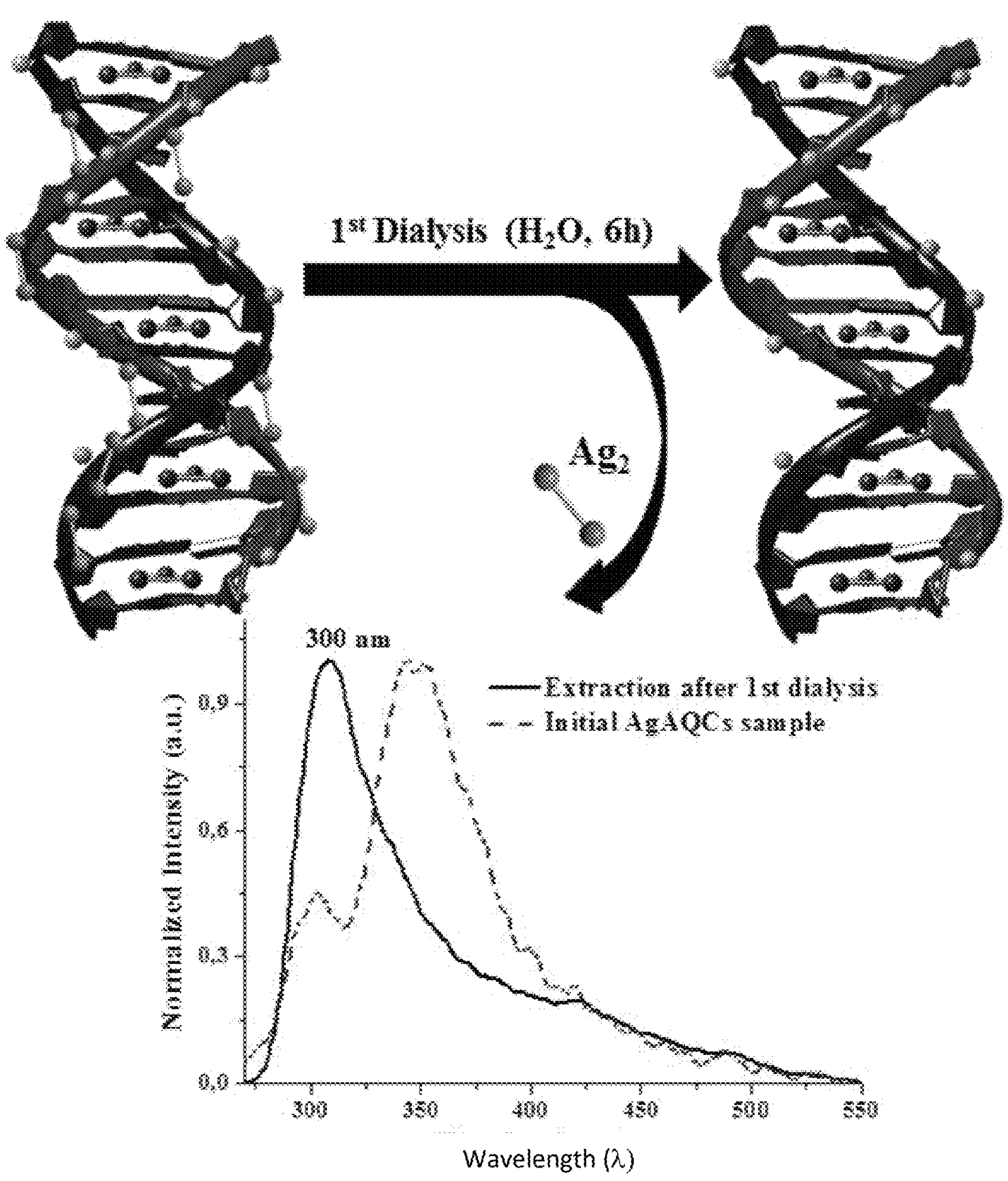

FIG. 22: Schematic representation and fluorescence spectrum of the cluster samples obtained after the first dialysis with DNA as the separation medium.

Figure 23:
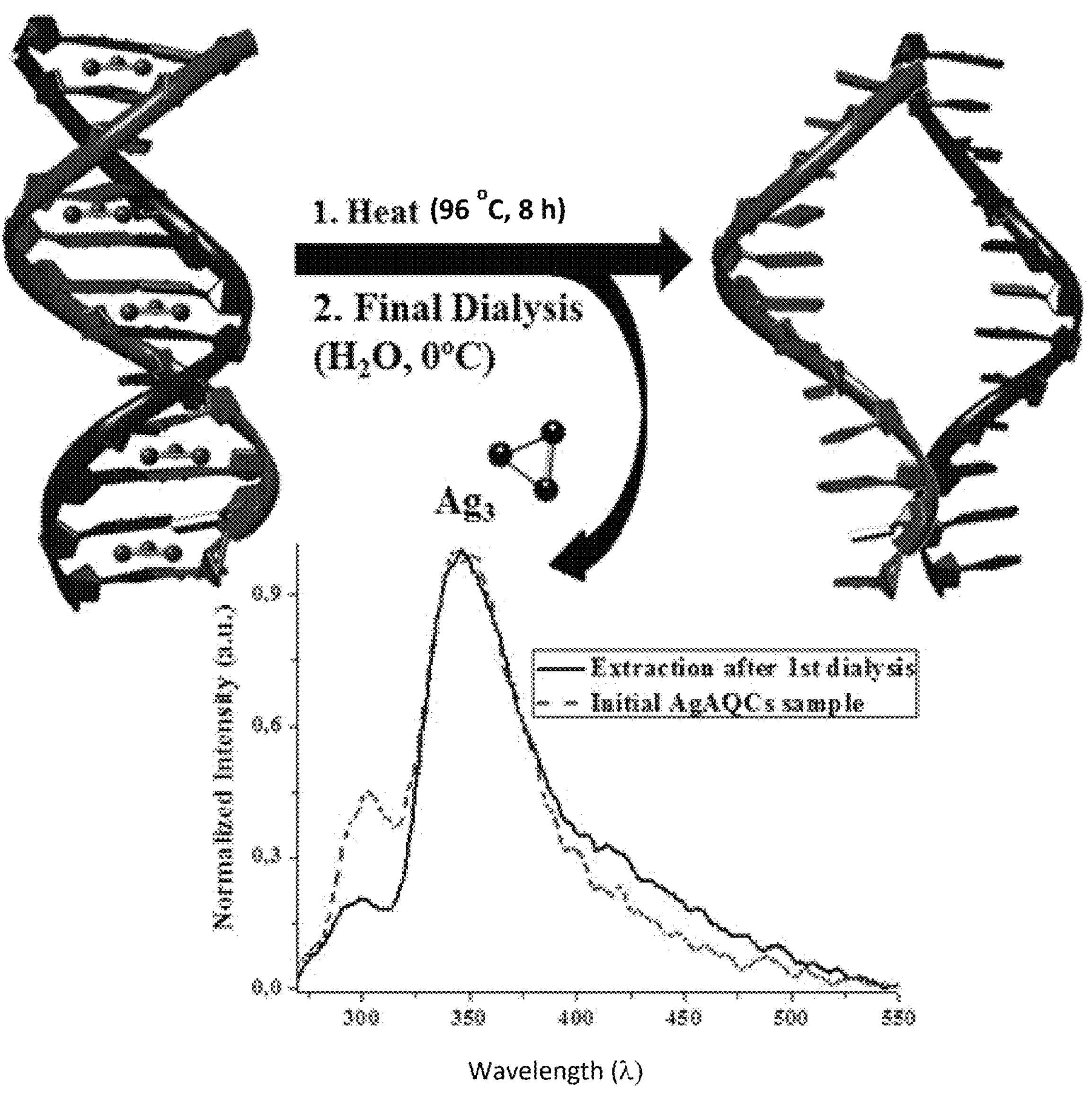

FIG. 23: Schematic representation and fluorescence spectrum of the cluster samples obtained after the final dialysis with DNA as the separation medium. DNA was denatured prior to this dialysis extraction step in order to release purified Ag3 clusters.

DETAILED DESCRIPTION OF THE INVENTION

Definitions

All technical and scientific terms used throughout the specification have the same meaning as those commonly understood by a person skilled in the art.

Throughout the specification, use of the term "about" with respect to any quantity is contemplated to include that quantity.

Throughout the specification, unless the context requires otherwise, the word "comprise", and variations such as "comprises" and "comprising", will be understood to imply the inclusion of a stated integer, step, group of integers or group of steps but not to the exclusion of any other integer, step, group of integers or group of steps.

Throughout the specification, unless the context requires otherwise, the term "consisting of", and variations such as "consists of", will be understood to imply the inclusion of a stated integer, step, group of integers or group of steps, with the exclusion of any other integer, step, group of integers or group of steps.

The term "atomic quantum clusters" or "AQCs" as used herein, refers to a group/cluster of 2 to 500 zero-valent transition metal atoms, such as between 2 to 200, 2 to 100, 2 to 50 or 2 to 25 transition metal atoms, and with a size less than 2 nm, such as less than 1 nm. The AQCs may comprise zero-valent transition metal atoms of identical (mononuclear clusters) or different (heteronuclear clusters) transition metals. It will be understood that this term does not include metal ions.

It will be understood that references to AQCs consisting of "more than 3" zero-valent transition metal atoms refer to AQCs comprising 4, 5, 6, 7, 8, 9, 10 or more zero-valent transition metal atoms (i.e. this term does not encompass AQCs with 3 metal atoms). This term can therefore be used interchangeably with "4 or more".

It will be understood that references to AQCs consisting of "3 or fewer" zero-valent transition metal atoms refer to AQCs with 2 or 3 transition metal zero-valent atoms. It will also be understood that references to AQCs consisting of "3" zero-valent transition metal atoms refer to AQCs with only 3 zero-valent transition metal atoms.

The term "transition metal" will be understood to refer to the elements of the periodic table known as transition metals, but it does not refer to the electrical behaviour of said elements. The confinement of electrons in the AQCs originates the quantum separation of the energy levels producing important changes in the properties of these materials, as reported in EP1914196. Thus, the metal atoms in the AQCs described herein can have a semiconductor-like or even insulating-like behaviour.

The term "substantially free of" may be used to refer to a composition which is mostly or completely free of an entity specifically mentioned thereafter (e.g. AQCs with more than 3 zero-valent transition metal atoms), or at least does not contain the entity in an amount such that the entity affects the efficacy, storability, usability regarding necessary safety concerns, and/or stability of the composition.

The term "purified" as used herein refers to compositions where substantially all AQCs consisting of the undesired number of zero-valent transition metal atoms have been removed. In particular, the methods described herein increase the degree of purity of the compositions by removing substantially all (preferably all) AQCs consisting of more than 3 zero-valent transition metal atoms.

References to the term "separation medium" refer to a material which has the ability to separate entities from a mixture. In the present application, the separation medium has the ability to selectively purify AQCs consisting of 3 or fewer zero-valent transition metal atoms from a mixture of AQCs containing larger clusters (i.e. 4 or more zero-valent transition metal atoms). Examples of such media are provided herein.

The term "thiol" will be understood to refer to a carbon-bonded sulfhydryl (R—SH) group (where R represents an alkyl or other organic substituent).

The term "aromatic group" is well known in the art and refers to a cyclic, planar molecule or moiety with (or comprising) a ring of resonance bonds. This includes benzene (i.e. $C_6H_6$) and derivatives thereof. Most aromatic groups are benzene derivatives. However, this term can also include heteroaromatic groups (i.e. one or more of the atoms in the aromatic ring is of an element other than carbon), for example, pyridine, pyrazine, pyrrole, imidazole, pyrazole, oxazole, thiophene, and their benzannulated analogues.

References to "DNA" (deoxyribonucleic acid) refer to molecules containing two polydeoxyribonucleotide strands substantially based paired and forming a double helix. The polynucleotide strands are composed of nucleotides each comprising a base, a sugar (deoxyribose), and a phosphate group. The nucleotides are joined to one another in a chain by covalent bonds between the sugar of one nucleotide and the phosphate group of the next, resulting in a sugar-phosphate backbone. Bases may comprise naturally occurring bases (i.e. cytosine [C], guanine [G], adenine [A] or thymine [T]) or non-naturally occurring bases. The bases of the two separate polynucleotide strands are bound together by hydrogen bonds according to base pairing rules (A with T and C with G) to make double-stranded DNA. This definition includes DNA which has been modified, e.g. to include non-naturally occurring bases or a modified backbone, provided that a double helix is formed so that 3 atom AQCs may intercalate.

Methods of Purification

According to an aspect of the invention, there is provided a process of purifying atomic quantum clusters (AQCs) consisting of 3 or fewer zero-valent transition metal atoms comprising:

(i) applying a solution comprising a mixture of AQCs to a separation medium, wherein said separation medium either binds AQCs consisting of more than 3 zero-valent transition metal atoms, or binds AQCs consisting of 3 or fewer zero-valent transition metal atoms; and (ii) isolating AQCs consisting of 3 or fewer zero-valent transition metal atoms.

The present invention provides a process of purifying atomic quantum clusters (AQCs) comprising applying a solution comprising a mixture of AQCs to a separation medium and isolating AQCs consisting of 3 or fewer zero-valent transition metal atoms. As will be described herein, investigations into the properties of AQCs consisting of 3 or fewer zero-valent transition metal atoms (in particular AQCs consisting of 3 zero-valent transition metal atoms) has highlighted a need to provide methods of purifying said clusters. Previously, AQCs were synthesised and separated by selective precipitation once the desired size of cluster is reached for example, see EP1914196. However, this method still results in the presence of a mixture of AQCs of different sizes, even if there is a predominant size cluster. Contamination of a composition with multiple sizes of AQCs can affect the behaviour and properties of the composition.

The present invention therefore provides a method of selectively purifying AQCs consisting of 3 or fewer zero-valent transition metal atoms.

In one embodiment, the separation medium binds AQCs consisting of more than 3 zero-valent transition metal atoms and the process comprises isolating the AQCs consisting of 3 or fewer zero-valent transition metal atoms from the unbound solution. References to the “unbound solution” refer to the solution containing components which are not bound to the separation medium. Examples of such separation media are provided herein. A skilled person would be able to determine if a separation medium is able to bind AQCs consisting of more than 3 zero-valent transition metal atoms using methods known in the art. For example, they could test the eluate after the sample is passed through the separation medium and determine the types of AQCs present in the eluate using fluorescence spectroscopy. Other characterization methods are described in the Examples which may be used in combination or as alternatives to fluorescence spectroscopy.

In one embodiment, the separation medium comprises a functional group which binds to AQCs consisting of more than 3 zero-valent transition metal atoms.

In one embodiment, the functional group is a thiol group. In a further embodiment, the separation medium comprises a thiolated resin, such as thiolated-silica.

Figure 1:
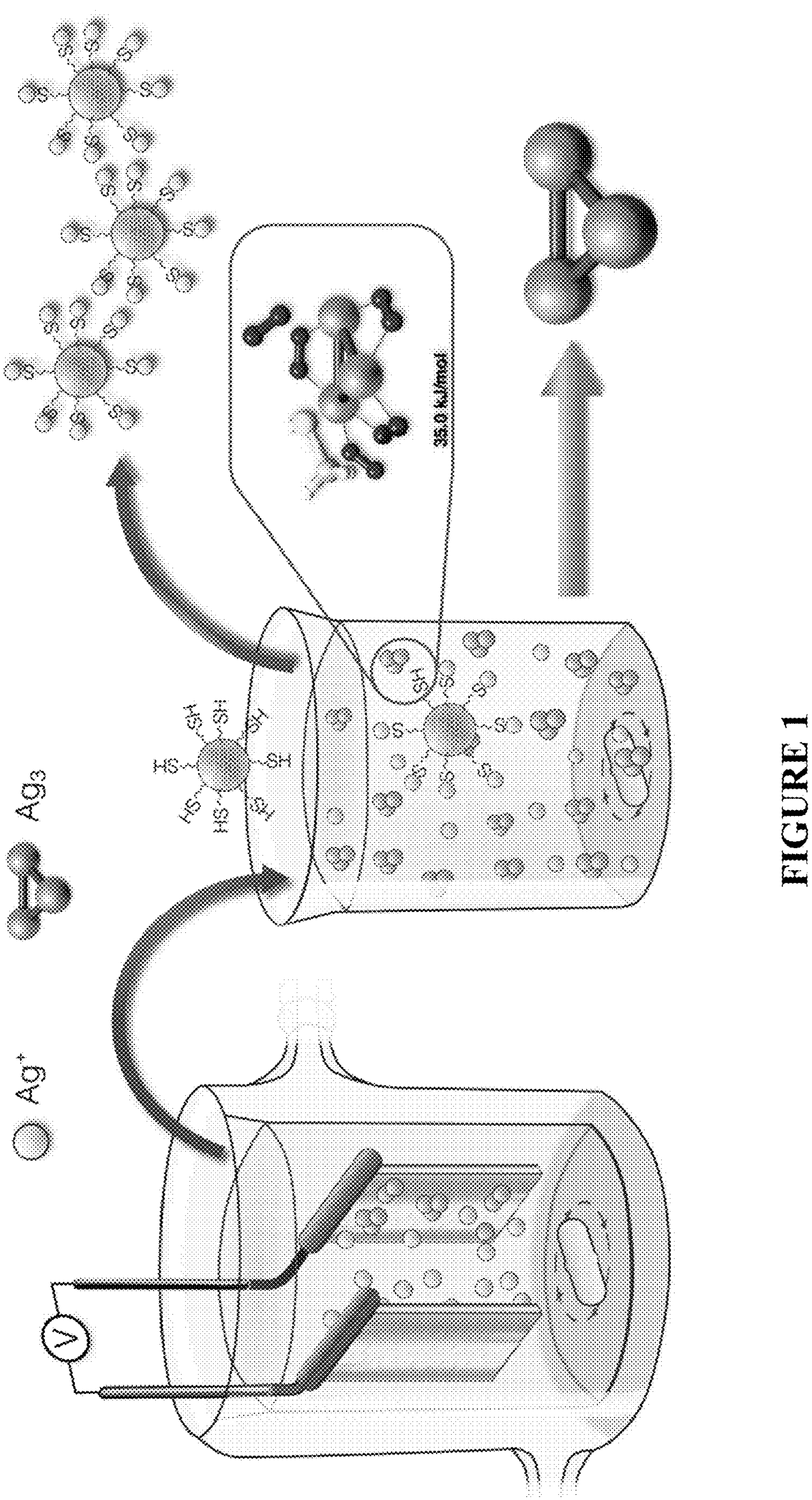
FIG. 1: Synthesis and purification of Ag3 clusters (Ag3-AQCs). Scheme of the electrochemical synthesis (left) and purification method, using a thiolated resin (right) for the production of Ag3-AQCs. Inset: DFT calculations showing that the interaction of Ag3-AQCs with thiols is energetically unfavourable.

Unexpectedly, it was found that Ag3-AQCs, unlike Ag ions, do not bind to thiols, therefore an efficient purification procedure has been established herein using a thiolated resin to selectively separate Ag ions from synthesised clusters (FIG. 1). Furthermore, it was also surprisingly found that clusters larger than Ag3-AQCs interact with the thiolated resins, therefore this purification procedure also guarantees the absence of contaminations with larger clusters.

Without being bound by theory, it appears that the amount of dissolved oxygen in aqueous Ag3-AQCs samples is sufficient to preclude the interaction of Ag3-AQCs with thiols, as observed in the inset of FIG. 1, where binding of methyl thiol to the Ag3-AQCs is not favourable (characterized by a positive binding energy). The only species besides Ag3-AQCs in the samples are Ag2-AQCs. However, as will be explained herein, such clusters are merely spectators because of their unreactivity. Furthermore, such Ag2-AQCs can be separated from Ag3-AQCs by the procedures described herein.

In one embodiment, the mixture of AQCs is present in an aqueous solution. In a further embodiment, the aqueous solution comprises dissolved oxygen, such as at least 2 times, or at least 3 times, the concentration of AQCs (in particular the concentration of AQCs consisting of 3 zero-valent transition metal atoms) present in the mixture.

In another aspect of the invention, the separation medium binds AQCs consisting of 3 or fewer zero-valent transition metal atoms and the process comprises discarding the AQCs consisting of more than 3 zero-valent transition metal atoms in the unbound solution, and isolating the AQCs consisting of 3 or fewer zero-valent transition metal atoms from the separation medium. In a further embodiment, the process comprises isolating by a process of treating (e.g. heating) the separation medium to release AQCs consisting of 3 or fewer zero-valent transition metal atoms.

In one embodiment, the separation medium comprises a functional group which binds to AQCs consisting of 3 or fewer zero-valent transition metal atoms.

Alternatively, in one embodiment, the separation medium comprises DNA. In a further embodiment, the separation medium comprises DNA that is substantially double stranded (i.e. so that a double helix is formed). The DNA may be completely double stranded (i.e. blunt ended) or substantially double stranded (i.e. when one or more of the nucleotides in the DNA is not present in a base pair, e.g. to form a single stranded sticky end).

Clusters of three metal atoms have been shown to interact with DNA through intercalation. This intercalation is strictly dependent upon the number of atoms in the cluster and independent of the type of base pairs (AT of GC) of the double helix. Therefore, it will be understood that the any polynucleotide sequence may be used for the DNA separation medium of the present invention. It will also be understood that the DNA in the separation medium is substantially double stranded and is of a sufficient length to form a double helix.

In one embodiment, the DNA is at least 10, 15, 20, 25, 30, 35, 40, 45, 50, 55, 60, 65, 70, 75, 80, 85, 90, 95 or 100 nucleotides in length. In one embodiment, the DNA is 15 or more, such as 20, 30, 40, 50, 60, 70, 80, 90, or 100 or more nucleotides long. It will be understood that these embodiments refer to the number of nucleotides in each strand of the double stranded DNA, although the number of nucleotides in each strand may be the same or different (e.g. if the DNA is substantially double stranded).

It will be understood that the size/length of DNA used will be sufficient to enable the use of DNA as a separation medium, i.e. so that it can be separated from AQCs consisting of more than 3 zero-valent transition metal atoms which remain unbound in solution and can be isolated from the said solution. For example, if said DNA is used in a dialysis method, the DNA is of a sufficient size so that it is prevented from passing through the semipermeable membrane of a dialysis device (this would depend upon the pore size of the membrane used). Therefore, in one embodiment, the molecular weight (MW) of the DNA is larger than the pore size of the semipermeable membrane used. For example, in one embodiment, the MW of the DNA is greater than 3.5 kDa, such as about 4 kDa or above. A person skilled in the art would know how to design and synthesise DNA of the appropriate length.

As shown in the Examples provided herein, DNA can be used to selectively purify AQCs consisting of 3 zero-valent metal atoms because this is the only size of cluster which intercalates into the DNA. Larger size clusters do not interact with the DNA and AQCs consisting of 2 zero-valent metal atoms can be easily washed away (e.g. dialysed away) because they are only loosely bound to the exterior of the DNA double helix.

Therefore, in one embodiment, the process comprises applying a wash solution to remove AQCs consisting of less than 3 zero-valent transition metal atoms (i.e. AQCs consisting of 2 zero-valent transition metal atoms), so that only AQCs consisting of 3 zero-valent transition metal atoms are bound by the separation medium.

In one embodiment, the process comprises isolating by a process comprising denaturing the DNA to release AQCs consisting of 3 zero-valent transition metal atoms. The process may additionally comprise applying a second wash solution to isolate the released AQCs consisting of 3 zero-valent transition metal atoms from the denatured DNA, for example by dialysis.

Methods of denaturing would be well known to a person skilled in the art, for example by applying heat or a chemical agent (such as formamide, guanidine, sodium salicylate, dimethyl sulfoxide (DMSO), propylene glycol, and urea). In one embodiment, the DNA is denatured by heating, for example to about 96° C. Once the DNA is denatured, a wash solution may be used to isolate the released AQCs consisting of 3 zero-valent transition metal atoms. If the DNA is used in a dialysis method, then it will be understood that this embodiment encompasses placing a dialysis device comprising the denatured DNA and AQCs consisting of 3 zero-valent transition metal atoms, in a wash solution and isolating the released AQCs consisting of 3 zero-valent transition metal atoms (which have passed into the wash solution).

Methods of Purifying AQCs Consisting of 3 Atoms

Once AQCs consisting of 3 or fewer zero-valent transition metal atoms have been isolated, it may be desirable to separate said AQCs in order to obtain solutions of AQCs consisting of either 2 or 3 zero-valent transition metal atoms. Therefore, in one embodiment, the process additionally comprises applying the isolated AQCs consisting of 3 or fewer zero-valent transition metal atoms to a second separation medium and isolating AQCs consisting of 3 zero-valent transition metal atoms. This enables AQCs consisting of 3 atoms to be separated from AQCs consisting of 2 atoms which do not bind to the second separation medium.

In one embodiment, the second separation medium binds AQCs consisting of 3 zero-valent transition metal atoms and the process comprises discarding the AQCs consisting of less than 3 zero-valent transition metal atoms (i.e. AQCs consisting of 2 zero-valent transition metal atoms) in the unbound solution, and isolating the AQCs consisting of 3 zero-valent transition metal atoms from the second separation medium. In a further embodiment, the process comprises isolating by a process of treating (e.g. heating) the second separation medium to release AQCs consisting of 3 zero-valent transition metal atoms.

In one embodiment, the second separation medium comprises a functional group which binds to AQCs consisting of 3 zero-valent transition metal atoms.

It has been discovered that in a mixture of AQCs comprising 2 and 3 metal atoms, AQCs of 3 metal atoms selectively bind aromatic groups, so that AQCs of 3 atoms can be separated from AQCs of 2 atoms. Therefore, in one embodiment, the functional group is an aromatic group, such as a cyclic and polycyclic aromatic group. Said aromatic group may additionally bear one or more substituents e.g. alkyl (such as methyl) groups, alkenyl (such as allyl) groups, halogen (e.g. chloro) groups etc.

In one embodiment, the aromatic group may comprise a benzene ring. Said benzene ring may be present in a polybenzene structure, for example: naphthalene (a fused pair of benzene rings); anthracene or phenanthrene (three fused benzene rings); tetracene, chrysene, triphenylene or pyrene (four fused benzene rings); pentaphene or benzo[a]pyrene (five fused benzene rings). In a particular embodiment, the aromatic group may comprise a pyrene ring. Furthermore, the benzene ring may comprise one or more additional substituents, for example: toluene or styrene (also known as ethenylbenzene, vinylbenzene, or phenylethane).

In one embodiment, the aromatic group may comprise a pyridine group. In a further embodiment, the aromatic group may be selected from the list consisting of benzene and pyridine.

The aromatic group may be part of a larger structure, which may be used in the second separation medium, for example graphene, carbon nanotubes, fullerenes or carbon quantum dots.

In an alternative embodiment, the second separation medium comprises double stranded DNA. As DNA may be used to purify AQCs consisting of 3 zero-valent transition metal atoms only, it will be understood that it may be used on its own as a separation medium or in conjunction with the processes described hereinbefore as a second separation medium. The latter option ensures that AQCs consisting of 3 zero-valent transition metal atoms may be purified. For example, the process may comprise: (i) applying a mixture of AQCs to a separation medium comprising a thiolated resin; (ii) collecting the unbound solution which comprises AQCs consisting of 3 or fewer zero-valent transition metal atoms; and (iii) applying this solution to a second/additional separation medium comprising double stranded DNA.

In one embodiment, AQCs consisting of 3 zero-valent transition metal atoms are isolated by heating the second separation medium to release AQCs consisting of 3 zero-valent transition metal atoms and applying a wash solution to isolate the released AQCs consisting of 3 zero-valent transition metal atoms from the second separation medium, for example by chromatography or dialysis. For example, the second separation medium can be heated to about 100° C. in order to release AQCs consisting of 3 zero-valent transition metal atoms. A wash solution may then be used to isolate the released AQCs consisting of 3 zero-valent transition metal atoms.

It will be understood that one or more of the purification methods disclosed herein may be repeated one or more times. Conducting the purification method multiple times can increase the purification of the sample and allow the desired purification to be achieved.

Chromatography and Dialysis

In one embodiment, the separation medium is used in a chromatographic method. Chromatography is a method used to separate a mixture by passing a mobile phase comprising the mixture, through a stationary phase (e.g. comprising the separation medium described herein). The mixture is separated based on how the constituents of the mobile phase interact with the stationary phase. It will be understood that if the separation medium retains AQCs consisting of more than 3 zero-valent transition metal atoms, then the eluate (which comprises AQCs consisting of 3 or fewer zero-valent transition metal atoms) is collected. Alternatively, if the separation medium retains AQCs consisting of 3 or fewer zero-valent transition metal atoms, then the eluate (which comprises AQCs consisting of more than 3 zero-valent transition metal atoms) is discarded. In one embodiment, the separation medium is present in a chromatography column. Such chromatography columns are commercially available. The chromatography column may be used as part of a variety of chromatography methods which include, for example, high performance liquid chromatography (HPLC).

In one embodiment, the process is a chromatographic method wherein the separation medium is the solid phase and the solution comprising a mixture of AQCs is the mobile phase. In a further embodiment, the AQCs consisting of more than 3 zero-valent transition metal atoms are bound by the solid phase and the AQCs consisting of 3 or fewer zero-valent transition metal atoms are isolated from the mobile phase. In an alternative embodiment, the AQCs consisting of 3 or fewer zero-valent transition metal atoms are bound and then isolated from the solid phase. In this embodiment, the mobile phase comprising the AQCs consisting of more than 3 zero-valent transition metal atoms is discarded, before the separation medium is treated (e.g. heated) to release the AQCs consisting of 3 or fewer zero-valent transition metal atoms and a second mobile phase, e.g. a wash solution, is applied to the separation medium to isolate the released AQCs consisting of 3 or fewer zero-valent transition metal atoms.

In one embodiment, the separation medium is used in a dialysis method. Dialysis is a method of separating molecules based on their rates of diffusion through a semipermeable membrane. For example, the solution comprising a mixture of AQCs could be applied to a separation medium and then placed in a dialysis device (e.g. a dialysis cassette or dialysis tubing). Such dialysis cassettes, tubing or devices are commercially available. Dialysis membranes may be chosen with a molecular weight cut-off chosen according to the requirements of the separation (e.g. according to the molecular weight of the DNA used in the separation medium).

Therefore, in one embodiment, the process comprises applying a solution comprising a mixture of AQCs to a separation medium and then placing the mixture in a dialysis device comprising a semipermeable membrane, e.g. a 3.5 KDa membrane. Said semipermeable membrane prevents passage of the separation media and anything bound thereto. It will be understood that if the separation medium binds to AQCs consisting of more than 3 zero-valent transition metal atoms, then the solution which passes through the semipermeable membrane (which comprises AQCs consisting of 3 or fewer zero-valent transition metal atoms) is isolated. Alternatively, if the separation medium binds to AQCs consisting of 3 or fewer zero-valent transition metal atoms, then the solution which passes through the semipermeable membrane (which comprises AQCs consisting of more than 3 zero-valent transition metal atoms) is discarded.

Atomic Quantum Clusters (AQCs)

In one embodiment, the metal atoms are selected from silver (Ag), gold (Au), copper (Cu), platinum (Pt), iron (Fe), chromium (Cr), palladium (Pd), nickel (Ni), rhodium (Rh), lead (Pb), iridium (Ir), ruthenium (Ru), osmium (Os), cobalt (Co), titanium (Ti), vanadium (V) or any combination thereof. In a further embodiment, the metal atoms are selected from Ag, Au, Cu, Pt or any combination thereof. In a yet further embodiment, the metal atoms are Ag.

The AQCs described herein are stable, i.e. they conserve the number of atoms, and therefore their properties, overtime, so that they can be isolated and manipulated like any other chemical compound. The AQCs can be conserved for months, even years, without the need of an external stabilizer.

The mixture of AQCs may be synthesised by a variety of methods known in the art, for example those described in EP1914196 or Buceta et al. 2015, which are herein incorporated by reference.

The mixture may also be synthesised using the method described herein in Example 1. More specifically, there is provided a method of synthesising silver AQCs which comprises conducting the method in a three-electrode electrochemical cell comprising a hydrogen electrode as a reference electrode and two silver electrodes as the counter and working electrode, wherein the silver electrodes comprise a surface area which is greater than 5 $cm^2$, such as greater than 10 $cm^2$, for example about 17 $cm^2$, and wherein a constant voltage which is greater than 4V, such as about 6V, is applied at about 25° C. for at least 3,000 seconds, for example about 3,600 seconds. The silver electrodes may be polished prior to synthesis, for example using sandpaper and/or alumina. The method may be conducted in purified, deaerated water, such as deaerated MilliQ water. Optionally, any excess $Ag^+$ ions may be removed by the addition of NaCl and subsequent precipitation and filtration.

References to AQCs used herein, include those in the form of a hydrate, i.e. they have water molecules attached to the cluster via non-covalent bonding.

Compositions

According to an aspect of the invention, there is provided a composition purified by a process as described herein, which is substantially free of AQCs consisting of more than 3 zero-valent transition metal atoms.

The potential therapeutic uses of compositions comprising AQCs consisting of 3 or fewer zero-valent transition metal atoms will be described herein. It has been found that such compositions have no cytotoxic effect on eukaryotic cells on their own, but provide a surprising synergistic effect when combined with DNA acting drugs. This mechanism is unique to clusters of this size. Therefore, this application provides, for the first time, the motivation to purify AQCs so that the composition consists of only AQCs with 3 or fewer zero-valent transition metal atoms. Even though compositions comprising AQCs of small size have previously been synthesised, for example see Buceta et al. 2015, the reports indicate that they were not purified prior to analysis. Therefore, these unique properties were masked due to the presence of AQCs with larger clusters. The compositions of the invention provide purer compositions than those previously described and therefore have the distinct property of having no cytotoxic effect on eukaryotic cells when administered on their own (e.g. see Example 8).

Therefore, according to an aspect of the invention, there is provided a composition comprising atomic quantum clusters (AQCs) consisting of 3 or fewer zero-valent transition metal atoms, which is substantially free of AQCs consisting of more than 3 zero-valent transition metal atoms.

In this embodiment of the invention, the composition is substantially free of AQCs consisting of more than 3 zero-valent transition metal atoms, e.g. the composition may contain less than about 10 mol % (molar percentage based on the total AQC content of the composition), such as less than about 7 mol %, less than about 5 mol %, less than about 2 mol %, less than about 1 mol % or less than about 0.5 mol % of AQCs consisting of more than 3 zero-valent transition metal atoms.

In one embodiment, the composition is substantially free of AQCs consisting of 2 zero-valent transition metal atoms. As shown by the methods described herein, the isolation of AQCs consisting of 3 zero-valent transition metal atoms can be achieved, for example, using DNA as a separation medium. The compositions described herein may be referred to as purified compositions.

In this embodiment of the invention, the composition is substantially free of AQCs consisting of 2 zero-valent transition metal atoms, e.g. the composition may contain less than about 10 mol % (molar percentage based on the total AQC content of the composition), such as less than about 7 mol %, less than about 5 mol %, less than about 2 mol %, less than about 1 mol % or less than about 0.5 mol % of AQCs consisting of 2 zero-valent transition metal atoms.

In a composition which is substantially free of AQCs consisting of more than 3 and 2 zero-valent transition metal atoms (i.e. the composition essentially consists of AQCs consisting of 3 zero-valent transition metal atoms), the composition may contain less than about 10 mol % (molar percentage based on the total AQC content of the composition), such as less than about less than about 7 mol %, less than about 5 mol %, less than about 2 mol %, less than about 1 mol % or less than about 0.5 mol % of AQCs consisting of more than 3 and 2 zero-valent transition metal atoms.

A property of a composition that can be considered "substantially free of AQCs consisting of more than 3 zero-valent transition metal atoms", is that it has no cytotoxic effect when administered on its own, i.e. not in the presence of an anti-proliferative agent and/or when AQCs with larger clusters are present. This property may be used to identify such compositions.

In one embodiment, the composition is substantially free of metal ions. Metal ions are frequently a by-product during the synthesis of AQCs. These can be removed using, for example, NaCl or the purification methods described herein. It will be understood that the reference to metal ions is with respect to ions of the transition metal contained in the AQCs.

In one embodiment, the composition contains less than about 20 mol %, such as less than about 15 mol %, 10 mol %, 5 mol %, 2 mol %, 1 mol % or 0.5 mol % of metal ions (i.e. free ions of the transition metal used to synthesise the AQCs).

Uses of Compositions

The novel purification approaches discussed herein allowed a high enough amount of 3 atom metal AQCs to be obtained in order to explore the action of these AQCs on chromatin, in particular in human lung and breast adenocarcinoma and glioblastoma cell lines, and in cancer-bearing mice.

Targeting of DNA has been proven to cause relatively potent and selective destruction of tumour cells (Cheung-Ong et al. Chem. Biol. 2013, 20: 648 and Gurova, *Future Oncol.* 2009, 5: 1685). However, resistance mechanisms hamper their effectiveness; for instance, a sufficient amount of cisplatin (CDDP) may fail to reach the DNA (Kelland, *Nat. Rev. Cancer.* 2007, 7: 573). It has now been found that the co-administration of CDDP with Ag3-AQCs increases not only the amount of CDDP bound to DNA but also CDDP cytotoxicity. Given the differential effect that Ag3-AQCs present between the tumour and healthy tissue, co-administration of Ag3-AQCs increases the therapeutic index of chemotherapy. These results thus underscore the importance of targeting chromatin compaction to increase the efficacy of chemotherapeutic drugs (Davey et al. *Nature Comm.* 2017, 8, 1575, and Palermo et al. *Chem. Med. Chem.* 2016 11: 1199). Together, these findings establish the therapeutic potential of clusters, a goal that also depends upon the development of efficient synthetic procedures capable of providing precise size control at the lowest scale of nanomaterials.

Therefore, according to an aspect of the invention, there is provided the composition as described herein, in combination with an anti-proliferative agent for use in the treatment of a cell proliferative disorder.

As described herein, AQCs consisting of 3 or fewer zero-valent transition metal atoms do not have cytostatic or cytotoxic properties of their own in eukaryotic cells. This is in contradiction to the teaching of WO2012/059572 and EP2457572 (see Example 3 and Example 4 of WO2012/059572 and EP2457572) and indicates that the material described in that document as Ag3 was not purified Ag3 and must have contained other biologically active contaminants. However, when purified AQCs consisting of 3 zero-valent transition metal atoms are administered in combination with an anti-proliferative agent, in particular DNA binding agents, there is a surprising synergistic effect. Without being bound by theory, this surprising synergy is thought to be due, at least in part, to the unique mechanism of action shown by AQCs of 3 atoms. Furthermore, this effect was shown to only be enhanced in proliferating cells, and therefore can selectively target cells with abnormal proliferation affected by the proliferative disorder.

References to a "cell proliferative disorder" refer to a disorder resulting in the new, abnormal growth of cells or a growth of abnormal cells without physiological control. This can result in an unstructured mass, i.e. a tumour. In one embodiment, the cell proliferative disorder is a tumour and/or cancer.

Cancers may include, but are not limited to: spleen, colorectal and/or colon cancer, colon carcinomas, ovarian carcinomas, ovarian cancer, breast cancer, carcinomas of the uterus, lung cancer, stomach cancer, oesophageal cancer, liver cancer, carcinomas of the pancreas, kidney cancer, bladder cancer, prostate cancer, testicular cancer, bone cancer, skin cancer, sarcoma, Kaposi sarcomas, brain tumours, myosarcomas, neuroblastomas, lymphomas and leukaemias, melanoma, glioma, medulloblastoma and head and neck carcinoma. In one embodiment, the cancer is selected from lung, breast, colon or brain cancer (in particular glioblastoma). In a further embodiment, the cancer is brain cancer, such as glioblastoma.

According to an aspect of the invention, there is provided the composition as described herein, optionally in combination with an anti-proliferative agent, for use in the prevention of lymph node metastasis of cancer. According to another aspect of the invention, there is provided the composition as described herein, in combination with an anti-proliferative agent, for use in the treatment of lymph node metastasis of cancer.

In a further embodiment, the lymph node is a mediastinal node. Said mediastinal nodes are a group of lymph nodes located in the thoracic cavity of the body.

Preventing metastasis of cancer is a key part of cancer treatment to prevent secondary cancers and relapse. As shown in the results presented herein, administration of Ag3-AQCs is able to reduce tumour burden in the mediastinal nodes. Furthermore, administration of cisplatin with Ag3-AQCs was significantly more efficient in decreasing lymphatic node invasion than cisplatin alone (see Example 17 and FIG. 21). Therefore, it has been surprisingly found that the compositions of the invention have an additional beneficial effect of treating and preventing lymph node metastasis of cancer.

In one embodiment, the anti-proliferative agent is selected from DNA binding drugs, DNA intercalating drugs, alkylating agents and nucleoside analogues. The anti-proliferative agent is one which acts to inhibit or suppress cellular growth, multiplication and proliferation. They normally act by killing cells that divide rapidly, i.e. those which are affected by the cell proliferative disorder.

DNA binding cytotoxic drugs are the first choice in the treatment of many cancers. A major factor in the resistance of chemotherapy is that an insufficient amount of drug may reach the DNA, and chromatin is a major barrier that limits accessibility to DNA. Up to now, largely due to the lack of agents that can act on chromatin without other coupled effects, the importance of chromatin compaction affecting the action of chemotherapeutic DNA binding drugs could not be assessed. Using uncharged metal clusters of only 3 atoms, the present application provides evidence of the significance of targeting chromatin compaction to increase the therapeutic index of chemotherapy.

In one embodiment, the anti-proliferative agent is DNA binding agent, such as cisplatin, oxaliplatin, carboplatin, carmustine or doxorubicin. In a further embodiment, the anti-proliferative agent is cisplatin. In an alternative embodiment, the anti-proliferative agent is not cisplatin.

In one embodiment, the anti-proliferative agent is a nucleoside analogue, such as gemcitabine.

The compositions of the invention may be administered with multiple anti-proliferative agents, such as at least one, for example two, three, four or more anti-proliferative agents.

In one embodiment, the composition and anti-proliferative agent are administered simultaneously. In this embodiment, the two agents are administered at the same time or at substantially the same time. They may also be administered by the same route and, optionally, in the same composition. Alternatively, they may be administered by different routes, i.e. separately, but at the same time or at substantially the same time.

In an alternative embodiment, the composition and anti-proliferative agent are administered sequentially. In this embodiment, the two agents are administered at different times so that one of the agents is administered before the second agent. They may be administered by the same or different routes.

In one embodiment, the composition is administered before the anti-proliferative agent. Without being bound by theory, the AQCs in the composition are thought to induce chromatin decompaction which increases the efficacy of the anti-proliferative agent once administered. Therefore, if the agents are administered separately, the anti-proliferative agent is administered while the composition is still effective, i.e. the composition and the anti-proliferative agent are administered within a timeframe that will exert a synergistic effect upon administration to a patient.

In a further embodiment, the composition is administered not more than about 1, 2, 3, 4, 5, 6, 7, 8, 9, 10, 11, 12, 13, 14, 15, 16, 17, 18, 19, 20, 21, 22, 23 or 24 hours before the anti-proliferative agent. In a particular embodiment, the composition is administered about 15, 20, 30 or 45 minutes or 1, 2, 3, 4, 5, 6, 7, 8, 9, 10, 11, 12, 13, 14, 15, 16, 17, 18, 19, 20, 21, 22, 23 or 24 hours before the anti-proliferative agent.

In one embodiment, the composition is administered between 0 and 24 hours, such as between 0 and 20 hours, 0 and 10 hours, 0 and 6 hours, 0 and 4 hours, 0 and 2 hours or 0 and 1 hour, before the anti-proliferative agent. This embodiment includes simultaneous (i.e. 0 hours) and sequential administration.

In one embodiment, the composition and anti-proliferative agent are present in such a weight ratio that the resulting composition will exert a synergistic effect upon administration to a patient. Suitable weight ratios can be determined by methods well known to those skilled in the art.

According to an aspect of the invention, there is provided the composition as described herein, in combination with radiation therapy for use in the treatment of a cell proliferative disorder, such as cancer. Thus, in an embodiment, a composition of the invention comprising AQCs consisting of three or fewer zero-valent transition metal atoms which is substantially free of AQCs consisting of more than 3 zero-valent transition metal atoms, and which may optionally be combined with an anti-proliferative agent, is used in combination with radiation therapy.

As described herein, the compositions of the invention have the ability to intercalate into the DNA and result in chromatin de-compaction. This can therefore be used to increase the susceptibility of treated cells to radiation and thus improve the effectiveness of radiation therapy.

Radiation therapy (also referred to as radiotherapy) uses high doses of radiation to damage cellular DNA and therefore kill cancer cells and shrink tumours. Such therapy may be in the form of an external beam or as internal radiation therapy. The choice of radiation therapy can depend on the type of cancer, size of the tumour, tumour location and well as other factors, such as the age, general health and medical history of the patient and the other types of cancer treatment used.

In one embodiment, the composition and radiation therapy are applied simultaneously. In an alternative embodiment, the composition and radiation therapy are applied sequentially.

In one embodiment, the compositions of the invention are able to improve the efficacy of an anti-proliferative agent or radiation therapy at least two-fold, such as three-fold, compared to the efficacy of the anti-proliferative agent or radiation therapy for the treatment of the disorder alone.

According to an aspect of the invention, there is provided a pharmaceutical composition comprising the compositions as described herein. The pharmaceutical composition may additionally comprise an anti-proliferative agent (e.g. if they are to be administered simultaneously). If both agents are present in the pharmaceutical composition, they may be in the form of a mixture or spatially separated from one another, either forming part of the same dosage form or as a kit of parts.

The compositions, and combinations where appropriate, may be formulated as a pharmaceutical composition, optionally comprising a pharmaceutically acceptable excipient, diluent or carrier. Examples of pharmaceutically acceptable carriers can include one or more of water, saline, phosphate buffered saline, dextrose, glycerol, ethanol and the like, as well as combinations thereof. Suitable pharmaceutical carriers, excipients or diluents are described in "Remington's Pharmaceutical Sciences" by E. W. Martin. Pharmaceutically acceptable carriers may further comprise minor amounts of auxiliary substances such as wetting or emulsifying agents, preservatives or buffers, which enhance the shelf life or effectiveness of the compositions of the invention. Pharmaceutical compositions may also include anti-adherents, binders, coatings, disintegrants, flavours, colours, lubricants, sorbents, preservatives, sweeteners, freeze dry excipients (including lyoprotectants) or compression aids.

Pharmaceutical compositions of the invention may be administered in a plurality of pharmaceutical forms of administrations, e.g. solid (such as tablets, pills, capsules, granules etc.) or liquid (such as solutions, suspensions, syrups, ointments, creams, gels or emulsions).

Pharmaceutical compositions of the invention can comprise a therapeutically effective amount. The therapeutically effective amount (i.e. the amount that produces an effect to help heal or cure the disorder to be treated) that may be administered to a subject will depend on multiple factors, such as the disease state, the age, sex, and weight of the individual, and the ability of the pharmaceutical composition to elicit a desired response in the individual. A therapeutically effective amount is also one in which any toxic or detrimental effects of the pharmaceutical composition of the invention, are outweighed by the therapeutically beneficial effects.

According to an aspect of the invention, there is provided the use of the composition as described herein, in combination with an anti-proliferative agent for the treatment of a cell proliferative disorder.

According to an aspect of the invention, there is provided the use of the composition as described herein, in combination with an anti-proliferative agent to treat lymph node metastasis of cancer. According to another aspect of the invention, there is provided the use of the composition as described herein, optionally in combination with an anti-proliferative agent, to prevent lymph node metastasis of cancer.

According to an aspect of the invention, there is provided the use of the composition as described herein, in combination with radiation therapy for the treatment of a cell proliferative disorder.

According to an aspect of the invention, there is provided the use of a composition as described herein, in the manufacture of a medicament for the treatment of a cell proliferative disorder. Optionally, the composition may be used in combination with an anti-proliferative agent and/or radiation.

Methods of Treatment

According to an aspect of the invention, there is provided a method of treating a patient with a cell proliferative disorder comprising administering a composition as described herein, in combination with an anti-proliferative agent and/or radiation therapy. The embodiments described hereinbefore for the compositions may be applied to said method of treatment (e.g. timing of administration, formulation of composition, etc.).

According to an aspect of the invention, there is provided a method of preventing lymph node metastasis of cancer comprising administering a composition as described herein, optionally in combination with an anti-proliferative agent and/or radiation therapy. According to another aspect of the invention, there is provided a method of treating lymph node metastasis of cancer comprising administering a composition as described herein, in combination with an anti-proliferative agent and/or radiation therapy.

The patient may be any subject suffering from the disorder. In one embodiment, the patient is a mammal. In a further embodiment, the mammal is selected from a human or a mouse.

In one embodiment, the composition (and optionally the anti-proliferative agent) is administered by any suitable mode of delivery, such as intravenously, intraarterially, intracardially, intracutaneously, subcutaneously, transdermally, interperitoneally, intramuscularly, orally, lingually, sublingually, buccally, intrarectally or by enema.

A topical application is also possible (e.g. for the treatment of melanomas). A particular form of topical application consists of introducing the composition (and optionally the anti-proliferative agent) into a carrier system, in particular a drug delivery system, and implanting said carrier system into the cancerous tissues, wherein said carrier system then release said composition (and optionally the agent) specifically at the site of the cancerous tissue. In this way it is possible to avoid side effects, as may occur in the case of systemic administration, i.e. to reduce the overall strain on the body.

Kits

According to an aspect of the invention, there is provided a kit comprising the separation medium described herein for use in a method of purifying a mixture of AQCs (i.e. in order to isolate AQCs consisting of 3 or fewer zero-valent transition metal atoms), optionally comprising instructions to use said kit in accordance with the purification methods described herein.

According to an aspect of the invention, there is provided a kit-of-parts comprising: (i) the composition and (ii) an anti-proliferative agent. Both components (i) and (ii) may be in admixture with a pharmaceutically acceptable adjuvant, diluent or carrier. The kit according to this aspect of the invention may be used in the treatment of a cell proliferative disorder.

The invention will now be exemplified in the following, non-limiting examples.

Abbreviations

All units used herein are to be understood with their standard definition known in the art (unless specified otherwise), including with the recognised prefixes, for example 'k' meaning kilo, 'm' meaning milli, 'p' meaning micro and 'n' meaning nano.

A549 Human lung adenocarcinoma cell line
AFM Atomic force microscopy
Ag Silver
Ag2 2 Silver atoms
Ag3 3 Silver atoms
$AgNO_3$ Silver nitrate
ANOVA Analysis of variance
AQC Atomic quantum cluster
ATP Adenosine triphosphate
Au Gold
BCNU Carmustine
BSA Bovine serum albumin
CBDCA Carboplatin
CD Circular dichroism
CDDP Cisplatin
$CO_2$ Carbon dioxide
DFT Density functional theory
DMSO Dimethyl sulfoxide
DNA Deoxyribonucleic acid
DOX Doxorubicin DTT Dithiothreitol
EAd Adsorption energy
EB Ethidium bromide
EDTA Ethylenediaminetetraacetic acid
EdU 5-Ethynyl-2'-deoxyuridine
EGTA Ethylene glycol-bis(β-aminoethyl ether)-N,N,N',N'-tetraacetic acid
ESI Electrospray ionization mass spectrometry
ESI-TOF Electrospray ionization time-of-flight mass spectrometry
FBS Fetal bovine serum
FDR False discovery rate
FITC Fluorescein isothiocyanate
FWHM Full width at half maximum
GAPDH Glyceraldehyde 3-phosphate dehydrogenase
GEM Gemcitabine
$H_2O_2$ Hydrogen peroxide
HCl Hydrochloride
HEPES 4-(2-hydroxyethyl)-1-piperazineethanesulfonic acid
HOMO Highest occupied molecular orbital
$HNO_3$ Nitric acid
IC Inhibitory concentration
ICP-MS Inductively coupled plasma mass spectrometry
IHC Immunohistochemical
IP Propidium iodide
ITC Isothermal titration calorimetry
KCl Potassium chloride
KOH Potassium hydroxide
Luc North American Firefly Luciferase gene
LUMO Lowest unoccupied molecular orbital
MCF7 Human breast adenocarcinoma cell line
MeSH Methylthiol
$MgCl_2$ Magnesium chloride
$N_2$ Nitrogen
NaF Sodium fluoride
$NH_4Cl$ Ammonium chloride
$O_2$ Oxygen
OXA Oxaliplatin
PBS Phosphate buffered saline
pH2AX Phosphorylated histone H2AX
PMSF Phenylmethane sulfonyl fluoride
Pt Platinum
qPCR Real-time polymerase chain reaction
RIN RNA Integrity Number
RLU Relative luminescence units
RNA Ribonucleic acid
RT Room temperature
SDS Sodium dodecyl sulphate
SDS-PAGE Sodium dodecyl sulphate-polyacrylamide gel electrophoresis
STORM Stochastic optical reconstruction microscopy
TAE Tris/Acetic acid/EDTA buffer solution
TBE Tris/Borate/EDTA buffer solution
TE Tris/EDTA buffer solution
Topo I Human topoisomerase I
Topo II Human topoisomerase 11
Tris Tris(hydroxymethyl)aminomethane
U Enzyme unit
U87 Human glioblastoma multiform cell line
UV-vis Ultraviolet-visible spectroscopy

Materials and Methods

Unless otherwise specified, all reagents were purchased from Sigma Aldrich, Co., Spain. Silver sheets (99%) were purchased from Goodfellow Cambridge Ltd., Huntingdon, UK. Alumina nanoparticles (average size≈50 nm) and cloth pads were purchased from Buehler, Düsseldorf, Germany.

Sandpaper (1,000 grit) was supplied by Wolfcraft España S.L, Madrid, Spain. All aqueous solutions were prepared with MilliQ-grade water using a Direct-Q8UV system from Millipore (Millipore Ibèrica S.A., Madrid, Spain). Thiol-functionalized silica particles (SiliaMetS® Thiol, 40-63 μm, 60 Å) were purchased from Teknokroma Analitica S.A., Barcelona, Spain. Mica sheets (Grade V-1 Muscovite) were purchased from SPI Supplies, West Chester, PA, USA. Core histones were obtained from Sigma-Aldrich Co., Spain, and the stock solution was prepared by dilution in phosphate buffer at pH=7 containing 150 mM sodium chloride. Buffer solutions were prepared with doubly deionized water from a Puranity TU System (VWR International Eurolab S.L., Barcelona, Spain) with UV lamp and ultrafilter (VWR), and the pH was adjusted in a Metrohm (Metrohm AG, Herisau, Switzerland) 16 DMS Titrino pH meter fitted with a combined glass electrode and a 3 M KCl solution as a liquid junction.

Characterization

UV-vis and fluorescence spectroscopy. Both UV-vis and fluorescence spectroscopy experiments were performed at room temperature using 1 cm path length Hellma quartz cuvettes (Hellma GmbH & Co. KG., Müllheim, Germany). UV-vis spectra were recorded with an Analytik Jena Specord S600 spectrometer (Analytik Jena AG, Jena, Germany) with a diode array detector, and fluorescence spectra were recorded with a Cary Eclipse Varian fluorimeter (Agilent Technologies Spain, S.L., Madrid, Spain).

Atomic force microscopy (AFM). AFM measurements were conducted under normal ambient conditions using an XE-100 instrument (Park Systems, Suwon, South Korea) in non-contact mode. The AFM tips were aluminium-coated silicon ACTA from Park Systems with a resonance frequency of 325 kHz. For AFM imaging, a drop of the Ag3-AQC diluted sample was deposited onto a freshly cleaved mica sheet (Grade V-1 Muscovite) (Park Systems, Suwon, South Korea), which was thoroughly washed with Milli-Q water and dried under nitrogen flow.

Mass spectrometry. ESI mass spectra were acquired using an LTQ Orbitrap Discovery mass spectrometer (Thermo-Fisher Scientific, Waltham, USA) equipped with an ESI source operating in negative ionization mode. The ESI source conditions were as follows: source voltage −4.5 kV, heated capillary temperature 275° C., capillary voltage −35 V and sheath gas and auxiliary gas 5 and 2 ($N_2$, arbitrary units). For full-scan MS analysis, the spectra were recorded in the range of m/z 100 to 2,000 with a scan speed of 1 scan/s. The mass resolution was set at 30,000 FWHM. The Orbitrap instrument was calibrated using a calibration solution according to the manufacturer's instructions. Monitoring experiments were conducted to obtain the maximum sensitivity for the detection of clusters. Solutions were directly injected into the cell after mixing 1 to 1 with an acetonitrile solution with 1 mM $NH_4Cl$ and 0.1% formic acid.

Ion meter. Ion concentration was measured using a previously calibrated pH & Ion-Meter GLP 22 (Crison Instruments S.A., Barcelona, Spain) by adding a stabilizing solution (sodium nitrate 5 M) at a ratio of 2:100 to the sample at a constant temperature of 25° C.

Flame atomic absorption spectroscopy. The total Ag content in the cluster samples was analysed by flame atomic absorption spectroscopy, performed with a Perkin-Elmer 3110 with a Ag hollow cathode lamp Lumia from Perkin-Elmer (Madrid, Spain) (current 10 mA).

Cell Lines

Human lung adenocarcinoma cell line (A549) and human breast adenocarcinoma cell line (MCF7) were obtained from DMSZ (Leibniz Institute DSMZ—German Collection of Microorganisms and Cell Cultures, Braunschweig, Germany). A luciferase-expressing cell line derived from A549 cells by stable transfection of the North American Firefly Luciferase gene expressed from the CMV promoter (A549 Luc-C8 Bioware® cell line) obtained from Caliper Life-Sciences (Caliper Life Sciences, Hopkinton, MA, USA). A human glioblastoma multiform cell line (U87-Luc) was kindly provided by Joan Seoane, Vall d'Hebron Institut d'Oncologia (VHIO), Barcelona, Spain. All cell lines grow adherently as monolayers. The A549 and A549-Luc cell lines were maintained in Dulbecco's Modified Eagle Medium (low-glucose, D6046, Sigma), and the MCF7 and U87-Luc cell lines were maintained in Dulbecco's Modified Eagle Medium (high-glucose) (D5671, Sigma). The medium was supplemented with 10% foetal calf serum and 1% (v/v) L-glutamine, penicillin and streptomycin (Gibco, Thermofisher). In the case of modified cell lines, puromycin (1.3 μg/mL for A549-Luc and 5 μg/mL for U87-Luc) was added to the medium to select stably transfected cells. Cells were incubated in a humidified incubator at 37° C. with 5% $CO_2$ and grown in 100 mm culture dishes to approximately 70-80% confluence. For sub-culturing, the medium was removed, and the cells were washed with phosphate buffered saline (PBS); trypsin/EDTA (Gibco) was used to induce cell detachment. Finally, the cells were suspended in culture medium and passage into fresh dishes at a ratio of 1:5 or 1:10. When necessary, cells were counted using a Neubauer haemocytometer. All procedures were performed under sterile conditions in a laminar air flow hood. All cell lines were stored frozen with complete growth medium supplemented with 10% DMSO (Sigma, D2650) at liquid nitrogen vapor temperature.

Animals

Female athymic nude mice weighing approximately 20-25 grams at the age of 8-12 weeks (Janvier Laboratories, Le Genest-Saint-Isle, France) were used in the in vivo studies. The animals were acclimatized for at least 1 week before experimentation and were housed in ventilated polypropylene cages at an average temperature of 22° C., with 12 hours of daily exposure to light and 12 hours to darkness. All mice received a standard laboratory diet of food and water ad libitum. The experiments were performed according to the Rules of the Santiago de Compostela University Bioethics Committee and in compliance with the Principles of Laboratory Animal Care according to Spanish national law (RD 53/2013).

Orthotopic Lung Cancer Model

The anti-tumour efficacy of $Ag_3$-AQCs was assessed in an orthotopic lung cancer model that metastasizes to the mediastinal lymph nodes. The model was developed following the protocol described by Borrajo et al. *J. Control. Release* 2016, 238: 263, adapted from Cui et al. Cancer Res. Treat. 2006, 38: 234. A suspension of $1\times10^6$ non-small cell lung carcinoma luciferase expressing cells (A549 Luc-C8 Bioware® cell line) in PBS (50 μL) was injected through the intercostal space into the left lung of athymic nude mice. During this procedure, mice were anaesthetized using 4% isoflurane inhalation. To follow tumour growth, luciferin was injected into the intraperitoneal cavity at a dose of 150 mg/kg body weight approximately 5 minutes before imaging. Luciferase bioluminescence was imaged under vaporized isofluran anaesthesia using an IVIS® Living Image® System (Caliper Life Sciences, Hopkinton, MA, USA) that allowed monitoring of both the primary tumour growth and cancer cell dissemination in a semi quantitative fashion. After in vivo imaging for several days (up to 37 days), the mice were sacrificed, and protein extracts were obtained from different organs to quantify luciferase activity. Briefly, organs were homogenized in DIP buffer (50 mM pH 7.5, 150 mM NaCl, 1 mM EDTA, 2.5 mM EGTA, 0.1% Tween-20, 10 mM β-glycerophosphate, 1 mM sodium orthovanadate, 0.1 M PMSF, 0.1 M NaF and protease bitor cocktail (Sigma)) using a tissue homogenizer. After 15 minutes of high-speed centrifugation, the supernatants were quantified using a Bradford colorimetric method, and the luminescence was measured using a Lumat BL 9507 luminometer (Berthold Technologies GmbH & Co., Bad Wildbad Germany). The results were expressed as relative luminescence units (RLU) per μg of extracted protein.

Quiescence Induction and Flow Cytometry Verification

To arrest cells in G0/G1 phase of the cell cycle, A549 cells were plated at 20,000 cells/dish in medium containing 10% FBS. After 24 hours, the medium was replaced with medium supplemented with 0.05% FBS for 72 hours. Cells were collected, and the cell cycle profile was analysed by flow cytometry to assess the percentage of cells in G0/G1 phase (quiescent state). Cells were fixed in 70% ethanol overnight, washed twice with PBS, and incubated for 30 minutes in the dark in 0.5 mL propidium iodide (0.1 mg/mL). The stained cells were analysed using a Guava EasyCyte flow cytometer using the InCyte program (Millipore, Merck Chemicals & Life Science S.A, Madrid, Spain). Once verified, this protocol was used in all experiments with quiescent cells (serum-starved) in this work.

Chromatin Accessibility Assay

Chromatin accessibility after $Ag_3$-AQC treatment was measured in an A549 cell line and in tissues from mice bearing orthotopic lung tumours derived from A549 cells. First, $5\times10^5$ A549 cells were seeded in 60 mm culture dishes, and 24 (proliferating cells) or 72 (serum-starve cells) hours later were treated with $Ag_3$-AQCs (55.61 ng/mL) for 1 hour in serum-free medium. Next, the medium was replaced with complete medium for 3 hours, and the cells were washed twice with PBS, trypsinised and centrifuged. The supernatants were removed, and the cell pellets were washed with PBS and suspended in lysis buffer. Mice bearing orthotopic lung tumours derived from A549 cells were injected with $Ag_3$-AQCs (0.05 mg/kg). After 24 hours, the animals were sacrificed, and the lungs and kidneys were removed. Small pieces (1-2 $mm^3$) of tumour (lung) and kidney were homogenized using a Dounce homogenizer and suspended in lysis buffer. From this point, the cells and tissues were treated similarly; chromatin was isolated and treated with a nuclease mix following the instructions provided by the manufacturer using an EpiQuick™ Chromatin Accessibility Assay kit (Epigentek, Farmingdale, NY, USA). DNA was then isolated and amplified using real-time PCR system (Applied Biosystems, Thermofisher, Spain) and gene-specific primers for GAPDH (Epigentek).

Quantification of Platinum in DNA of Cell Samples and Mouse Organs

DNA-bound platinum was assessed as previously described in Comenge et al. *PLoS One* 2012, 7: e47562. Briefly, $5\times10^5$ A549, MCF7 or U87-luc cells were seeded in 60 mm diameter plates. After 24 hours (or 72 hours in case of quiescent cells), cells were treated with 1) CDDP 50 μM for 6 hours in complete medium, 2) Ag3-AQCs (55.61 ng/mL) in serum-free medium for 1 hour, or 3 hours) the combination of both treatments: Ag3-AQCs (55.61 ng/mL) in serum-free medium for 1 hour and then 5 hours with CDDP 50 μM in complete medium. After the treatment, the cells were washed twice with PBS, trypsinised and centrifuged. The supernatants were removed, and the cell pellets were stored at −20° C. overnight. The procedure to quantify platinum in mouse organs was as follows: tumour-bearing nude mice were injected with 1) 100 μL CDDP (4 mg/kg) or 2) 50 μL CDDP (4 mg/kg) and 50 μL $Ag_3$-AQCs (0.05 mg/kg). After 24 hours, the animals were sacrificed, and the organs were removed. Small pieces (1-2 $mm^3$) of tumour (lung) and other organs (heart, liver, kidney, spleen, brain and bone marrow) were separated using a scalpel. From this point, the steps for DNA extraction are common to cells and tissue samples. After freezing overnight, cell or tissue pellets were suspended in 300 μL of lysis buffer (150 mM Tris pH 8; 100 mM EDTA pH 8; 100 mM NaCl; 0.5% SDS) and 10 μL of Proteinase K (20 μg/μL). The cell pellets/tissues were pierced with a needle five times and incubated in a water bath at 56° C. for 2 hours for cells and overnight for tissues After incubation, 3 M sodium acetate and phenol/chloroform/isoamyl alcohol were added (0.1 and 1.0 volume equivalents) and vortexed gently for 1 minute. The samples were centrifuged at 16,000×g for 10 minutes, and the supernatants were recovered. For DNA precipitation, two volumes of cold ethanol 10-10% were added, and the suspension was centrifuged at 16,000×g for 10 minutes at 4° C. After centrifugation, the supernatants were discarded, and 1 mL of cold 70% ethanol was added to pellets, vortexed gently for 5 seconds and centrifuged at 16,000×g for 10 minutes at 4° C. The pellets were dried at room temperature and resuspended in 0.1 mL TE buffer. The DNA concentration was determined using a NanoDrop 2000 spectrophotometer (Thermofisher, Spain). Next, 0.1 mL of TE buffer was removed using the speed-vac, and the DNA was resuspended in 0.2 mL 65% $HNO_3$. Finally, the amount of platinum was determined by mass spectrometry using an ICP-MS BRUCKER 820-MS with a low-flow glass Micromist nebulizer and a double-pass spray chamber with a Peltier cooling (3° C.) and quartz torch (Bruker Corp., Billerica, MA, USA).

Cell Viability

Flow Cytometry Measurement

Cell viability was quantitated by flow cytometry using the Guava ViaCount Reagent (Millipore). A549 cells ($6\times10^4$) were seeded in 12-well dishes and 24 hours (proliferating cells) or 72 hours (quiescent cells) later were treated with 1) $Ag_3$-AQCs (55.61 ng/mL) in serum-free medium for 1 hour and then 24 hours in complete medium; 2) $Ag_3$-AQCs (55.61 ng/mL) in serum-free medium for 1 hour and then 24 hours with various drugs (CDDP 50 μM, OXA 50 μM, CBDCA 100 mM, GEM 100 μM, BCNU 400 μM or DOX 7.5 μM); 3) 24 hours with various drugs (CDDP 50 μM, OXA 50 μM, CBDCA 100 mM, GEM 100 μM, BCNU 400 μM or DOX 7.5 μM); or 4) $Ag_3$-AQCs (55.61 ng/mL) in serum-free medium for 1 hour, 24 hours in complete medium without treatment and then 24 hours with CCDP 50 μM. After treatment, the cells were collected, washed with PBS and suspended in 500 μL of PBS. To prepare stained samples, the cell suspension was mixed with the Guava ViaCount Reagent (Millipore) following the manufacturer's instructions. The stained cells were analysed on the Guava EasyCyte flow cytometer (Millipore) using the Guava ViaCount software.

Luminescent Assay $5\times10^3$ A549 Luc-C8 cells were seeded in 96 well plates and 24 hours (proliferating cells) or 72 hours (serum-starved cells) later were treated with 1) $Ag_3$-AQCs (55.61 ng/mL) in serum free medium for 1 hour and 24 hours more in complete medium, 2) $Ag_3$-AQCs (55.61 ng/mL) in serum free medium for 1 hour and 24 hours more with different doses of CDDP (IC5: 5 μM, IC25: 10 μM, IC50: 50 μM and IC75: 100 μM), OXA (IC5: 2.5 μM, IC25: 12.5 μM, IC50: 50 μM and IC75: 200 μM) or CBDA (IC5: 0.25 μM, IC25: 0.5 μM, IC50: 1 mM and IC75: 2 mM) and 3) 24 hours with different doses of CDDP (IC5: 5 μM, IC25: 10 μM, IC50: 50 μM and IC75: 100 μM), OXA (IC5: 2.5 μM, IC25: 12.5 μM, IC50: 50 μM and IC75: 200 μM) or CBDCA (IC5: 0.25 μM, IC25: 0.5 μM, IC50: 1 mM and IC75: 2 mM). After that, treatments were removed and 20 μL of lysis buffer (Promega) added to wells and incubated for 30 minutes, shacking. Lysates were then transferred to 1.5 mL tubes and centrifuged for 15 minutes at high speed. Supernatants were collected and the amount of protein was quantified using a Bradford colorimetric method and luminescence was measured using a Lumat BL 9507 luminometer (Berthold Technologies). Results were expressed as relative luminescence units (RLU) per μg of extracted protein.

Microarrays

A549 ($5\times10^5$) cells were seeded in 60 mm culture dishes. After 24 hours, the cells were treated with $Ag_3$-AQCs (41.5 ng/mL) for 1 hour in serum-free medium. The medium was then removed and replaced with complete medium for 0, 4 or 24 hours. At these time points, the cells were collected, and their RNA was isolated using the kit NucleoSpin ARN (Macherey-Nagel, Düren, Germany) following the manufacturer instructions. The RNA concentration was quantified using a spectrophotometer (Nanodrop 2000), and the quality was assessed measuring the RNA Integrity Number (RIN) using the Agilent RNA 6000 Nano kit and the Agilent 2100 Bioanalyzer (Agilent Technologies, Santa Clara, USA). Only the samples with RIN>7 were considered acceptable. The samples were stored at −80° C. until use. The Human Gene 2.1 ST Array (Affymetrix, Santa Clara, USA) was used to hybridize the human samples following the manufacturer's instructions. Background correction, normalization, probe summarization and data analysis were performed using the Expression Console and the Transcriptome Analysis Console (Affymetrix).

DNA Damage Assays

Phosphorylated H2AX Assessment

Phosphorylated H2AX (pH2AX) assessment was done as described in Muslimovic, et al. *Nat. Protoc.* 2008, 3: 1187. Briefly, A549 cells ($4.5\times10^4$) were seeded in a 6-well dish. After 24 hours, cells were treated with Ag3-AQCs and etoposide in serum-free medium for 1 hour. Cells were collected and washed twice with cold PBS. The supernatant was discarded, and the pellet was fixed in 50 μL of fixation buffer for 5 minutes while protected from light. Then, 150 μL of Block-9 buffer with 0.6 μg/mL of anti-pH2AX (ser139) FITC conjugate (16-202A, Millipore) were added, and the cells were incubated at 4° C. for 3 hours while protected from light. The cells were washed twice with PBS and incubated overnight in the dark with 0.1 mL of propidium iodide (0.01 mg/mL). The stained cells were analysed on the Guava EasyCyte flow cytometer using the InCyte program (Millipore).

Comet Assay

A549 cells ($5\times10^5$) were seeded in 60-mm plate dishes and 24 hours later treated with Ag3-AQCs (55.61 ng/mL) or $H_2O_2$ (100 M) positive control for 1 hour in serum-free medium. The cells were subsequently collected by trypsinisation and washed once in ice-cold PBS ($Ca^{2+}$ and $Mg^{2+}$ free). The cells were then suspended in ice-cold PBS ($1\times10^5$ cells/mL), and an alkali comet assay was performed according to instructions provided by the manufacturer (Trevigen, Gaithersburg, USA). Images were obtained using an Olympus IX51 microscope equipped with an Olympus DP72 camera and CellSens Imaging Software (Olympus, Tokyo, Japan).

DOX Analysis

Nuclear DOX Content

The nuclear uptake of DOX was determined using fluorescence microscopy. A549 cells ($5\times10^5$) were seeded in 12-well plates. After 24 hours, cells were treated with 1) DOX (7.5 μM) for 30 minutes or 2) $Ag_3$-AQCs (55.61 ng/mL) for 30 minutes and DOX (7.5 μM) for another 30 minutes. Images were obtained using an Olympus IX51 microscope equipped with an Olympus DP72 camera and CellSens Imaging Software.

Flow Cytometry Measurement of DOX Accumulation

To quantify the cellular uptake of DOX in the presence of $Ag_3$-AQCs, A549 cells ($5\times10^5$) were seeded in 12-well plates. Twenty-four hours later, the cells were treated with 1) DOX (7.5 μM) for 4 hours or 2) $Ag_3$-AQCs (55.61 ng/mL) for 30 minutes and DOX (7.5 μM) for 4 hours. After that, the cells were collected, washed with cold PBS and fixed with 0.2% paraformaldehyde (PFA) for 5 minutes. The samples were then suspended in 200 μL of PBS and analysed on the Guava EasyCyte flow cytometer using the InCyte program.

Histological Analysis

Mouse lungs were fixed in 10% neutral buffered formalin for 24 hours and embedded in paraffin. Sections 4 mm thick were mounted on FLEX IHC microscope slides (Dako-Agilent, Glostrup, Denmark) and heated in an oven at 60° C. for 1 hour. The immune-histochemical technique was automatically performed using an AutostainerLink 48 (Dako-Agilent). After deparaffination and epitope retrieval in EnVision FLEX target retrieval solution (high pH) for 20 minutes at 97° C., the slides were allowed to cool in PT Link to 65° C. and then in Dako wash buffer for 5 minutes at room temperature (RT). The immunostaining protocol included incubation at RT in: (1) EnVision FLEX peroxidase-blocking reagent (Dako-Agilent) for 5 minutes; (2) ready-to-use FLEX primary antibody (Dako-Agilent) anti-CK7 (clone OV-TL 12/30), for 20 minutes; (3) EnVision FLEX/HRP (dextran polymer conjugated with horseradish peroxidase and affinity-isolated goat anti-mouse and anti-rabbit immunoglobulins) for 20 minutes; (4) substrate working solution (mix) (3,3'-diaminobenzidine tetrahydrochloride chromogen solution) (Dako-Agilent) for 10 minutes; and (5) EnVision FLEX haematoxylin (Dako-Agilent) for 9 minutes. Sections were examined and photographed using an Olympus PROVIS AX70 microscope equipped with an Olympus DP70 camera.

Statistical Analysis

A Mann-Whitney Test was applied to examine differences in biodistribution and efficacy studies associated with CDDP treatments versus CDDP+ Ag3-AQCs. The mean±standard deviation (SD) was determined for each treatment group. The differences were considered significant for *p<0.05, and very significant for *p<0.01. For STORM analysis, significance was calculated using one-way ANOVA. All statistical analyses were performed with GraphPad Prism Version 5.0 software (GraphPad Software, Inc., La Jolla, USA).

Human Topoisomerase I (Topo I) Relaxation Assay

The activity was assessed using the Human Topoisomerase I Relaxation Kit according to the manufacturer (Inspiralis, Norwich, UK). Briefly, 0.5 mg of relaxed pBR322 DNA were preincubated for 30 minutes at room temperature with Ag3-AQCs in 30 mL reaction under the following conditions: 35 mM Tris-HCl (pH 7.5), 24 mM KCl, 4 mM MgCl2, 2 mM DTT, 1.8 mM spermidine, 1 mM ATP, 6.5% (w/v) glycerol and 0.1 mg $mL^{-1}$ BSA. After that, 1 U of human Topo I was added and incubation was continued for 30 minutes at 37° C. The reaction was stopped by addition of 30 mL chloroform/iso-amyl alcohol and 6 mL of loading buffer before being loaded on an agarose gel (1%: w/v) in TAE (40 mM Tris-acetate, 2 mM EDTA) buffer without ethidium bromide.

Human Topoisomerase II (Topo II) Decatenation Assay

Human Topo II activity was assessed using a commercial kit (Inspiralis, Norwich, UK). Briefly, 200 ng of kDNA were preincubated for 5 minutes at room temperature with Ag3-AQCs at various concentrations in 40 mM HEPES-KOH (pH 7.6), 100 mM potassium glutamate, 10 mM magnesium acetate, 10 mM DTT, 1 mM ATP and 50 mg $mL^{-1}$ albumin, in 30 mL total reaction volume. After that, 1U of Topo II was added and incubation was continued for 30 minutes at 37° C. The reaction was stopped by addition of 30 mL chloroform/iso-amyl alcohol and 6 mL of loading buffer, vortexed and centrifuged briefly (5-10 seconds each) before being loaded on an agarose gel (1%: w/v) in TAE (40 mM Tris-acetate, 2 mM EDTA).

Example 1: Ag3-AQC Synthesis Method

Ag3-AQCs were synthesized by a new development of an electrochemical method previously reported in Buceta et al., *Angew. Chemie Int. Ed.* 2015, 54: 7612, so that high amounts of Ag3-AQCs required in this work could be obtained for animal tests. Substantial modifications consisted of increasing the electrode area sevenfold and the voltage and time of the reaction threefold. To carry out these modifications, the previously used Pt counter electrode was replaced with a Ag electrode, since $H_2$ evolution over the Pt electrode precludes the use of high voltages, and thereby reduces the yield of the synthesis. Moreover, the use of Pt as a counter electrode requires a more complex cleaning process and is more expensive. The synthesis was carried out with a Biologic VMP300 potentiostat (Seyssinet-Pariset, France). A Methrom thermally insulated three-electrode electrochemical cell was used with a hydrogen electrode as a reference and two Ag foils (17.5 $cm^2$ surface area) as counter and working electrodes. These electrodes faced each other and were separated at a distance of 3 cm. A 6 V constant voltage was applied at 25° C. for 3,600 seconds. Prior to the synthesis, both silver electrodes were polished with sandpaper followed by alumina (~50 nm), washed thoroughly with MilliQ water and sonicated.

Example 2: Ag3-AQC Purification Using DNA

An aqueous dispersion of low size silver clusters was synthesized as described in Example 1. A sample containing Ag cations and clusters of small size (less than 10 atoms) was used for preparation of DNA adducts and dialysis procedures. AFM and UV-Vis characterization indicated that the sample contained mainly Ag2 and Ag3 clusters.

The incubation mixture, DNA+Ag-AQCs (1:1 in mass), was prepared by mixing calculated volumes of aqueous solutions of DNA and Ag-AQCs samples followed by gently stirring during 12 hours at room temperature. After this step, the mixture was transferred to a dialysis cassette with a 3.5 KDa membrane.

Three different dialysis procedures were done along the separation process. In the first step the cassette was immersed in MilliQ water for 24 hours. In the second dialysis, a solution of higher ionic strength was used (NaCl 1M) with the objective of removing any trace of silver cation present as a minor impurity after the first dialysis step.

Before the third dialysis, the mixture DNA/Ag-AQCs was heated at 96° C. for 8 hours, to denature the DNA allowing separation of intercalated clusters, and immediately cooled to 0° C. to prevent renaturalisation. The last dialysis was performed in MilliQ water for 24 hours at 0° C.

The efficiency of the separation was followed by fluorescence spectroscopy, which was chosen as characterization tool of the dialysis extraction products, due to its high sensibility and simplicity. The result obtained after the first dialysis is shown in FIG. 22. It can be seen the presence of only the band at 300 nm associated with the presence of Ag2. This indicates the effective separation of Ag2 from the initial cluster sample, as it is represented in the scheme of the same Figure. Subsequent dialysis shows no evidence of any species, indicating the total separation of Ag2 (first dialysis step) from the original sample. The last dialysis extraction, after denaturalization of DNA (96° C. for 8 hours), is shown in FIG. 23. It can be seen the presence of a main band at 350 nm, attributed to Ag3, confirms the isolation of Ag3 clusters after the previous dialysis steps.

The obtained results confirm the previous reports (Buceta et al. 2015) showing that Ag3 clusters tend to intercalate between the DNA strands, whereas Ag2 clusters are more probably loosely bound to the exterior of the helix. This explains the reason why Ag2, not bounded to DNA, elutes very easily in the initial dialysis steps.

This work demonstrates the possibility of using the different binding properties to DNA to separate preformed small naked clusters differing by only one atom. Due to the high specificity of the interaction, one can efficiently use it for the selective separation of Ag2 and Ag3 in cluster samples containing both species. Moreover, the developed procedure allows also the purification of Ag3-AQCs (mainly from Ag ions as by-product of the synthesis).

Example 3: Ag3-AQC Purification Using Thiolated Resin

The elimination of Ag ions (which are always present after the cluster synthesis) from the as-synthesized samples was previously performed by adding NaCl. However, this process is inefficient because a significant number of clusters are removed along with the silver precipitate. Thiolated resin was used to selectively separate Ag ions, which greatly improved the results of the purification step (see FIG. 1). The new procedure is based on the observation that Ag3-AQCs unexpectedly do not bind to thiols opposite the Ag ions. Therefore, commercial silica particles functionalized with thiols were used to eliminate silver ions due to the observed large difference in affinity between clusters and ions with thiols. This method was also, unexpectedly, found to remove AQCs larger than 3 atoms, therefore this method was also used to selectively purify AQCs consisting of 3 or fewer zero-valent transition metal atoms.

The procedure consisted of adding 400 mg thiolated-silica particles to about 1 L of synthesis reaction. The mixture was stirred overnight, with subsequent separation of silica particles. An ion-selective electrode was used to verify the elimination of Ag+ ions, and various techniques were used to characterize the Ag clusters in the final samples (as reported previously in Huseyinova et al., *J. Phys. Chem.* 2000, 104: 2630, and Buceta et al., 2015, and as described herein). The purified samples were finally concentrated at 35° C. using a rotary evaporator (Buchi Rotavapor R-210 at a pressure of 2 mbar) (Massó Analitica S.A., Barcelona, Spain) to a final concentration of about 30 mg/L as determined by flame atomic absorption spectroscopy.

Example 4: Ag3-AQC Characterization

Figure 2:
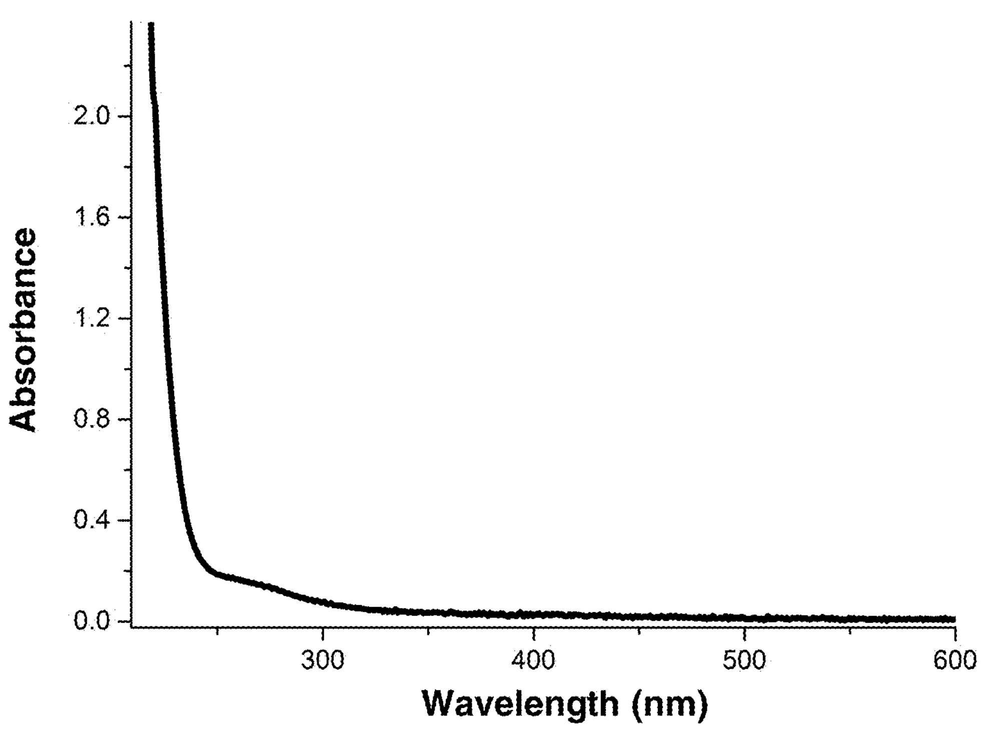
FIG. 2: UV-Vis absorption spectrum of Ag3-AQCs in water.
Figure 3:
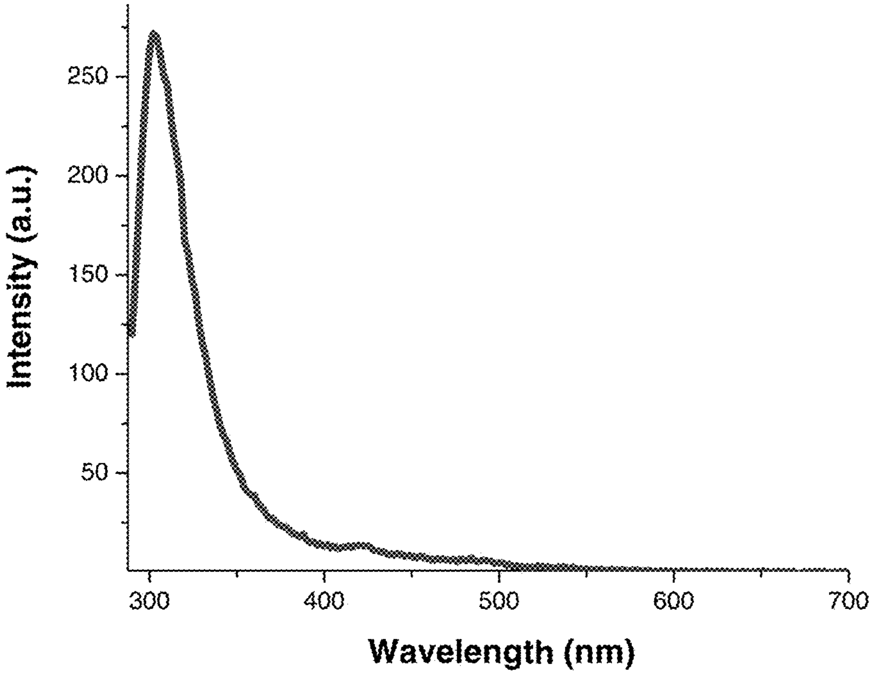
FIG. 3: Fluorescence emission spectrum (λexc=230 nm) of Ag3-AQCs in water.

Cluster samples were characterized by UV-Vis and fluorescence spectroscopy, AFM and ESI− TOF mass spectrometry. Spectroscopic characterization of the samples is in very good agreement with the previously reported for Ag3-AQCs in Lin et al. *ACS Nano* 2009, 3: 395. FIG. 2 shows the UV-Vis spectrum of a water dispersion of Ag3-AQCs. The absence of the Ag plasmon band (around 400 nm) indicates absence of free electrons due to the quantum size confinement, which is observed with clusters (see Philip et al. *Nano Lett.* 2012, 12: 4661. In comparison with the previously reported UV-Vis of naked Ag3-AQCs samples in Buceta et al. 2015, an increase in the absorption intensity between 250 nm and 300 nm can be clearly seen, due to the increase of the Ag3− AQCs concentration obtained with this novel synthesis method. The quantum size confinement causes a splitting of the energy levels at the Fermi level and the appearance of a band gap, being higher as the cluster size becomes smaller. This band gap can be determined, as previously done for other clusters (see Huseyinova et al., *J. Phys. Chem.* 2016, 120: 15902; Attia et al., *J. Am. Chem. Soc.* 2014, 136: 1182, and Buceta et al., 2015) by measuring the fluorescence emission. FIG. 3 shows that Ag3-AQCs present a unique emission peak at ≈305 nm, which is very consistent with previously obtained results in Huseyinova et al., 2000. This band can be associated, using the approximation of the Jellium model, to clusters containing only 2 or 3 atoms. The presence of only a single peak for any excitation wavelength shows the high monodispersity of the sample (even at such high concentration of clusters), and confirms the high efficiency of the synthesis and purification methods developed in this work.

Figure 4:
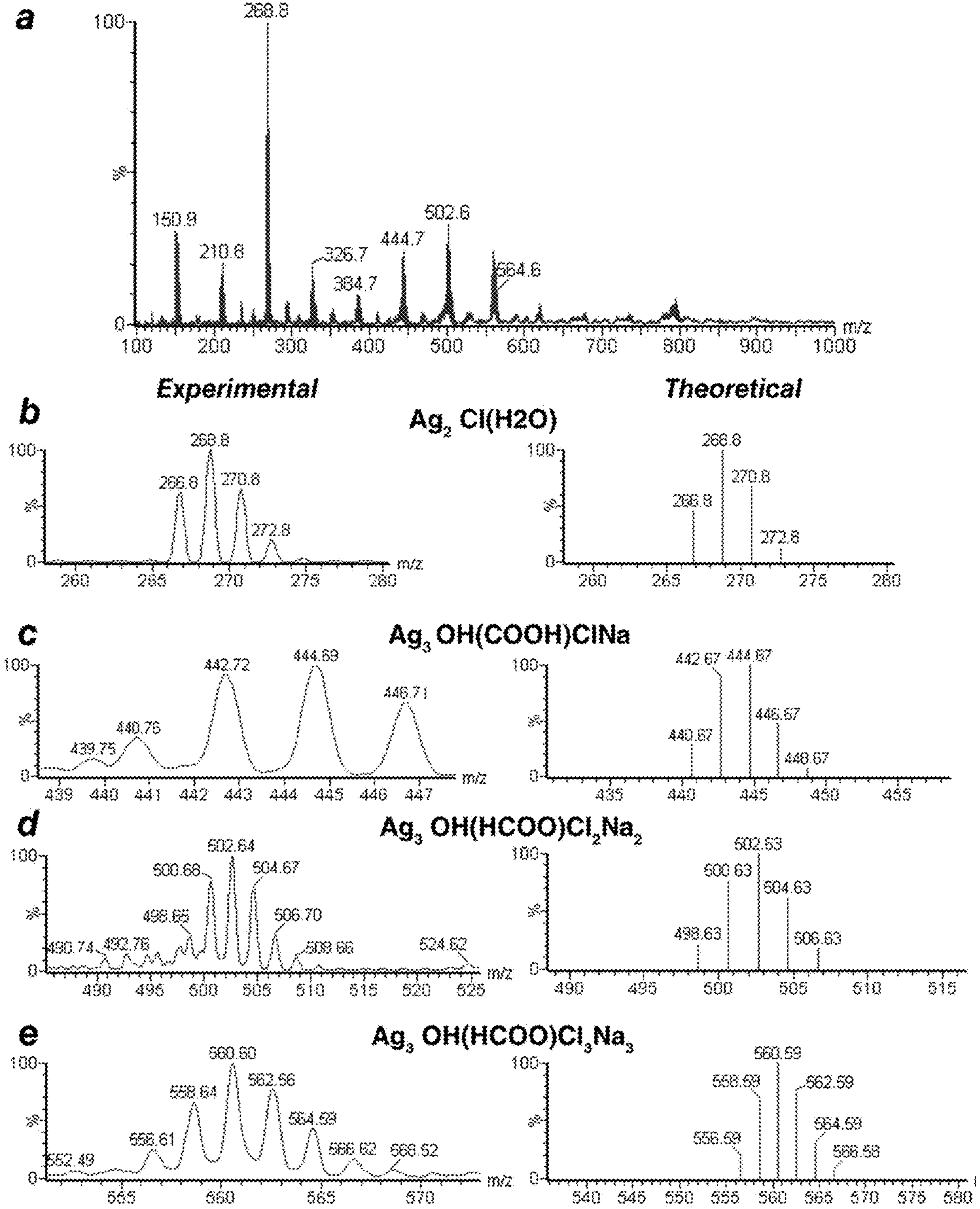
FIG. 4: ESI mass spectrometry. (a) ESI mass spectra of Ag3-AQCs detected in negative mode. (b-e) Experimental and theoretical peaks of the different Ag-AQCs present in the sample.

ESI mass spectrometry was used since this technique uses very soft ionization and in this way fragmentation can be avoided, being ideal for the characterization of small metal clusters (see Lu & Chen, *Anal. Chem.* 2015, 87: 10659, and Gonzalez et al., *Nanoscale* 2012, 4: 7632). Four peaks were obtained in the negative mode, whose assignments are facilitated by the isotopic distribution of Ag: m/z=266.8 (Ag2-AQCs), m/z=440.76, m/z=498.65 and m/z=556.61 (Ag3-AQCs). In FIG. 4 of the SI one can see the agreement of the isotopic distributions with the theoretical simulations, and also with previous publications (e.g. FIG. 2 of the supporting information of Buceta et al., 2015). Therefore, the results show the presence of only Ag2-AQCs and Ag3-AQCs in very good agreement the previous characterization methods.

Figure 5:
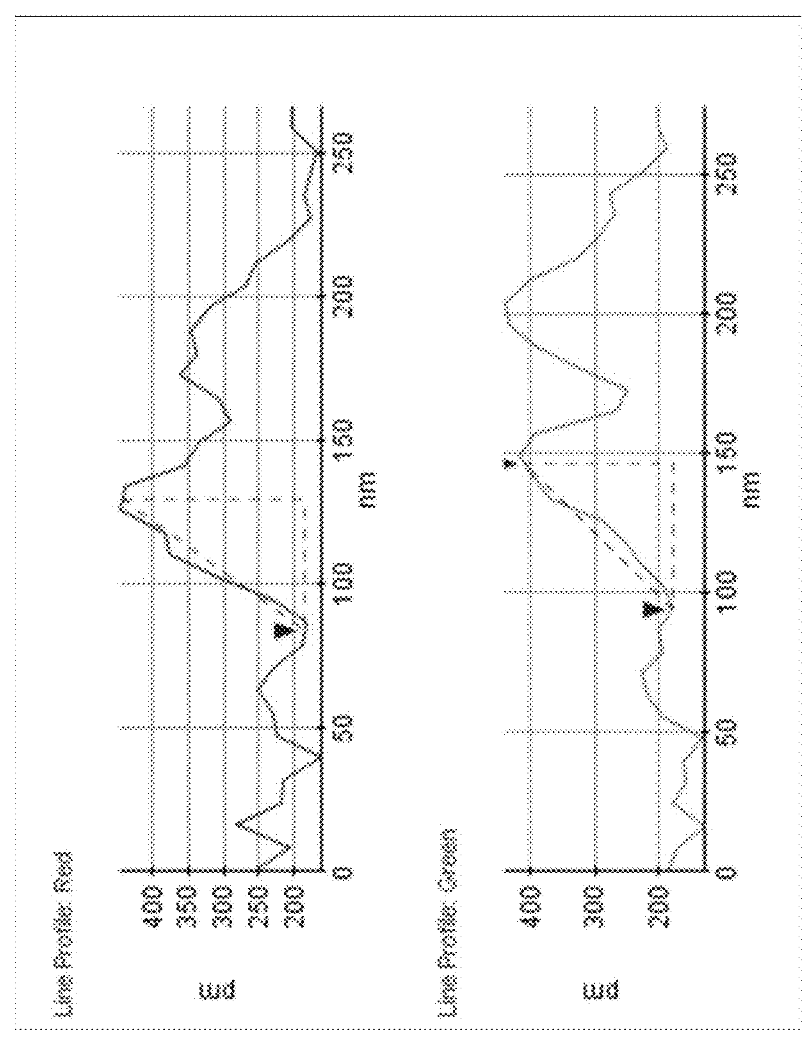
FIG. 5: AFM picture of Ag3-AQCs deposited on mica (mean square roughness ≃150 pm).
Figure 5:
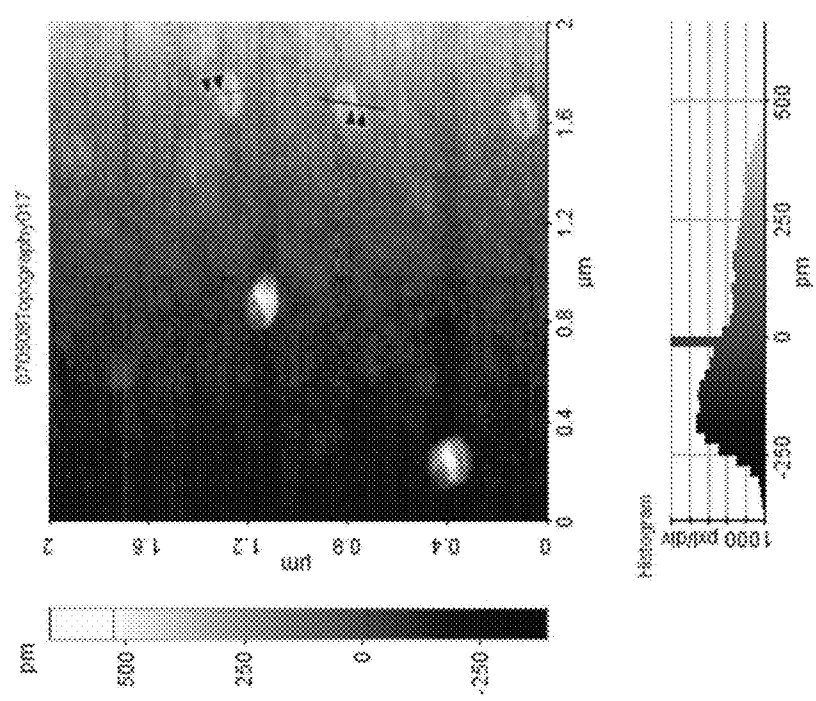

Additional characterization was carried out by non-contact AFM. For this purpose, a dilute sample was deposited over mica (mean square roughness ≃150 pm). FIG. 5 shows about 300 pm high islands, corresponding to 2D size clusters and thus, confirming the presence of clusters with a number of atoms smaller than around 7-10 atoms, as it is predicted from theoretical models (see Lee et al., *J. Phys. Chem.* 2003, 107: 9994). This is also in agreement with the rest of the characterization techniques, and with the previously reported Ag AFM studies in Buceta et al., 2015.

Example 5: Unreactivity of Ag2-AQCs with DNA

Figure 6:
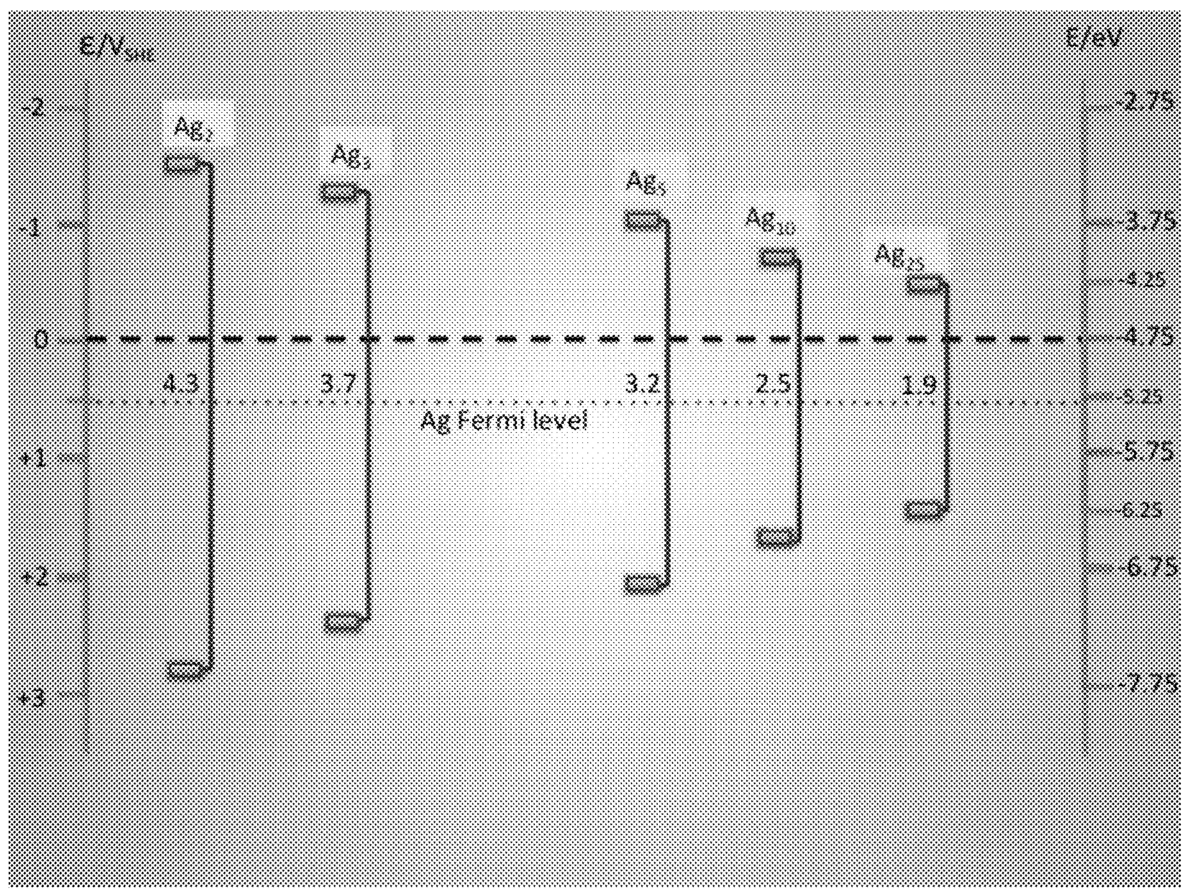
FIG. 6: HOMO-LUMO gaps and position of HOMO/LUMO levels for some Ag clusters of different sizes, according to the Jellium approach.

Although Ag2-AQCs are present in the samples their presence has no influence in the reported results. In a previous publication, neither experimental evidence for the formation of a DNA-Ag2 complex, nor distortion of DNA could be detected with these species (see Buceta et al., 2015, page 7725, right column). Moreover, theoretical calculations clearly demonstrate that Ag2-AQCs do not intercalate in DNA as opposed to Ag3-AQCs which show an intercalating interaction. Furthermore, Ag2-AQCs should have an electronic close shell configuration (1S2), which would indicate a very stable and unreactive behaviour (see Akola et al., *Proc. Natl. Acad. Sci.* 2008, 105: 9157). This fact, together with the large band gap expected for such clusters (about 4.3 eV), and the position of the corresponding HOMO (+2.8V vs RHE) and LUMO (−1.5V vs RHE) levels—see FIG. 6—indicate that Ag2-AQCs should be almost unreactive.

Example 6: Ag3-AQCs Interaction with $O_2$ and MeSH

Density Functional Theory (DFT) Calculations

To understand the unexpected result that Ag3-AQCs do not bind to thiols observed in Example 3, DFT calculations were carried out showing that the presence of adsorbed oxygen onto Ag3-AQCs.

Figure 7:
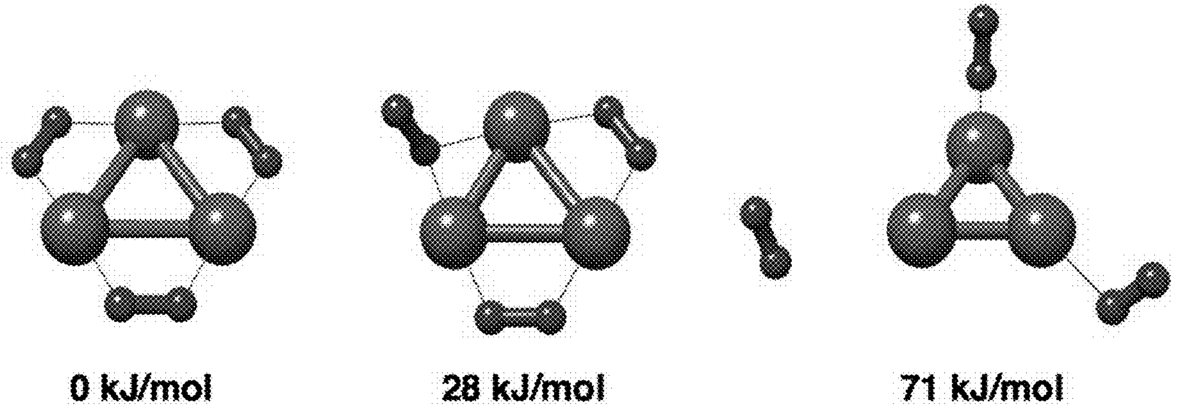
FIG. 7: Optimized geometry and relative energy of three isomeric structures of Ag3-AQCs (larger, three atom structure) in the presence of three $O_2$ molecules (smaller, two atom molecules).
Figure 8:
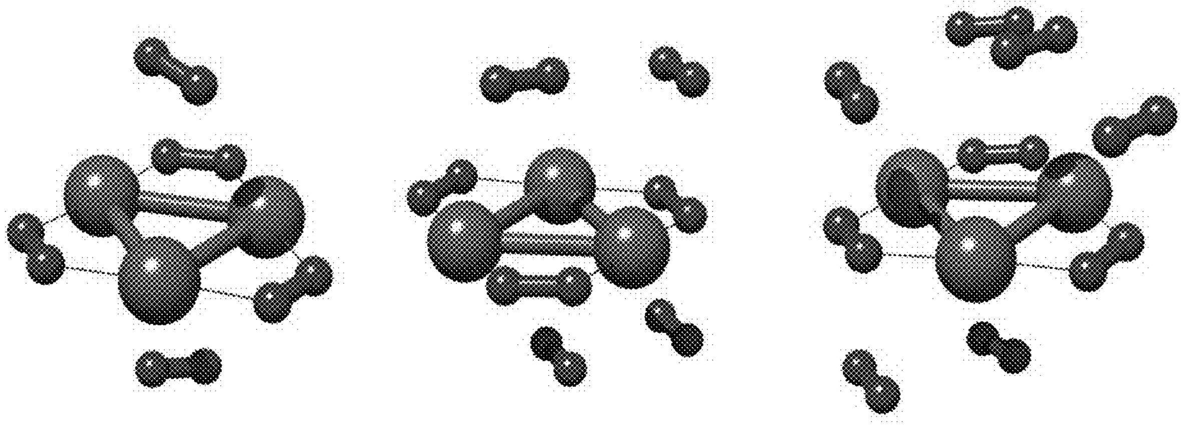
FIG. 8: Optimized geometry of Ag3-AQCs (larger, three atom structure) in presence of five, seven and nine $O_2$ molecules (smaller, two atom molecules).

To calculate the adsorption energy in the presence of adsorbed $O_2$ molecules, a series of DFT calculations have been preliminarily performed to determine the maximum amount of $O_2$ that can be adsorbed on Ag3-AQCs. For example, considering the adsorption of three oxygen molecules on Ag3-AQCs (FIG. 7), the three lowest energy isomers found show that 1,2 bridging produces the most stable structures, compared to other possible Ag—O binding modes. The presence of more than three oxygen molecules around the Ag3-AQCs always produces structures in which the additional oxygen molecules are only loosely adsorbed, for example, above and below the Ag3-AQCs plane. This is shown, for example, by the lowest energy isomers found for the interaction of five, seven and nine oxygen molecules with the Ag3-AQCs (FIG. 8). As a consequence, a suitable model for mimicking the adsorption of methylthiol (MeSH) on Ag3-AQCs, in water solution and in aerobic conditions, was the structure on the left of FIG. 8, in which three $O_2$ molecules are adsorbed in 1,2-bridge position and two 02 molecules are loosely interacting below and above the Ag3-AQCs plane. Starting from this model, MeSH was bound to one of the Ag atoms to mimic the adsorption in the presence of oxygen. In the optimized structures, the adsorption energy (EAd) of MeSH on Ag3-AQCs clusters was determined by the following equation:

$$EAd=E(Ag3/5O_2/MeSH)-E(Ag3/5O_2)-E(MeSH)$$

The energy minimum structure has been found, shown in the inset of FIG. 1, for which indeed the adsorption energy is positive, indicating that is not a stable system. Concerning the structure, three oxygen molecules remain bridged to two Ag atoms, while MeSH and the remaining two oxygen molecules are loosely interacting with the cluster. Such result allows explaining the empirical observation that thiol-derivatives do not bind to Ag3-AQCs. Similar calculations carried out for larger clusters (Ag(n)-AQCs, with n>3 to n=9) show that for such clusters, contrary to Ag3-AQCs, adsorption of thiol-derivatives is favoured.

Computational Details

To mimic the binding between Ag3-AQCs and thiols in aqueous solution and in the presence of molecular oxygen, DFT calculations were performed using the B3LYP functional. The 6-31G(d, p) basis set was used for 0, S, C and H atoms, and the Lanl2dz basis set was used for Ag atoms, as recently reported for systems involving small Au clusters (Corma et al., *Nat. Chem.* 2013, 5: 775). The geometry of the considered systems was fully optimized in the presence of implicit water solvent, using the "conductor-like polarized continuum model" (Barone & Cossi, *J. Phys. Chem.* 1998, 102: 1995). Vibration frequency calculations within the harmonic approximation were performed to confirm that the optimized geometry represented a minimum in the potential energy surface.

Example 7: $Ag_3$-AQCs Inhibition of Recombinant Human Topoisomerases

Figure 9:
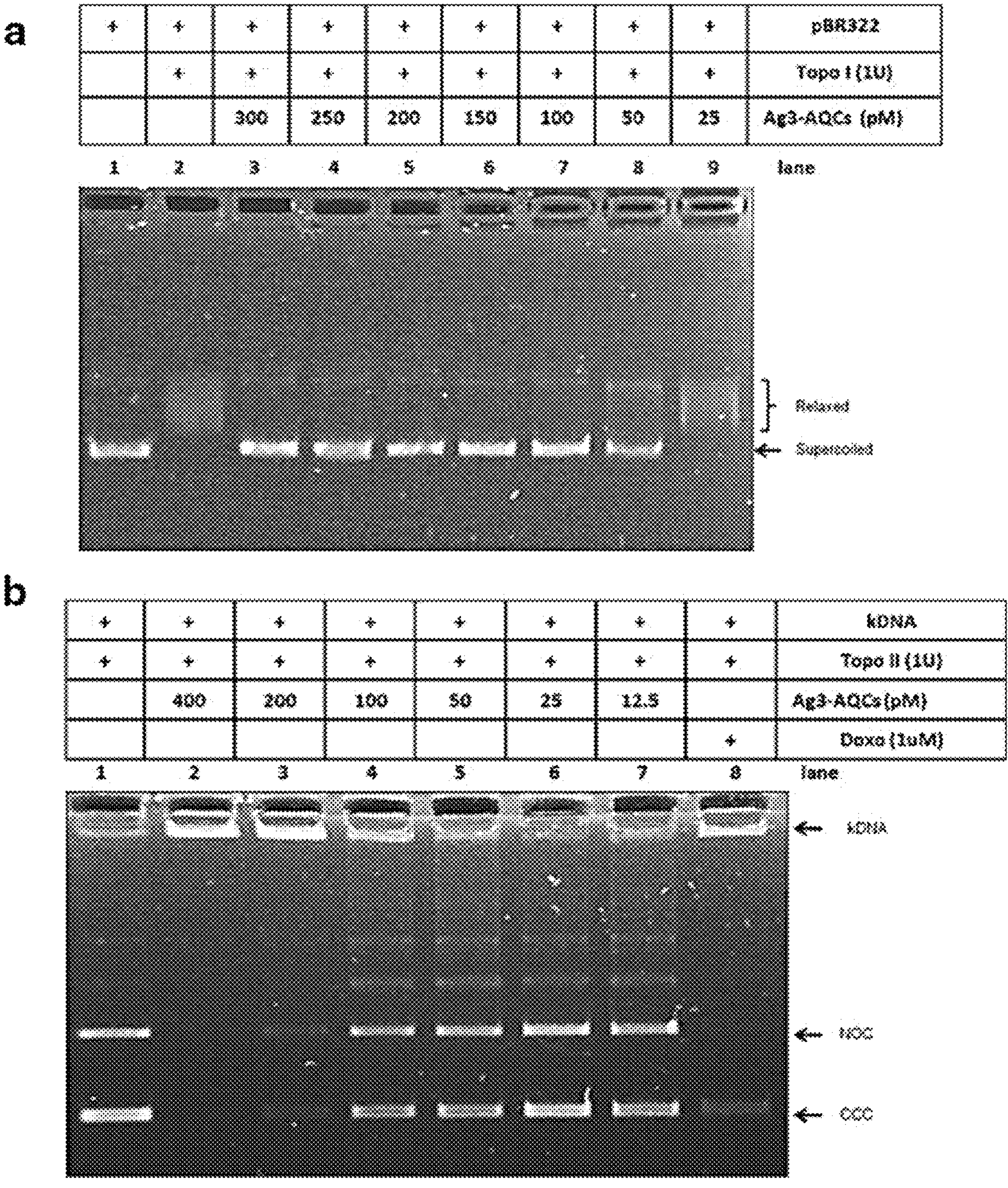
FIG. 9: Ag3-AQCs effect on the activity of human topoisomerases. (a) Human Topoisomerase I activity. Supercoiled DNA pBR322 are resolved (lane 1) and the relaxed DNA species generated by the action of the enzyme are present as a Gaussian distribution of topoisomers (lane 2), pre-treatment of the DNA with Ag3-AQCs inhibited in a dose-dependent manner the action of the enzyme (lanes 3-9). (b) Human Topoisomerase II decatenation activity. Topoisomerase II generated nicked (NOC) and covalently closed circular (CCC) DNA (lane 1). Preincubation of the DNA with Ag3-AQCs inhibits the enzyme in a dose-dependent manner (lane 2-7), doxorubicin (DOXO), was used as an inhibitor positive control (lane 8). The kDNA networks are too large to enter the gel. The images are representative of three independent experiments.

The effect of Ag3-AQCs on DNA unwinding and subsequent lengthening of the double helix is very strong (Buceta et al., 2015). As a result of the topological modification of the DNA, Ag3-AQCs inhibit the binding of DNA sequence-specific binding proteins to DNA and the binding of DNA topology-dependent binding proteins such as bacterial topoisomerase IV and DNA gyrase (Neissa et al. *Chem. Sci.* 2015, 6: 6717). Inhibitors of human topoisomerases are currently used as anticancer agents (Pommier et al. *Chem. Biol.* 2010, 17: 421). Therefore, it was investigated whether Ag3-AQCs also affect human recombinant topoisomerases I and II. Human Topo I relaxation and human Topo II decatenation in vitro assays demonstrated that this was the case, as shown in FIG. 9.

Example 8: Ag3-AQCs Action in Single-Nucleosome Destabilization

Figure 15:
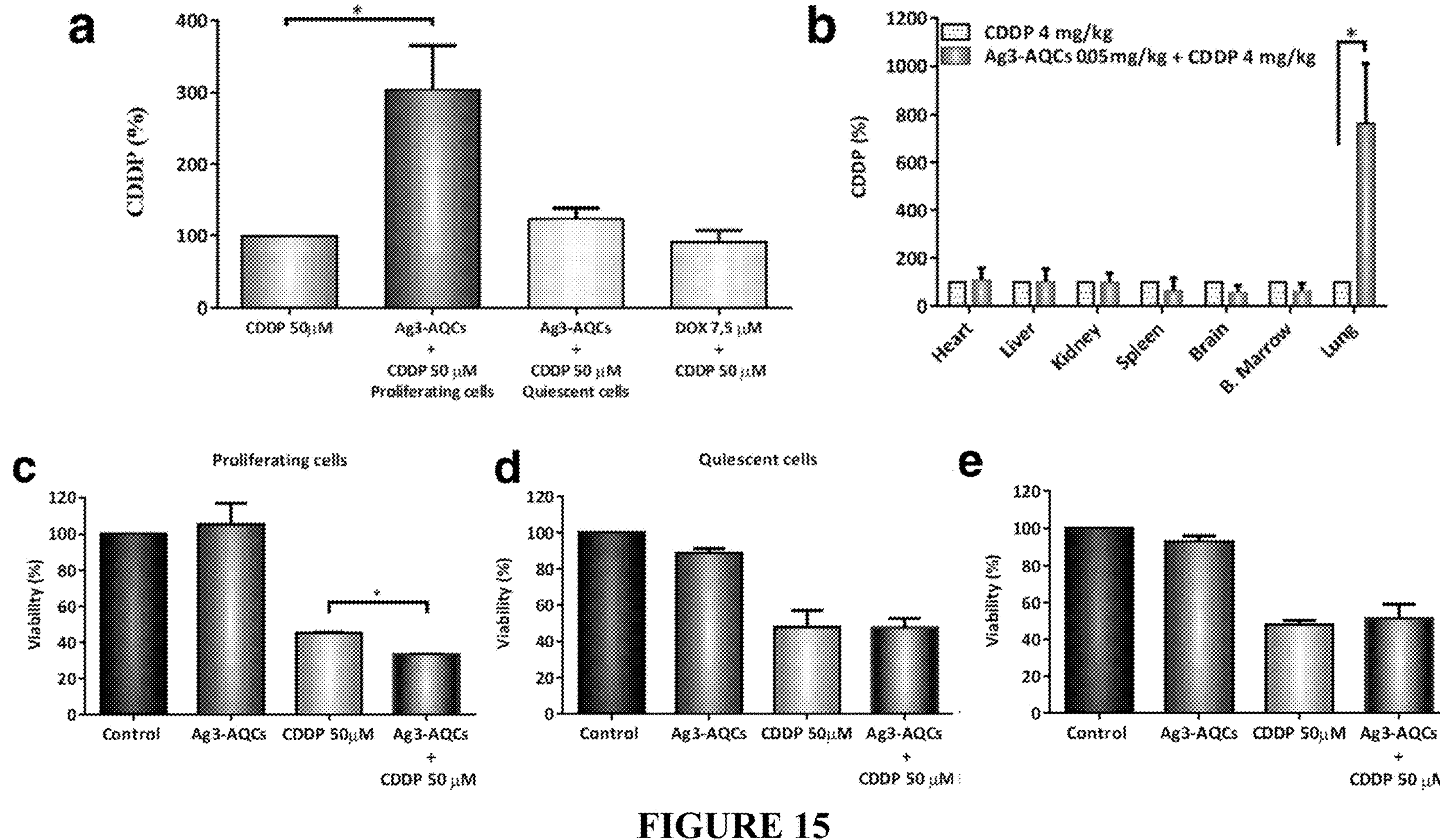
FIG. 15: Co-administration of Ag3-AQCs and cisplatin (CDDP) increase the amount of platinum bound to DNA in A549 proliferating cells and in lung tumours from mice, resulting in a rise in cell mortality. Mass spectrometry quantification of platinum bound to DNA in (a) proliferating or serum-deprived A549 cells treated with CDDP alone or in combination with Ag3-AQCs or DOX and (b) in organs from mice treated with CDDP alone or in combination with Ag3-AQCs. (c-e) Flow cytometry measurement of cell viability in proliferating (c) and serum-deprived (d) A549 cells treated with Ag3-AQCs or CDDP alone or with a combination of both. (e) A549 proliferating cells treated with Ag3-AQCs and 24 hours later with CDDP. Note that in (d) and (e) the Ag3-AQC-potentiating effect on CDDP action is lost.

Unexpectedly, Ag3-AQCs presented no cytotoxicity when administered to A549 human lung adenocarcinoma cells (for example, see FIG. 15*c-e*). Eukaryotic DNA is packed into chromatin that presents a physical barrier that must be overcome by DNA-binding factors (Skene et al. *Elife* 2014, 3: e02042). Thus, it was considered whether chromatin could affect Ag3-AQCs action in eukaryotic cells.

Figure 10:
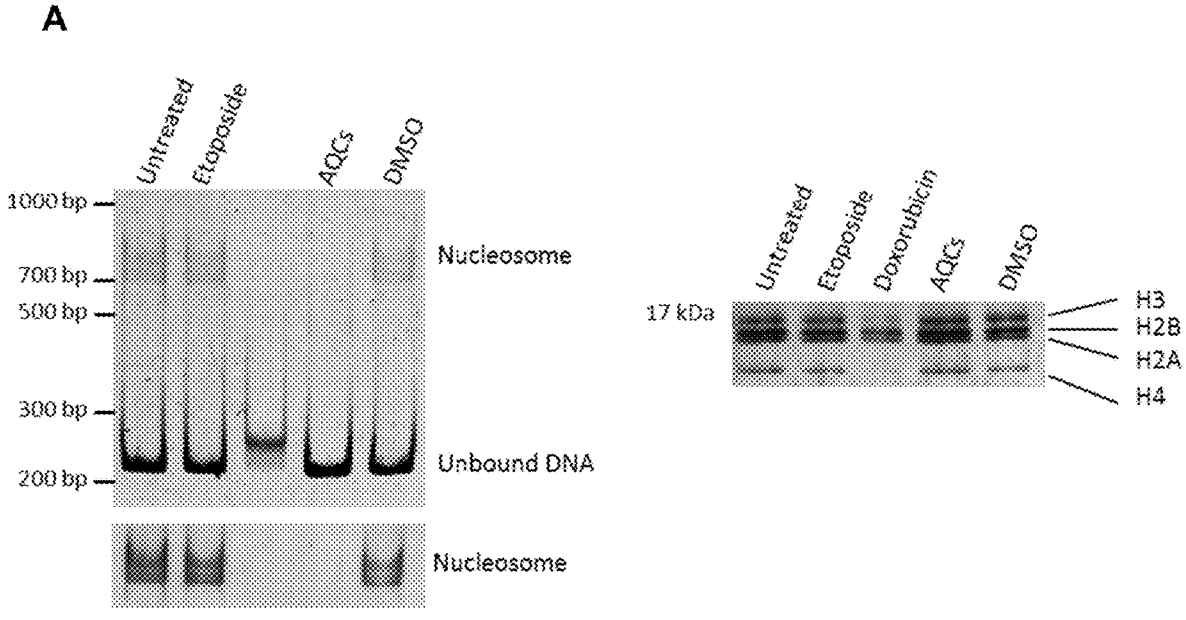
FIG. 10: Ag3-AQCs induce nucleosome destabilization. (a) Single nucleosomes were treated with etoposide (60 μM), doxorubicin (20 μM) or DMSO (vehicle) for 4 hours at room temperature, or Ag3-AQCs (AQCs, 83 ng/mL) for 30 minutes. From each reaction, half of the sample was electrophoresed under non-denaturing conditions, and the gel was stained with ethidium bromide (left, upper panel) and silver (left, lower panel). The remaining portion of the sample was analysed to check that equal amounts of histones were loaded in all cases (right panel). The position of unbound DNA, assembled nucleosomes and histones are indicated. (b) Nucleosomes were incubated with etoposide or doxorubicin as in (a) or the indicated Ag3-AQC dilutions (initial concentration, AQCs 1:10=83 ng/mL). Samples were analysed by native polyacrylamide electrophoresis, and the gel was stained first with ethidium bromide (top) and subsequently with silver (bottom) to visualize histones. This image is representative of two independent experiments.
Figure 10:
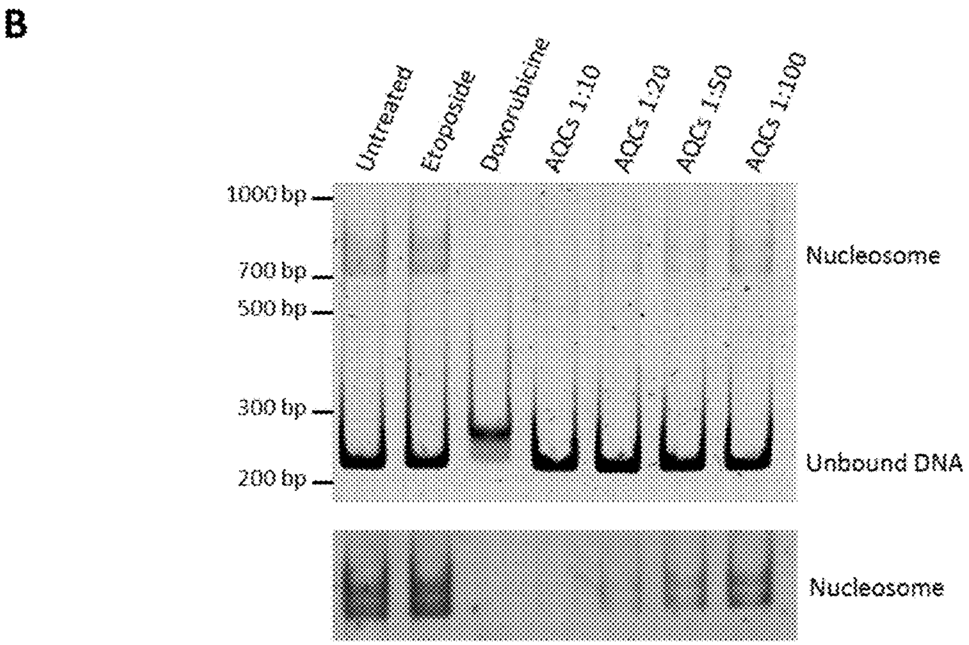

The nucleosome is the basic unit of the chromatin (Kornberg & Lorch, *Cell* 2016, 98: 285). Nucleosome assembly depends on the torsion in the DNA molecule. Doxorubicin (DOX) that modifies DNA torsion, affects nucleosomes (Yang et al. *Curr. Biol.* 2013, 23: 782 and Pang et al. *Nat. Commun.* 2013, 4: 1908). So, using DOX as a model, it was investigated whether Ag3-AQCs affect nucleosome assembly. As with DOX, Ag3-AQCs sufficed to dissociate single-nucleosome preparations (FIG. 10).

The study of Ag3-AQCs effects on single-nucleosome preparations in vitro was based on Pang et al. 2013. Single-nucleosome preparations were exposed to the Ag3-AQCs and analysed by electrophoresis.

In Vitro Single Nucleosome Assembly

Single nucleosome preparations were obtained using the Epimark Nucleosome Assembly Kit (New England Biolabs, Ipswich, USA) following the dilution assembly protocol from the manufacturer.

Gel Shift Assay

For the gel shift assay, 5% non-denaturing polyacrylamide gels were prepared using TBE buffer. After a 1 hour preliminary run at 100 V, the reactions containing nucleosomes were mixed with DNA loading buffer, and the electrophoresis was performed at 100 V for 2 h. Gels were stained with ethidium bromide to visualize DNA, and the signal was captured using the Gel Doc XR system (Bio-Rad). To detect histones, the gels were subsequently stained with silver using the PlusOne Silver Staining Kit (GE Healthcare Europe GmbH, Barcelona, Spain).

Data Analysis

Nucleosomes migrated slower than free DNA on native gels, as detected either by ethidium bromide staining for DNA (FIG. 10*a*, left, upper panel) or by silver staining for histones (FIG. 10*a*, left, lower panel). The same samples were analysed by SDS-PAGE and silver stained, showing that equal amounts of histones were loaded in all cases (FIG. 10*a*, right panel). Doxorubicin (DOX), which dissociated nucleosomes, and etoposide, which has no effect, were used as controls (Banerjee et al. *FEBS Open Bio* 2014, 4: 251). Ag3-AQCs sufficed to dissociate nucleosomes (FIG. 10*a*). Moreover, the Ag3-AQC effect on nucleosome stability is dose-dependent (FIG. 10*b*).

Example 9: Interaction Between Octamer Core Histones and Ag3-AQCs

Figure 11:
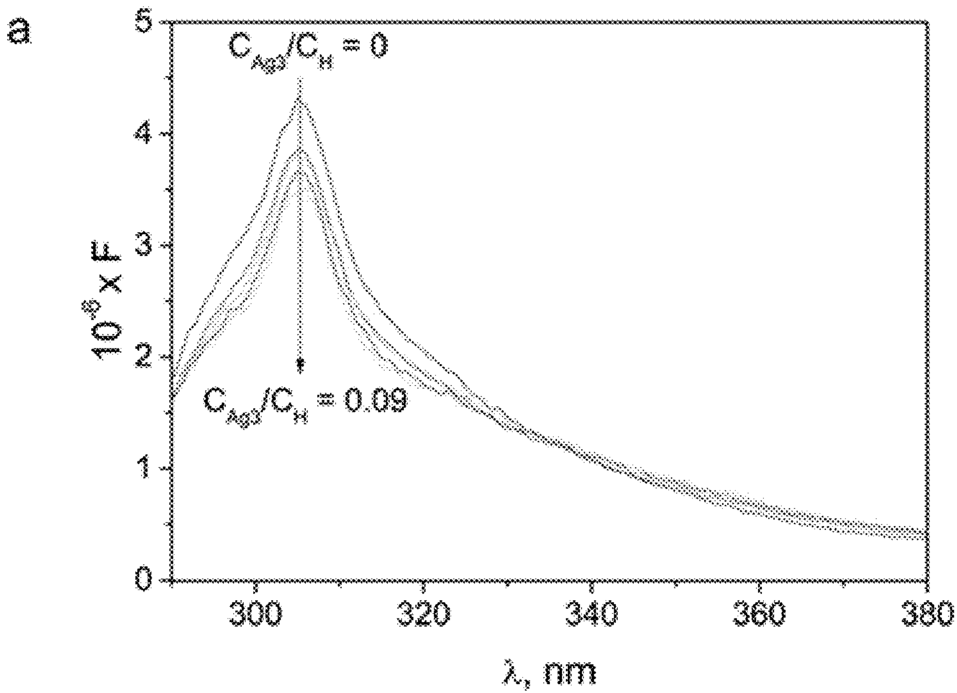
FIG. 11: Fluorescence titration spectral curves recorded for the Ag3-AQCs/H system. (a) Spectral curves, (b) Binding isotherm with line fitting of eqn. 2 to the data-pairs.
Figure 11:
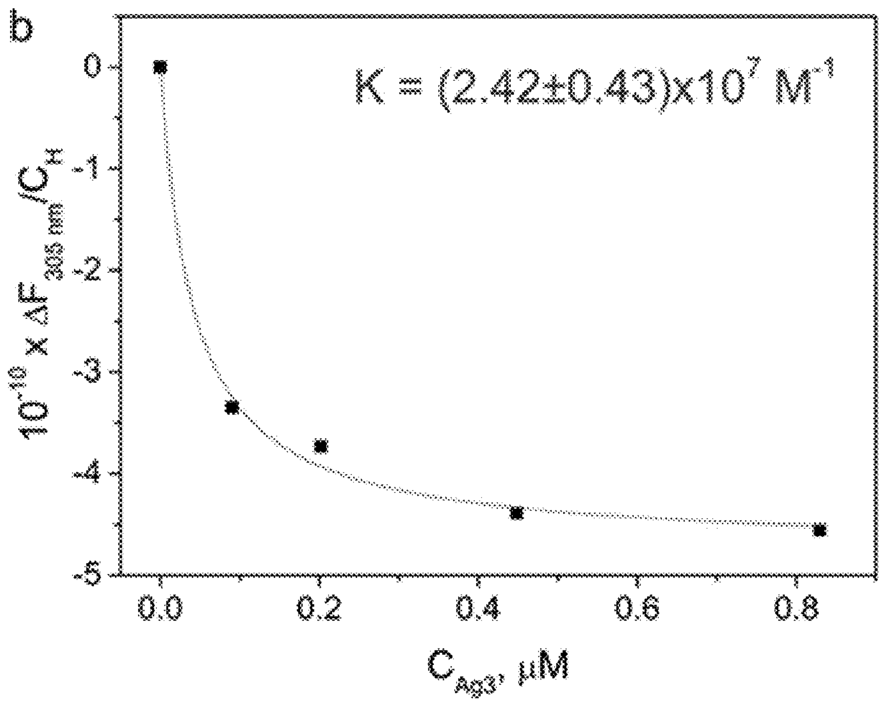
Figure 12:
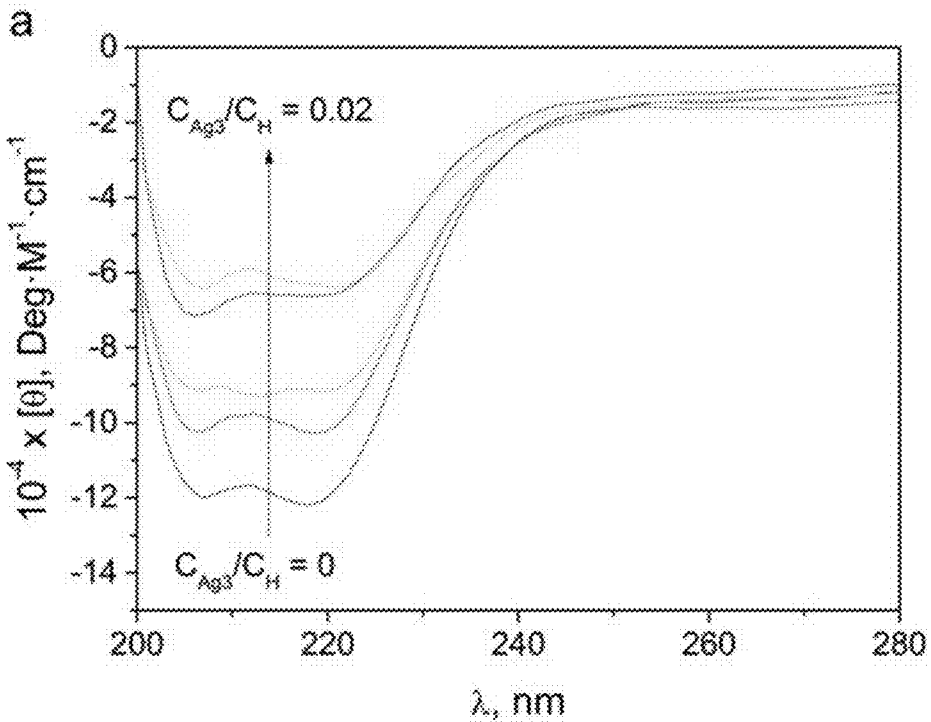
FIG. 12: CD spectral curves recorded for the Ag3-AQCs/H system. (a) Spectral curves, (b) Binding isotherm with line fitting of eqn. 2 to the data-pairs. $C_0H$=26.7 μM, $C_{Ag3\text{-}AQCs}/C_H$=0-0.02.
Figure 12:
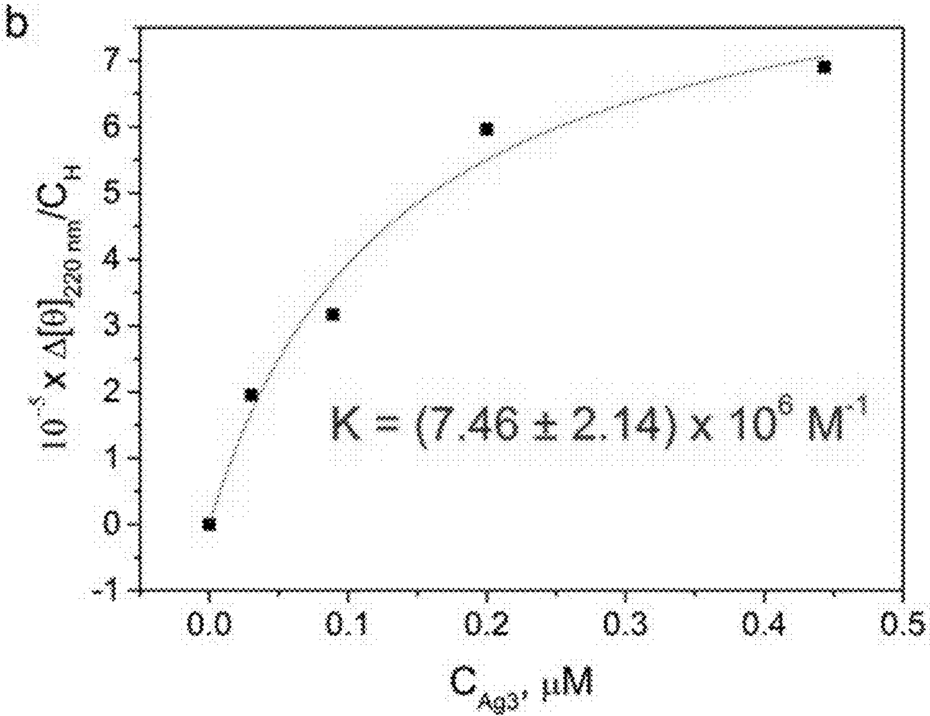

Following from Example 8, the reaction between the histone octamer and Ag3-AQCs was studied by fluorescence and circular dichroism measurements (FIGS. 11, 12). These studies indicated that Ag3-AQCs affect the histone octamer by altering the secondary structure of the octamer and causing its disaggregation. So, it was concluded that Ag3-AQCs affect nucleosome assembly in an in vitro model.

Circular Dichroism (CD) Titration

CD spectra were recorded on a MOS-450 Bio-Logic dichrograph (Seyssinet-Pariset, France) using 1.0 cm path length cells. CD titrations were carried out at 25° C. by the addition of increasing amounts of Ag3-AQCs into the cell containing the core histone solution (26.7 μM).

Fluorescence Titration

Fluorescence spectra were recorded on a FLS980 photoluminescence spectrometer (Edinburgh Instruments, Livingston, UK) at λexc=278 nm and λem=500 nm. Increasing micro amounts of Ag3-AQCs were added directly to the cell containing 13.4 μM core histone solution.

Kinetic and Thermodynamic Studies

The reaction between octamer core histones and Ag3-AQCs was studied by fluorescence and circular dichroism (CD) measurements at pH 7.0 and in phosphate buffered media. FIG. 11*a* shows the fluorescence spectral curves recorded by adding Ag3-AQCs to a 13.4 μM histones (H) solution; a quenching effect is observed due to the formation of the $Ag_3$-AQCs/H complex according to equation (eqn.) 1. FIG. 11*b* shows the decreasing isothermal titration curve recorded; saturation is achieved for 0.8 μM Ag3-AQCs content, corresponding to the concentration ratio $C_{Ag3\text{-}AQCs}/C_H=0.09$. This high affinity of Ag3-AQCs with the histone is also reflected by the large equilibrium constant, $K=(2.4\pm0.4)\times10^7\ M^{-1}$, obtained by fitting the eqn. 2 to the isotherm data-pairs:

$$Ag_3+H \overset{K}{\rightleftharpoons} Ag_3/H \quad \text{eqn. (1)}$$

$$\frac{\Delta F}{C_H} = \frac{K\Delta\phi[Ag_3]}{1+K[Ag_3]_t} \quad \text{eqn. (2)}$$

The fluorescence results were corroborated by the CD spectra recorded. FIG. 12*a* shows the diminution in the molar ellipticity of the core histones as a consequence of Ag3-AQCs addition. The clusters displayed no CD effect. Analysis of the behaviour observed at 220 nm (FIG. 12*b*) yields an isotherm that accounts for the formation of the $Ag_3$-AQCs/H complex. The data-pairs were analysed with eqn. 2, replacing ΔF by Δ[θ] and Δϕ by Δϑ. The value obtained, $K=(7.5\pm2.1)\times10^6\ M^{-1}$, is only somewhat lower than that obtained from fluorescence measurements. ΔF and A[θ] represent, respectively, the change in fluorescence and molar circular dichroism during the titration. $\Delta F=F-\varphi_H C_H$ and $\varphi_H=F^0/C_H$, where $F^0$ denotes the fluorescence of the pure histone solution. A first estimate of $\Delta\varphi=\varphi_{Ag3/H}-\varphi_H$ is obtained from the amplitude of the titration curve. The final values of Δφ and K were obtained by an iterative procedure. A similar procedure was applied to $\Delta[\theta]=[\theta]-\vartheta_H C_H$, where $[\theta]=3298.2\ (\varepsilon_L-\varepsilon_R)(\text{deg}\times\text{cm}^2\times\text{mol}^{-1})$, being $\varepsilon_L$ and $\varepsilon_R$ the absorptivities of the left-hand and right-hand circularly polarized light, respectively; $\vartheta_H=[\theta]^0/C_H$, being $[\theta]^0$ the value of [θ] for the pure histone solution; and $\Delta\vartheta=\vartheta_{Ag3/H}-\vartheta_H$.

This outcome reveals that Ag3-AQCs displays a dual behaviour; on one hand, intercalating into DNA and, on the other hand, interacting with histones. This feature is quite rare when dealing with small molecules. It was interesting to compare Ag3-AQCs with the classical recognised intercalators ethidium bromide (EB) and propidium iodide (IP) (Banerjee et al. 2014). Comparison of Ag3-AQCs and EB stress that both species intercalate into DNA with close affinity constants, $K_{EB/DNA}=(1.4\pm0.4)\times10^5M^{-1}$ and $K_{A93\text{-}AQCs/DNA}=(7.9\pm0.7)\times10^4\ M^{-1}$ (see Meyer-Almes & Porschke, *Biochemistry* 1993, 32: 4246 and Buceta et al., 2015, respectively), the two constants obtained under similar conditions by stopped-flow measurements. Regarding the interaction with histones monitored by ITC and Fluorescence measurements, they calculated the formation constants at 25° C. for the EB/octamer and IP/octamer complexes, being $K_{EB/octamer}=1.9\times10^5\ M^{-1}$ and $K_{IP/octamer}=1.4\times10^5\ M^{-1}$, with only negligible difference between the values for low and high ionic strengths. These constants were two orders of magnitude lower than those of the Ag3-AQCs/octamer system, indicating that the interaction whit octamer could be of different nature.

As with Ag3-AQCs, the fluorescence displayed by octamer was quenched upon addition of EB and IP; however, addition of EB to the octamer (not shown with IP), does not alter the CD spectra of the octamer, even under conditions in which EB is 12-fold in excess regarding the histone, that is, $C_{EB}/C_H=12$. Such behaviour was attributed to the fact that EB does not cause any secondary structure perturbation of the histone proteins of the octamer. FIG. 12*a* reveals strong variations in the CD spectral curves of the histone caused by addition of very small amounts of Ag3-AQCs, reaching saturation for $C_{Ag3\text{-}AQCs}/C_H\approx0.02$, which indicates that the effect of Ag3-AQCs on the octamer is enormous. By comparison with EB, one can deduce that Ag3-AQCs affects the core of the histones by altering the secondary structure of the octamer and disaggregating it, probably due to the high affinity of the $Ag_3$-AQCs with the fragments formed.

Example 10: Imaging the Effect of Ag3-AQCs in Chromatin Organization

Figure 13:
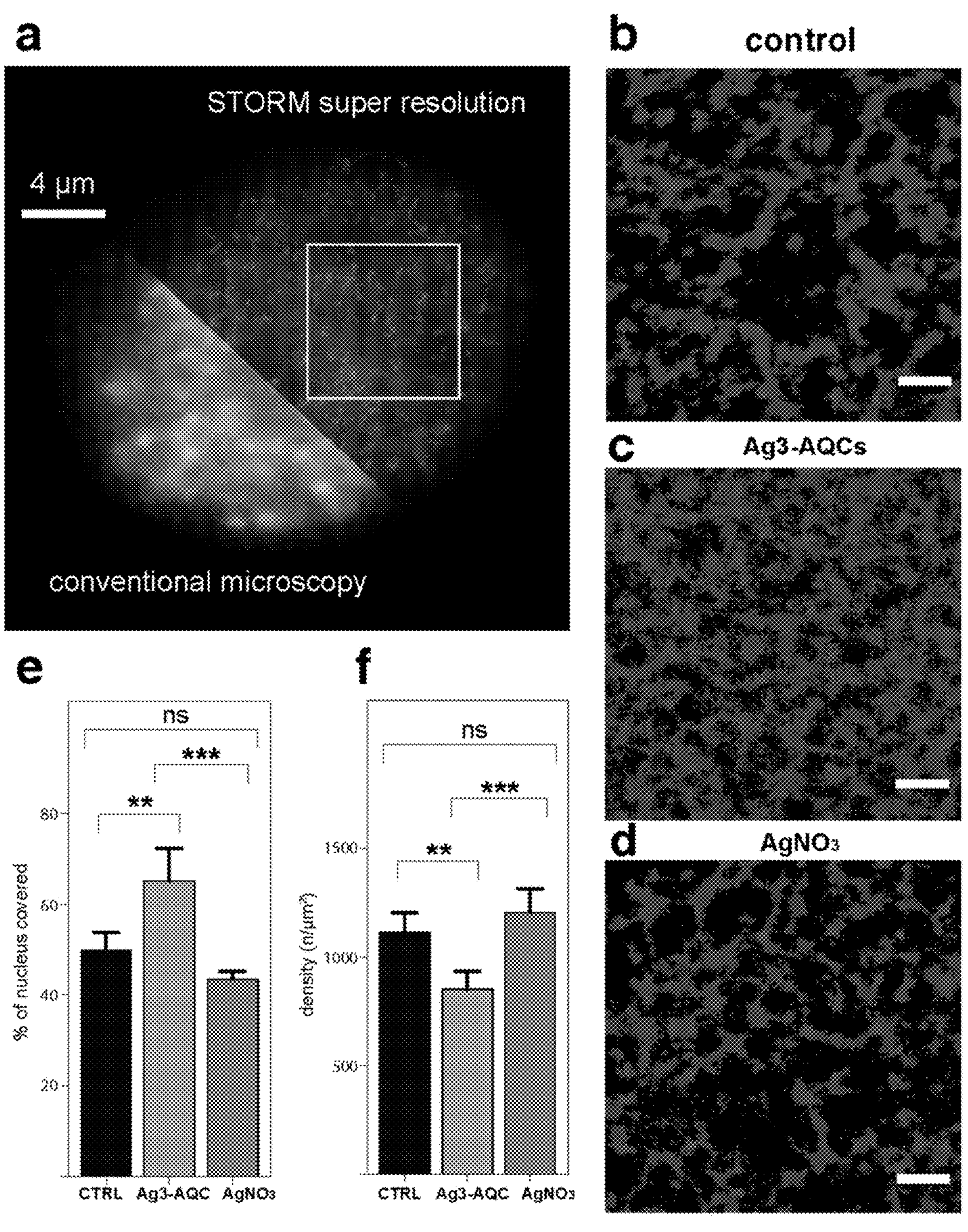
FIG. 13: Direct visualization of chromatin accessibility using STORM super resolution microscopy. (a) Representative image of a nucleus containing fluorescent EdU, imaged using both conventional microscopy (scale bar 4 μm) and STORM super resolution (scale bars 2 μm). (b-d) Representative reconstructed STORM image of the chromatin in cells in untreated conditions (b), after treatment with Ag3-AQCs (c) and after treatment with free silver cations (d). (e) Quantification of the percentage of nuclear area covered by the chromatin. (f) Quantification of the chromatin density.

To investigate whether the results presented in Examples 8 and 9 have a similar effect on eukaryotic cells, super-resolution STORM (stochastic optical reconstruction microscopy) on intact nuclei of A549 proliferating cells was performed to directly visualize the effect of Ag3-AQCs in chromatin organization in A549. By localizing the position of individual fluorophores with nanometric precision on sequential sets of images, STORM can provide an effective resolution of around 20 nm (Rust et al. *Nat. Methods* 2006, 3: 793). Using this technique, several research groups have visualized the complexity and organization of chromatin at the single cell level (Zessin et al. *J. Struct. Biol.* 2012, 177: 344; Ricci et al. *Cell* 2015, 160: 1145; Lakadamyali & Cosma, *FEBS Lett.* 2015, 589: 3023; and Boettiger et al. *HHS Public Access* 2016, 529: 418). Newly replicated DNA labelled with EdU-AF6472 (FIG. 13*a*) was visualized in the presence and absence of Ag3-AQCs, as well as in the presence of free silver cations ($AgNO_3$) as a blank (FIG. 13*b-d*). The STORM images show a striking change of chromatin compaction upon the addition of the Ag3-AQCs. Whereas in control cells the chromatin is contained in highly compact regions (grey spots) (FIG. 13*b*), addition of the Ag3-AQCs leads to a massive de-compaction of these regions (FIG. 13*c*). Quantification of STORM images on multiple cells shows that the chromatin occupies a larger percentage of the nuclear area (FIG. 13*e*) and that chromatin density decreases as a result of the Ag3-AQCs treatment (FIG. 13*f*), consistent with chromatin de-compaction. These differences were specific to Ag3-AQCs treatment, since the blank with silver cations did not affect chromatin compaction (FIG. 13*d-f*).

STORM Imaging Sample Preparation $1.5\times10^4$ A549 cells were plated on 8-well Lab-tek cover glass chamber (Nunc) and 24 hours later cells were synchronized in S phase by adding 0.8 mM hydroxyurea (H-8627, Sigma) to the culture medium. After an overnight incubation, cells were washed twice with serum-free medium and incubated with $Ag_3$-AQCs (55.61 ng/mL) or $AgNO_3$ (5 μM) in serum-free medium for 30 min. The medium was removed and replaced with complete medium containing EdU (20 μM) for 2 hours. Cells were then fixed and permeabilized with Methanol-Acetone (1:1) solution at 20° C. for 10 minutes and blocked (3% BSA+0.01% Triton X-100) for 1 hour at RT. Finally, cells were washed three times with PBS and stained with Alexa Fluor 647 following the instructions provided by the manufacturer (Click-iT® EdU Alexa Fluor®488 Imaging Kit, Thermo Fisher Scientific).

STORM Imaging

The chromatin was imaged using a commercial microscope system from Nikon Instruments (NSTORM). First, 647 nm laser light at maximal power density was used for 15 minutes to bring the large majority of AlexaFluor647 molecules attached to EdU to the dark state. Subsequently, image sequences of 50000 frames were acquired using continuous 647 nm laser excitation to directly excite AlexaFluor647, and at the same time 405 nm laser light (5%, 30 μW) was used to reactivate the dye into a fluorescent state (dSTORM). Imaging was done using a previously described imaging buffer (Cysteamine MEA [SigmaAldrich, #30070-50G], Glox Solution: 0.5 mg/mL glucose oxidase, 40 mg/mL catalase [all Sigma], 10% Glucose in PBS), see Bates et al. Science 2007, 317: 1749. Representative images of nucleus containing fluorescent EdU were taken using both, conventional microscopy and STORM super resolution. In conventional microscopy images (FIG. 13*a*), the square represents the size and typical location of the zoom-in images for STORM imaging. In reconstructed STORM images magenta spots represent single x-y localizations, while dark areas correspond to regions deprived of chromatin. All images are 50 $\mu m^2$ in size typically representing about ⅓ of the nucleus as shown by the yellow square in FIG. 13*a*, and contain the same number of localizations allowing for reliable visual determination of differences in chromatin accessibility.

Data Analysis

STORM images were analysed and rendered as previously described in Bates et al. 2007. Briefly, spots in single-molecule images were identified based on a threshold and fit to a Gaussian to identify their position in x and y. Applying this approach over all 50000 frames gives the raw STORM data, consisting of a list of x-y coordinates, corresponding to the localized positions of all the fluorophores. Reconstructed images from the x-y coordinates were displayed using Insight3, after drift correction.

Since the labelling density of the EdU was very high, all of the images were roughly normalized to the same number of localizations per $\mu m^2$ of the nucleus, by varying the number of frames used in the final reconstructed image. The percentage of non-zero pixels of the reconstructed images was then calculated in ImageJ, and the percentage of nuclear area covered by EdU also calculated. The density of chromatin per $\mu m^2$ was extracted by dividing the number of localizations (same for each recorded nucleus) over the chromatin-covered area.

Figure 14:
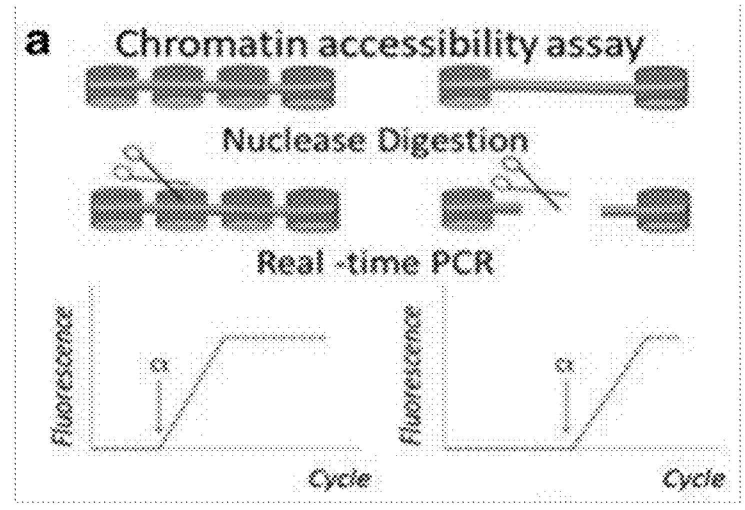
FIG. 14: Ag3-AQCs increase chromatin accessibility. (a) Schematic procedure of the chromatin accessibility assay. (b-e) ΔCt graphs of: proliferating cells (b); serum-deprived A549 cells (c); lung tumour sample (d); and kidney sample (e).
Figure 14:
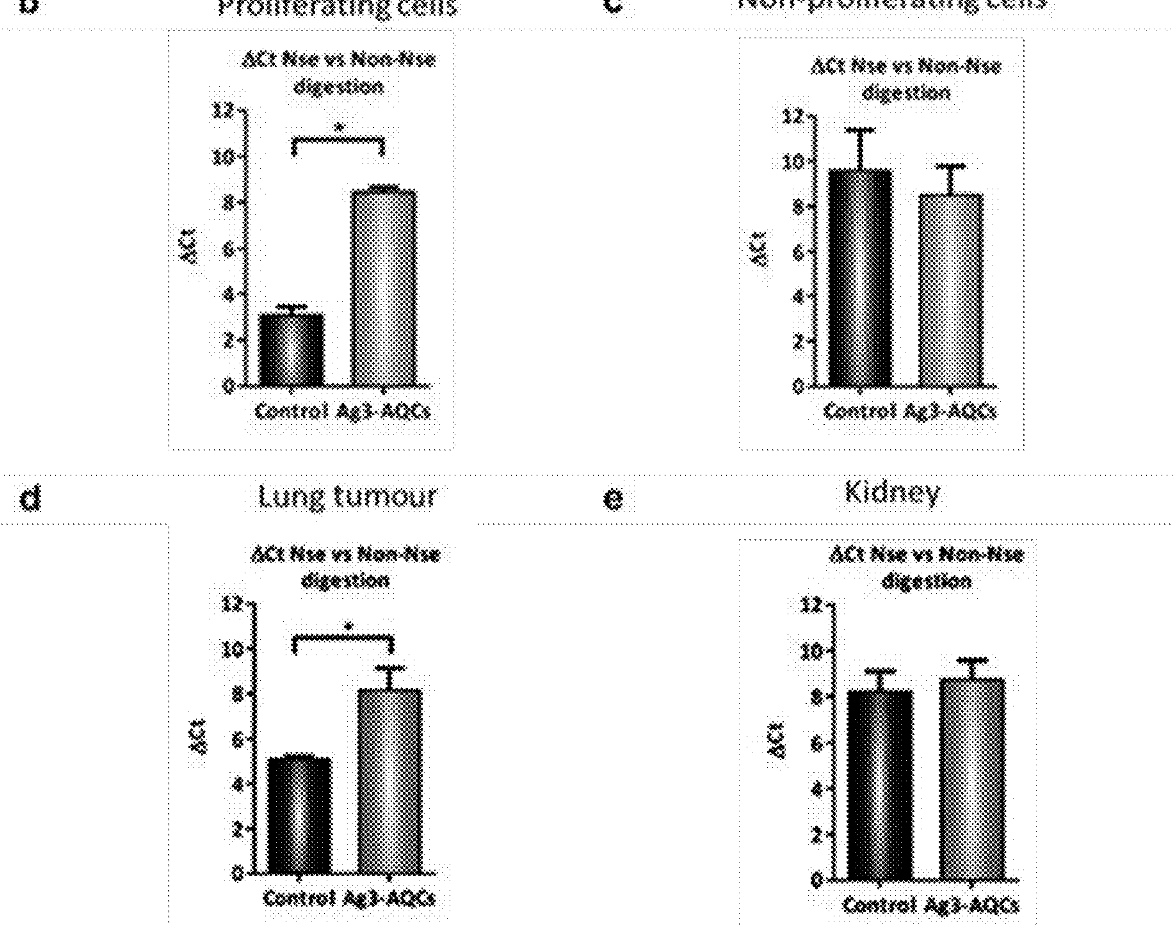

Example 11: Investigating the Effect of Ag3-AQCs Using Chromatin Accessibility Assay A nuclease-hypersensitive approach (Gross & Garrard, *Annu. Rev. Biochem.* 1988, 57: 159) in combination with a real-time PCR (qPCR) assay (Rao et al. *J. Immunol.* 2001, 167: 4494) across the region of the housekeeping gene, GAPDH, was used to further explore whether Ag3-AQCs have an effect not only in cells but also in multicellular organisms. The presence of nucleosomes can be identified based on accessibility of DNA to exogenous nucleases ((Kornberg & Lorch 2016). The DNA, protected by the nucleosome, is inaccessible to exogenous nucleases and becomes available for subsequent qPCR amplification with insignificant threshold cycle (Ct) shifts between digested and undigested samples; Ct is a relative measure of the concentration of the target in the qPCR reaction. In contrast, DNA outside the nucleosome is accessible to nucleases and susceptible to digestion; this DNA becomes unavailable for qPCR, with a large Ct shift between digested and undigested samples. A schematic diagram of the experimental approach adopted is outlined in FIG. 14*a*. A549 proliferating cells presented an enhanced accessibility of chromatin to external nucleases, as shown by the Ct shift between treated and untreated cells (FIG. 14*b*). The difference in Ct (ΔCt) between nuclease-digested versus non-digested DNA samples from Ag3-AQC-treated and control cells was also assessed. When samples were not digested, Ag3-AQC-treated cells and controls had similar Ct values; after digestion Ag3-AQC-treated cells had significantly higher Ct values, increasing the ΔCt (FIG. 14*b*) and supporting the view that Ag3-AQCs induced chromatin de-compaction and thus facilitating nuclease digestion. Moreover, nuclease-hypersensitive approach and STORM images gave compatible results supporting nuclease-hypersensitive approach as a valid method to study chromatin organization.

Because of genome-wide alterations to chromatin structure that occur during DNA replication (Groth et al. *Cell* 2007, 128: 721), it was investigated whether the Ag3-AQC effects were affected by replication. To that end, experiments were repeated in cells that were serum-deprived for 72 hours to arrest them before the S-phase of the cell cycle. Notably, the differences found between Ag3-AQC-treated and non-treated cells disappeared (FIG. 14*c*), indicating that Ag3-AQC-mediated enhancement of chromatin accessibility is restricted to proliferating cells (for a more detailed discussion see Example 13).

To explore the action of Ag3-AQCs in mice, it was reasoned that if actively proliferating cells showed enhanced chromatin accessibility after Ag3-AQC treatment, Ag3-AQCs would be more active in tumours than in normal tissues, whose cells are mostly quiescent. To examine that possibility, an orthotopic lung tumour was induced in mice and chromatin accessibility in lung tumour and kidney samples 24 hours after Ag3-AQC administration was assayed. Notably, chromatin accessibility was significantly augmented after the treatment in tumour samples (FIG. 14*d*), but not in the kidneys (FIG. 14*e*).

Example 12: Combination of Ag3-AQCs and Cisplatin

To confirm the effects of Ag3-AQCs on chromatin accessibility, a different experimental approach was used. The effect of co-administration of Ag3-AQCs with cisplatin (CDDP) was studied. Only about 1% of intracellular CDDP binds to nuclear DNA (Gonzalez et al. *Mol. Pharmacol.* 2001, 59: 657), suggesting poor accessibility. Thus, it was reasoned that the Ag3-AQC effect on chromatin accessibility could be used to augment CDDP binding to DNA. It was found that Ag3-AQCs co-administration increased the amount of CDDP bound to DNA in A549 cells approximately threefold (FIG. 15*a*). Moreover, this effect was present in proliferating cells, but not in serum-deprived, non-proliferating cells (FIG. 15*a*), thus implying that it is mediated by an increase in chromatin accessibility, which is itself mediated by Ag3-AQCs. Interestingly, DOX, which induces histone eviction, did not increase CDDP binding to DNA (FIG. 15*a*).

Figure 16:
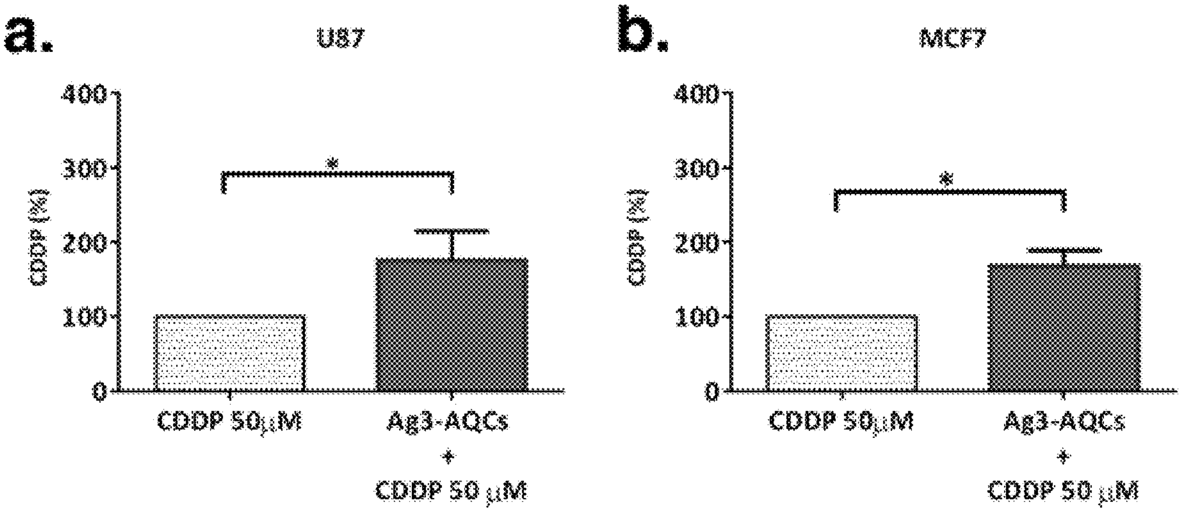
FIG. 16: Co-administration of Ag3-AQCs and CDDP increase the amount of platinum bound to DNA in (a) glioblastoma (U87) and (b) breast adenocarcinoma (MCF7) cell lines. Cells were treated with Ag3-AQCs (83 ng/mL) for 1 hour and with CDDP (50 μM) for 24 hours more. After that, cells were collected, DNA extracted, and the amount of platinum quantified by mass spectrometry. Data represent mean±SD of 2 independent experiments with 3 replicas per experiment. Mann Whitney test ((*) $p<0.01$).

The effect of Ag3-AQC on increasing CDDP bound to DNA was confirmed in other human cell lines, including glioblastoma (U87) and breast adenocarcinoma (MCF7) (FIG. 16).

The Ag3-AQC effect was also investigated in animals bearing a lung tumour. The effect of administering CDDP alone or co-administered with Ag3-AQCs, on the amount of CDDP bound to DNA in the lung (containing the tumour) and in other mouse organs (selected by being potential targets of undesired CDDP side effects) was compared. A single administration of CDDP in combination with Ag3-AQCs to tumour-bearing mice, when compared with the administration of the same dose of CDDP alone, increased the amount of CDDP bound to DNA by a factor of 5.5 only in the lung, without affecting the amount of CDDP bound to DNA in the other organs (FIG. 15*b*).

Figure 17:
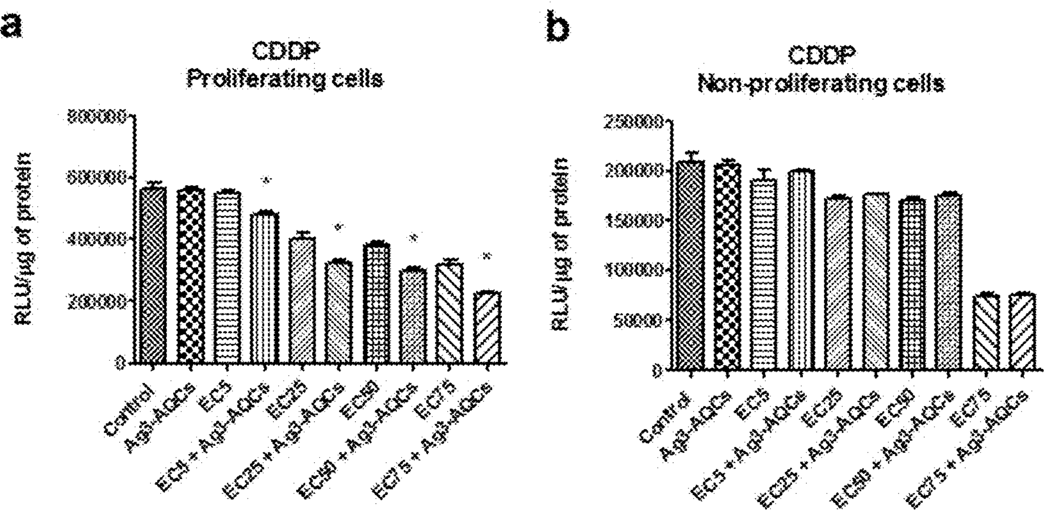
FIG. 17: Co-administration of Ag3-AQCs and DNA-acting drugs. A549 Luc-C8 cells were seeded in 96 well plates and 24 hours (proliferating cells) (a) or 72 hours (non-proliferating cells) (b) later were treated with 1) Ag3-AQCs (55.61 ng/mL) in serum free medium for 1 hour and 24 hours more in complete medium, 2) Ag3-AQCs (55.61 ng/mL) in serum free medium for 1 hour and 24 hours more with different doses of CDDP (EC5: 5 μM, EC25: 10 μM, EC50: 50 μM and EC75: 100 μM). After that, cells were lysed and the amount of protein was quantified using a Bradford colorimetric method and luminescence was measured using a Lumat BL 9507 luminometer (Berthold Technologies). Results were expressed as relative luminescence units (RLU) per μg of extracted protein. (c) The percentage of cell death caused by Ag3-AQCs co-administration was assessed considering that CDDP alone was 100% (control). Data represent mean±SD of 2 independent experiments with 3 replicas per experiment. Mann Whitney test ((*) $p<0.01$). (d) In another set of experiments CDDP was substituted by carboplatin (EC5: 0.25 μM, EC25: 0.5 μM, EC50: 1 μM and EC75: 2 μM) or oxaliplatin (EC5: 2.5 μM, EC25: 12.5 μM, EC50: 50 μM and EC75: 200 μM) with similar results found for CDDP.
Figure 17:
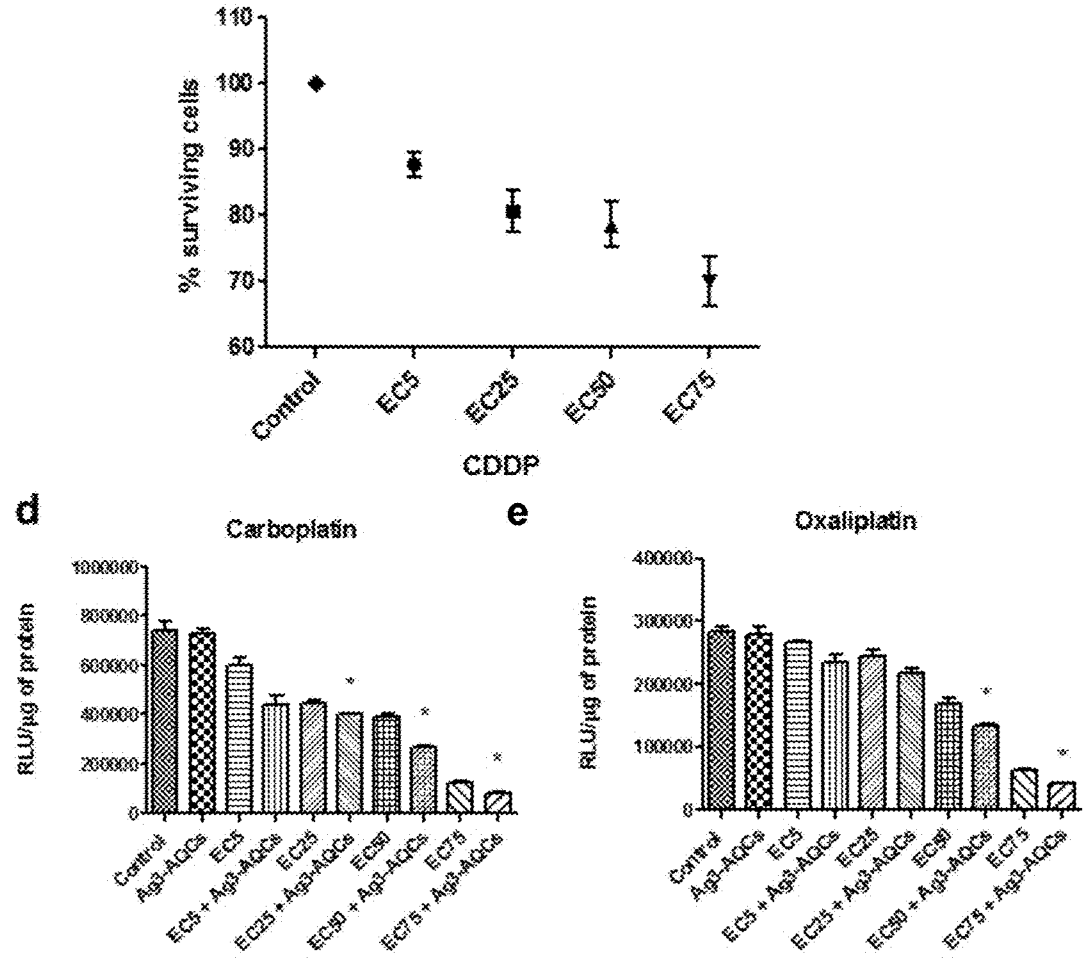

Although CDDP exerts anticancer effects via an intertwined signalling pathway (Galluzzi et al. *Cell Death Dis.* 2014, 5: e1257, and Galluzzi et al. *Oncogene* 2012, 31: 1869), DNA binding is still considered the main mechanism responsible for tumour cell demise (Hall et al. *Annu. Rev. Pharmacol. Toxicol.* 2008, 48: 495). To check whether Ag3-AQCs and CDDP co-administration had an effect on cell demise, cell viability was assessed and it was found that it was differently affected when CDDP was administered alone or with Ag3-AQCs in proliferating cells (FIG. 15*c*), but not in the serum-deprived, non-proliferating cells (FIG. 15*d*). This result indicates that Ag3-AQCs action is mediated by enhanced chromatin accessibility to CDDP. Additionally, Ag3-AQCs actions are cell-cycle specific and dependent on CDDP concentration (see also Example 13, and FIG. 17).

Figure 18:
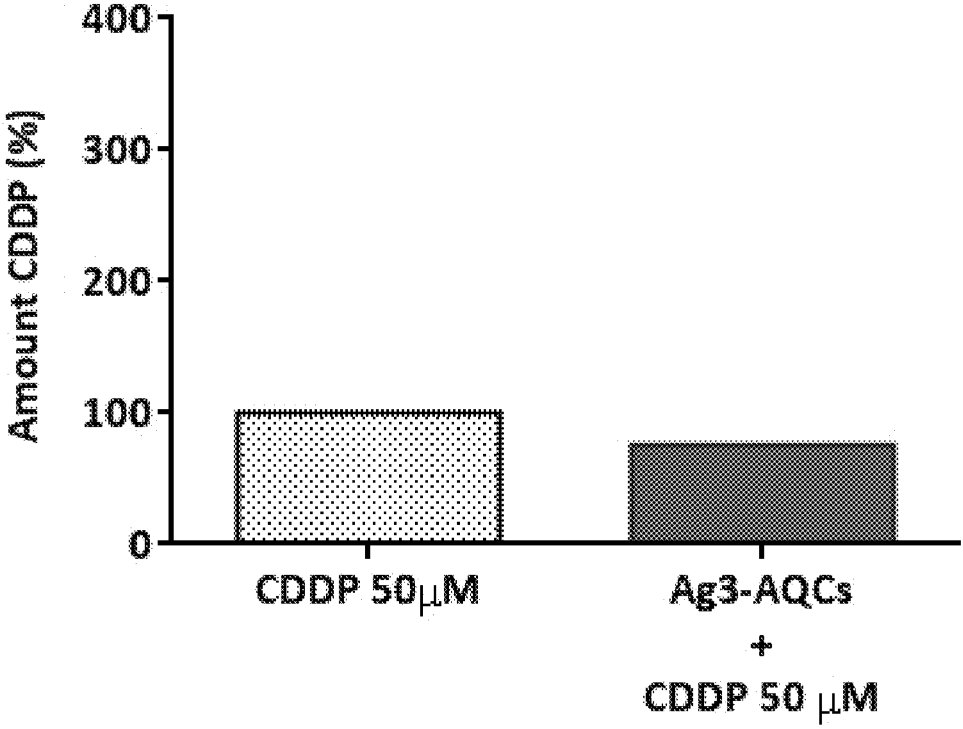
FIG. 18: Mass spectrometry quantification of CDDP bound to DNA in cell cultures pre-treated with medium or Ag3-AQCs (83 ng/mL) for 1 hour and after 24 hours with CDDP (50 μM) for 24 hours more.

The lack of effects of Ag3-AQCs on gene expression and DNA damage (see Examples 15 and 16) could be the result of Ag3-AQCs short-lived effect inside the cell. Unfortunately, there is no available technology that allows for Ag3-AQCs quantification in biological samples, thus precluding pharmacokinetics studies, but the duration of Ag3-AQCs effect can be indirectly estimated using increased chromatin accessibility to CDDP as a surrogate marker of the Ag3-AQC effect. Ag3-AQCs increased CDDP incorporation into DNA when CDDP and Ag3-AQCs were administered simultaneously, but not when CDDP administration was delayed 24 hours after Ag3-AQCs administration, indicating that the Ag3-AQC effect is transitory (FIG. 18). Similar results were obtained when cell viability was used as an endpoint, instead of CDDP bound to DNA (FIG. 15*e*). Therefore, it can be concluded that the Ag3-AQC action inside the cell was transient.

Example 13: Ag3-AQCs Actions are Cell-Cycle Specific and Dependent on CDDP Concentration Two complementary reasons can explain that Ag3-AQCs increase the mortality of only a fraction of the cells when administered with CDDP (FIG. 15*c*). One is dependent on the amount of CDDP present inside the cell. The mortality of cells will depend on the intracellular CDDP levels; accordingly, the cells can be found distributed in three groups: 1) cells having enough CDDP to die independently of the presence of Ag3-AQCs; 2) cells with intermediate levels of CDDP that will solely die in the presence of Ag3-AQCs; and 3) cells with very low levels of CDDP that will survive either way. The other reason relies on that Ag3-AQCs act only in a cell-cycle phase, in this case the S-phase. Only those cells that are in the right phase will benefit from the treatment with Ag3-AQCs. To check both explanations, concentrations of CDDP alone or with Ag3-AQCs were given to proliferating and non-proliferating A549 cells. As shown, non-proliferating cells do not benefit from Ag3-AQCs and the Ag3-AQCs effect is stronger with higher doses of CDDP (see FIGS. 17*a-c*), thus supporting that Ag3-AQCs actions are cell-cycle specific and dependent on CDDP concentration.

The results clearly indicate that the Ag3-AQCs effect on access to chromatin depends upon the cell cycle stages; in fact, it is restricted to the S-phase. This effect is simply explained by the direct action of Ag3-AQCs on nucleosomes. During DNA replication, every nucleosome across the genome must be disrupted and reformed when the replication fork passes (Rhind & Gilbert, *Cold Spring Harb. Perspect. Biol.* 2013, a010132). Therefore, as stated in Lucchini et al. *EMBO J.* 2001, 20: 7294, a "window of opportunity" opens after the passage of the replication fork and persists until the deposition of the first positioned nucleosome, in which the DNA is free of nucleosomes. It was speculated that Ag3-AQCs expand the temporal window when the DNA is free of nucleosomes, hence facilitating the binding of DNA-binding drugs. This hypothesis is based on the fact that nucleosome assembly depends on torsion in the DNA molecule (Gupta et al. *Biophys. J.* 2009, 97: 3150, and Yang et al. *Biochim. Biophys. Acta.* 2014, 1845: 84). Therefore, the enlargement and subsequent distortion of DNA caused by intercalation of the Ag3-AQCs, as well as the interaction with core histones, affects nucleosome assembly, retarding their deposition. In disrupting the chromatin assembly, factor I complex (a nuclear complex that assembles histone tetramers onto replicating DNA), nucleosome positioning around promoters is not altered, but nucleosome positions in newly replicated chromatin are dramatically affected (Ramachandran & Henikoff, *Cell* 2016, 165, 580). Altogether, the present data indicates that nucleosomes near replication origins are the targets of Ag3-AQCs, and, that Ag3-AQCs action is restricted to the S-phase of the cell cycle.

Example 14: Effect of AQCs on Other DNA-Acting Drugs

Figure 19:
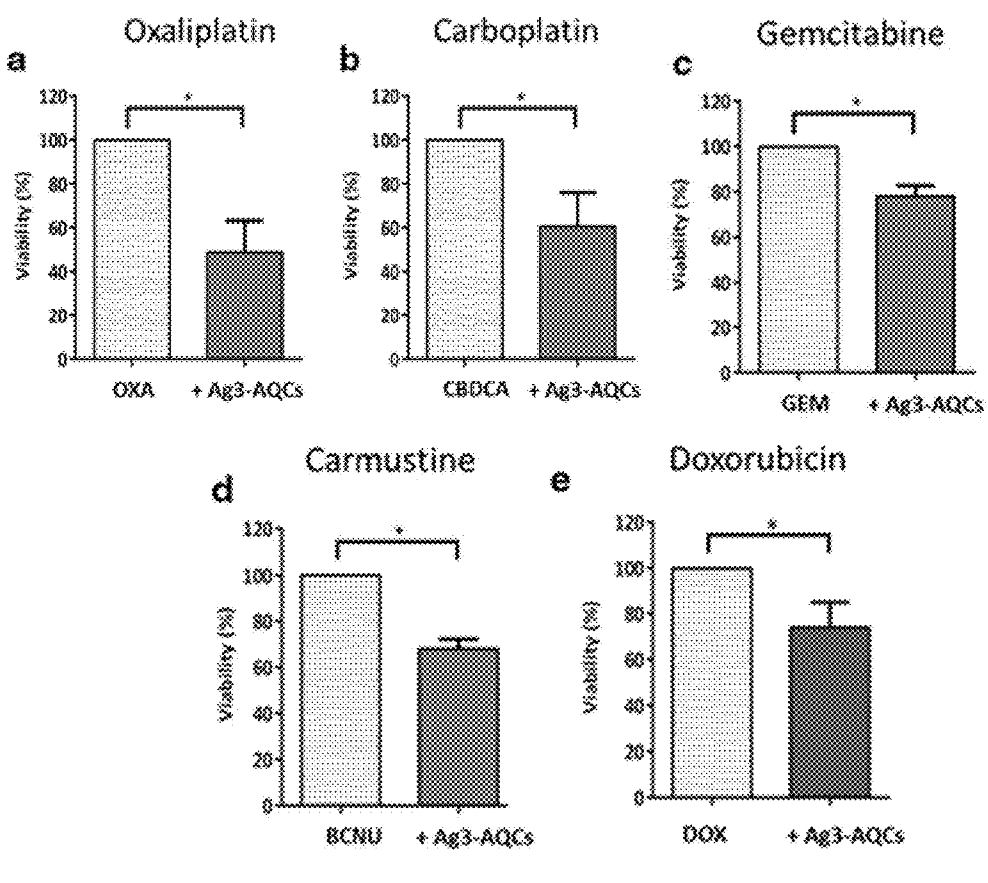
FIG. 19: Co-administration of Ag3-AQCs with DNA-binding drugs increases cell mortality. A549 cells were preincubated for 1 hour with medium or with Ag3-AQCs (83 ng/mL) and treated for 24 hours with oxaliplatin (OXA) 50 μM (a), carboplatin (CBCDA) 1 mM (b), gemcitabine (GEM) 100 μM (c), carmustine (BCNU) 400 μM (d) and doxorubicin (DOX) 7.5 μM (e), after that cell viability was measured by flow cytometry. Data represent mean±SD of 3 independent experiments with 3 replicas per experiment. Mann Whitney test ((*) $p<0.01$). (f) Intracellular DOX uptake measurement. Left: Flow cytometric profile of A549 cells treated with DOX (7.5 μM) for 4 hours or pre-treated with Ag3-AQCs (83 ng/mL) for 30 minutes and DOX (7.5 μM) for 4 hours. Right: Fluorescence microscopy images of A549 cells treated with DOX (3.75 μM and 7.5 μM) for 30 minutes or pre-treated with Ag3-AQCs (83 ng/mL) for 30 minutes and DOX (3.75 μM and 7.5 μM) for another 30 minutes.
Figure 19:
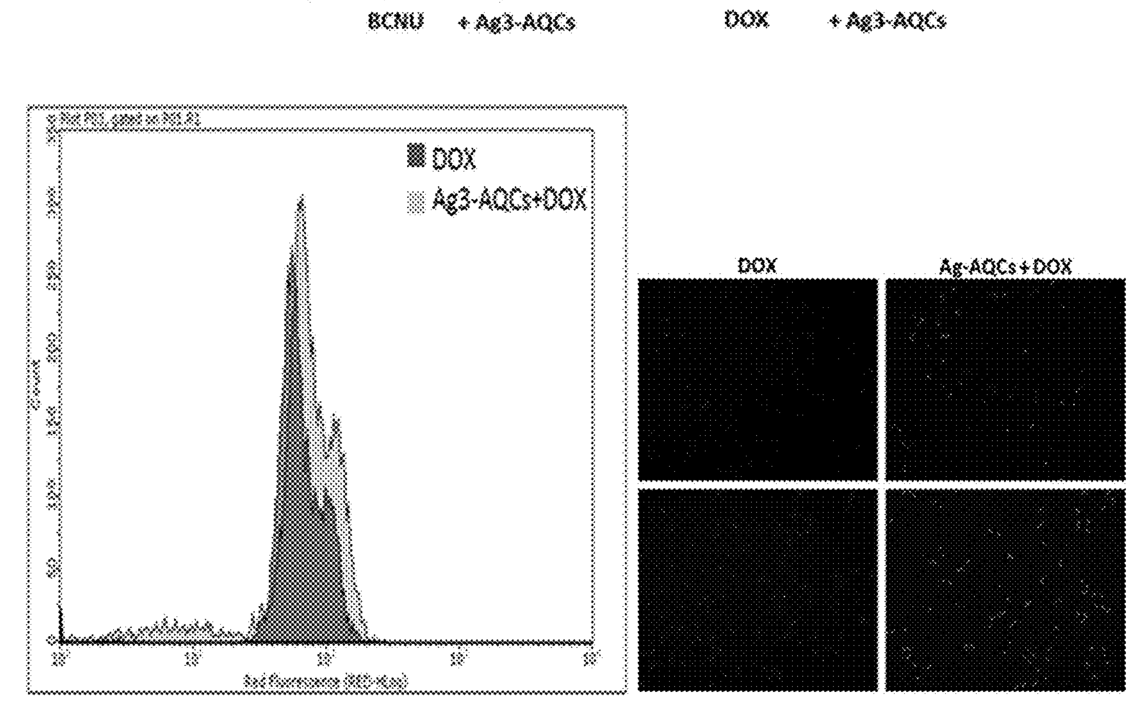

It was reasoned that the effect of Ag3-AQCs on chromatin accessibility could benefit other DNA-acting drugs. To this end, drugs related to CDDP, such as oxaliplatin (OXA) and carboplatin (CBDCA), were tested and it was found that Ag3-AQCs also increased their cytotoxicity (FIG. 17*d*, 19*a, b*). Other anticancer drugs that can interact with DNA, such as carmustine (BCNU) and doxorubicin (DOX), were also affected (FIG. 19*d, e*). Moreover, the fluorescence of DOX was used to confirm that Ag3-AQCs boosted DOX accumulation in nuclei, supporting the observation that Ag3-AQC co-administration enhances the accessibility of the drug to DNA (FIG. 19*f*).

Interestingly, gemcitabine (GEM), a nucleoside analogue incorporated into growing DNA strands, showed a greater effect on cell demise when co-administered with Ag3-AQCs (FIG. 19*c*), supporting that Ag3-AQCs are acting on the vicinity of the replication foci to facilitate GEM incorporation into newly synthesized DNA.

Example 15: Analysis of Gene Expression

Perturbations of the assembly of nucleosomes and their dynamics have led to genome function defects, including aberrant gene expression (Gross & Garrard, 1988). Hence, an imperative concern was to know whether Ag3-AQCs do affect gene expression. To this end, a high-density microarray analysis was conducted to measure gene expression levels at 0, 4 and 24 hours after Ag3-AQC treatment (see the Materials sections). No significant differences were found in individual gene expression, either between treated and untreated groups or between the same groups at different times (significance was designated when the FDR (false discovery rate) p-value was <0.05). In summary, these results indicate that Ag3-AQCs do not significantly affect gene expression.

Example 16: Analysis of DNA Damage

The question still arises as to whether Ag3-AQCs may cause DNA damage. To explore this, it was investigated whether Ag3-AQCs inside the cells could induce DNA strand breaks. For that purpose, flow cytometry was used to assess the effect of Ag3-AQCs on phosphorylate histone H2AX (pH2AX) expression, a marker of DNA damage (Sharma et al., in DNA Repair Protocols, (Ed: L. Bjergbæk), Springer Science, New York, 2012, Ch. 40). Ag3-AQCs did not increase pH2AX over control levels (FIG. 20*a*), but, as described for DOX (Pang et al. 2013), it was noted that Ag3-AQCs could induce the eviction of pH2AX, thus masking the DNA-damage effect. To verify that this was not the case, Ag3-AQCs were co-administered with etoposide, a well-characterized DNA-damaging agent (Pommier et al. 2010). The resulting pH2AX expression was assessed without finding that Ag3-AQCs decreased pH2AX expression (FIG. 20*a*). Therefore, the absence of an Ag3-AQCs effect on pH2AX expression is not due to greater eviction of pH2AX but rather to the absence of DNA damage. Using a DNA Comet assay (Collins, *Mol. Biotechnol.* 2004, 26: 249), a different method to test for DNA damage, it was found that Ag3-AQCs has no effect on DNA damage (FIG. 20*b*).

Example 17: In Vivo Anti-Cancer Efficacy

For in vivo anti-cancer efficacy, Ag3-AQCs effectiveness in an A549 orthotopic lung cancer model was assessed. Tumour growth was observed in vivo by measuring the bioluminescence of tumour cells from the time of injection of tumour cells to 37 days after injection. Control animals showed gradual tumour growth up to the end of the experiment. CDDP (4 mg/kg) intravenously injected in the tail vein significantly reduced the growth of tumours; co-administration with Ag3-AQCs (0.01 mg/kg) potentiated this effect (FIG. 21*a*). It is worth noting that Ag3-AQCs did not affect the body weight of the animals (FIG. 21*b*), thus excluding severe toxicity and indicating that the clusters did not increase CDDP toxicity when co-administered. At 37 days, the animals were sacrificed, protein was extracted from the lungs and mediastinal nodes, and the luciferase activity, only present in tumour cells, was measured. CDDP significantly reduced lung and mediastinal node luciferase levels compared to the control group. Again, the co-administration of CDDP with Ag3-AQCs had the strongest effect (FIG. 21*c*). Mouse lungs were stained with a monoclonal antibody against a human cytokeratin. Only A549 tumour cells of human origin were stained (FIG. 21*d*). Notably, the co-administration of CDDP with Ag3-AQCs had the strongest effect on reducing the size of tumour foci, confirming the findings related to the luciferase levels.

All patents and patent applications referred to herein are incorporated by reference in their entirety. Furthermore, all embodiments described herein may be applied to all aspects of the invention.

The invention claimed is:

1. A composition purified by a process of purifying atomic quantum clusters (AQCs) consisting of 3 or fewer zero-valent transition metal atoms comprising:

(i) applying a solution comprising a mixture of AQCs to a separation medium, wherein said separation medium either binds AQCs consisting of more than 3 zero-valent transition metal atoms, or binds AQCs consisting of 3 or fewer zero-valent transition metal atoms; and (ii) isolating AQCs consisting of 3 or fewer zero-valent transition metal atoms in solution, wherein said composition is free of AQCs consisting of more than 3 zero-valent transition metal atoms.

2. An aqueous composition consisting of atomic quantum clusters (AQCs) in aqueous solution, the AQCs consisting of 3 or fewer zero-valent transition metal atoms.

3. A composition consisting of atomic quantum clusters (AQCs) consisting of 3 or fewer zero-valent metal atoms, and free of AQCs consisting of 2 zero-valent transition metal atoms.

4. The aqueous composition of claim 2, wherein the metal atoms are selected from Ag, Au, Cu, Pt, Fe, Cr, Pd, Ni, Rh, Pb, Ir, Ru, Os, Co, Ti, V or any combination thereof.

5. The aqueous composition of claim 4, wherein the metal atoms are selected from Ag, Au, Cu, Pt or any combination thereof.

6. The aqueous composition of claim 5, wherein the metal atoms are Ag.

7. The aqueous composition of claim 2, wherein the composition comprises a pharmaceutically acceptable excipient, diluent or carrier.

* * * * *